(12) United States Patent
Campbell et al.

(10) Patent No.: US 8,399,444 B2
(45) Date of Patent: Mar. 19, 2013

(54) BICYCLIC IMIDAZOLE AS DP1 RECEPTOR ANTAGONISTS

(75) Inventors: Ian Baxter Campbell, Stevenage (GB); Simon Peace, Stevenage (GB); John Martin Pritchard, Stevenage (GB); Daniel Tape, Stevenage (GB); Robert Charles Wheeler, Stevenage (GB)

(73) Assignee: GlaxoSmithKline Intellectual Property Development Ltd., Middlesex (GB)

( * ) Notice: Subject to any disclaimer, the term of this patent is extended or adjusted under 35 U.S.C. 154(b) by 0 days.

(21) Appl. No.: 13/133,738

(22) PCT Filed: Dec. 16, 2009

(86) PCT No.: PCT/EP2009/067356
§ 371 (c)(1),
(2), (4) Date: Jun. 9, 2011

(87) PCT Pub. No.: WO2010/070021
PCT Pub. Date: Jun. 24, 2010

(65) Prior Publication Data
US 2011/0245310 A1     Oct. 6, 2011

Related U.S. Application Data

(60) Provisional application No. 61/138,664, filed on Dec. 18, 2008.

(51) Int. Cl.
*A01N 43/00*    (2006.01)
*A61K 31/33*    (2006.01)
(52) U.S. Cl. .................. 514/183; 514/393; 548/302.7
(58) Field of Classification Search .................. 514/183, 514/393; 548/302.7
See application file for complete search history.

(56) References Cited

U.S. PATENT DOCUMENTS
2004/0180885 A1    9/2004 Torisu et al.

FOREIGN PATENT DOCUMENTS
EP        1424335 A       6/2004
WO    WO 9204343 A1 *    3/1992

OTHER PUBLICATIONS
STN Accession No. 1941:17980 CAPLUS.*

* cited by examiner

*Primary Examiner* — Brandon Fetterolf
*Assistant Examiner* — Jean Cornet
(74) *Attorney, Agent, or Firm* — J. Scott Young

(57) ABSTRACT

The present invention relates to compounds of formula (I):

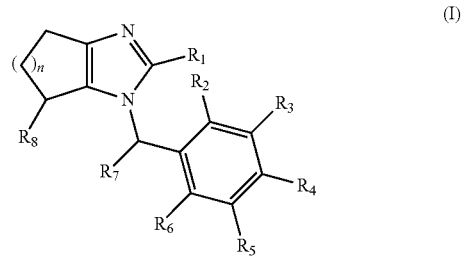

or pharmaceutically acceptable salts or solvates thereof, processes for their preparation, pharmaceutical compositions containing these compounds, and their use in the treatment of allergic disorders, such as allergic rhinitis and asthma.

18 Claims, 4 Drawing Sheets

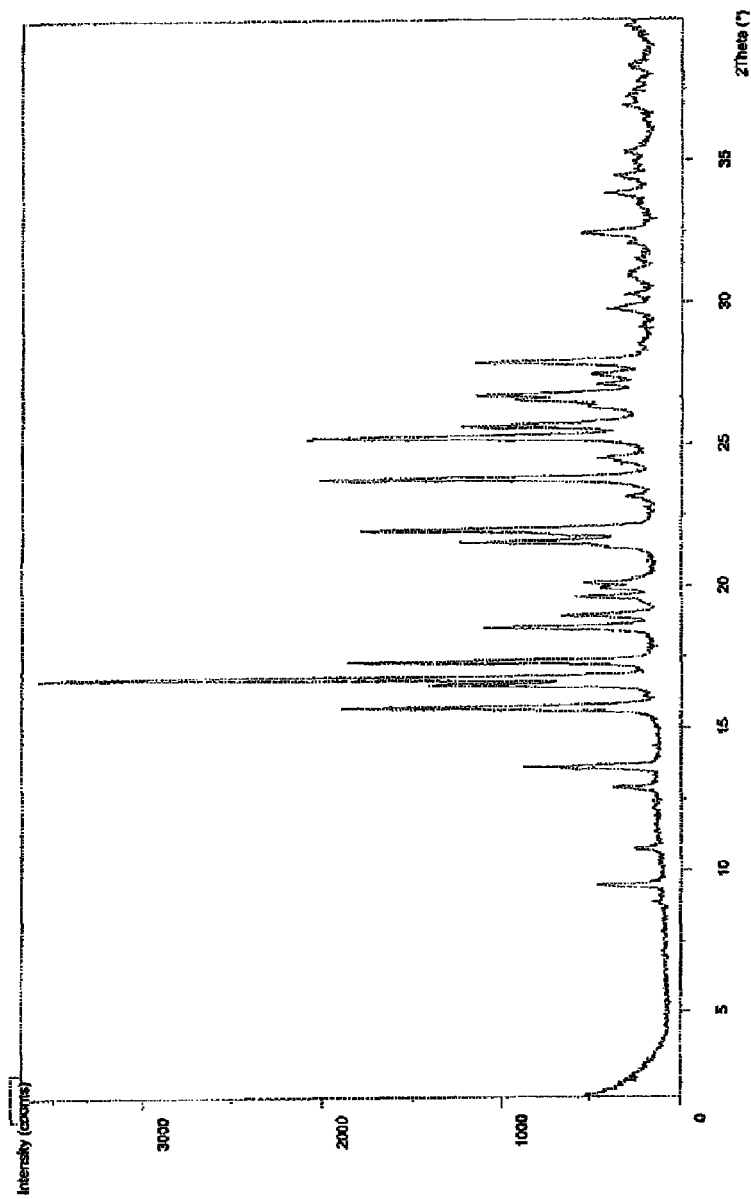
Figure 1: X-ray Powder Diffraction (XRPD) pattern of [(7R)-1-[(3,4-dichlorophenyl)methyl]-2-(1-methylethyl)-4,5,6,7-tetrahydro-1H-benzimidazol-7-yl]acetic acid (Example 40)

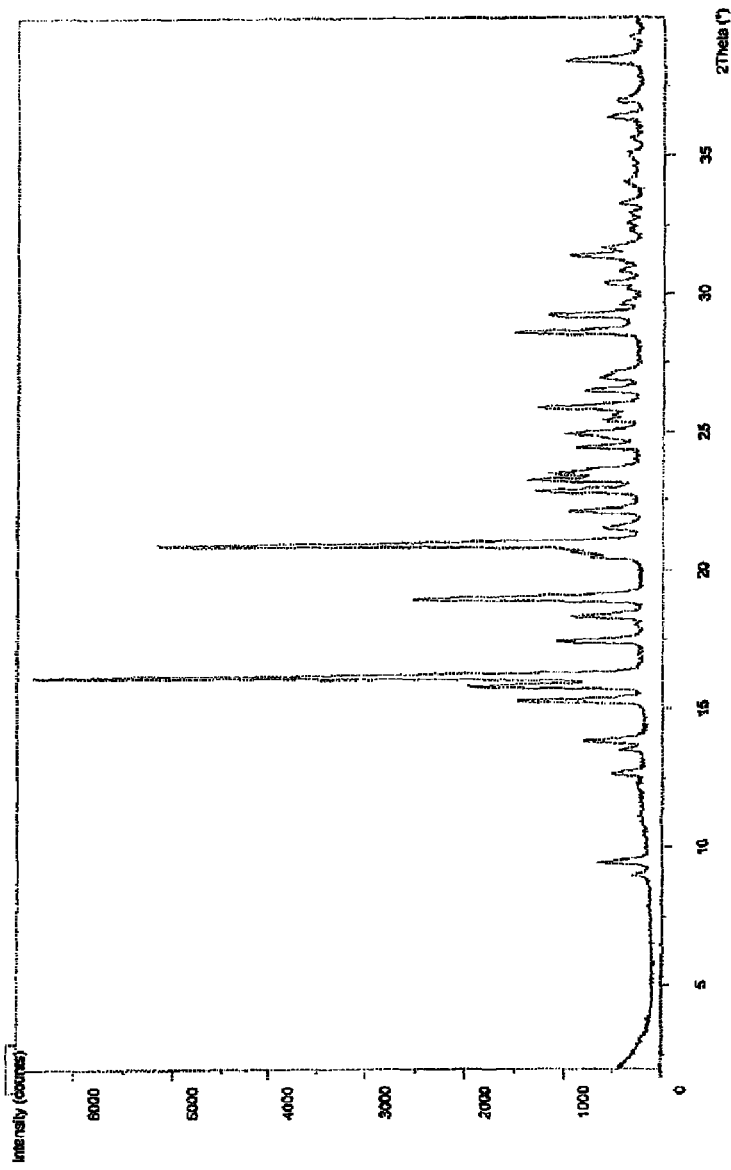
Figure 2: X-ray Powder Diffraction (XRPD) pattern of [(7R)-1-[(3,4-dichlorophenyl)methyl]-2-(1-methylethyl)-4,5,6,7-tetrahydro-1H-benzimidazol-7-yl]acetic acid (Example 40 (1st Alternative preparation))

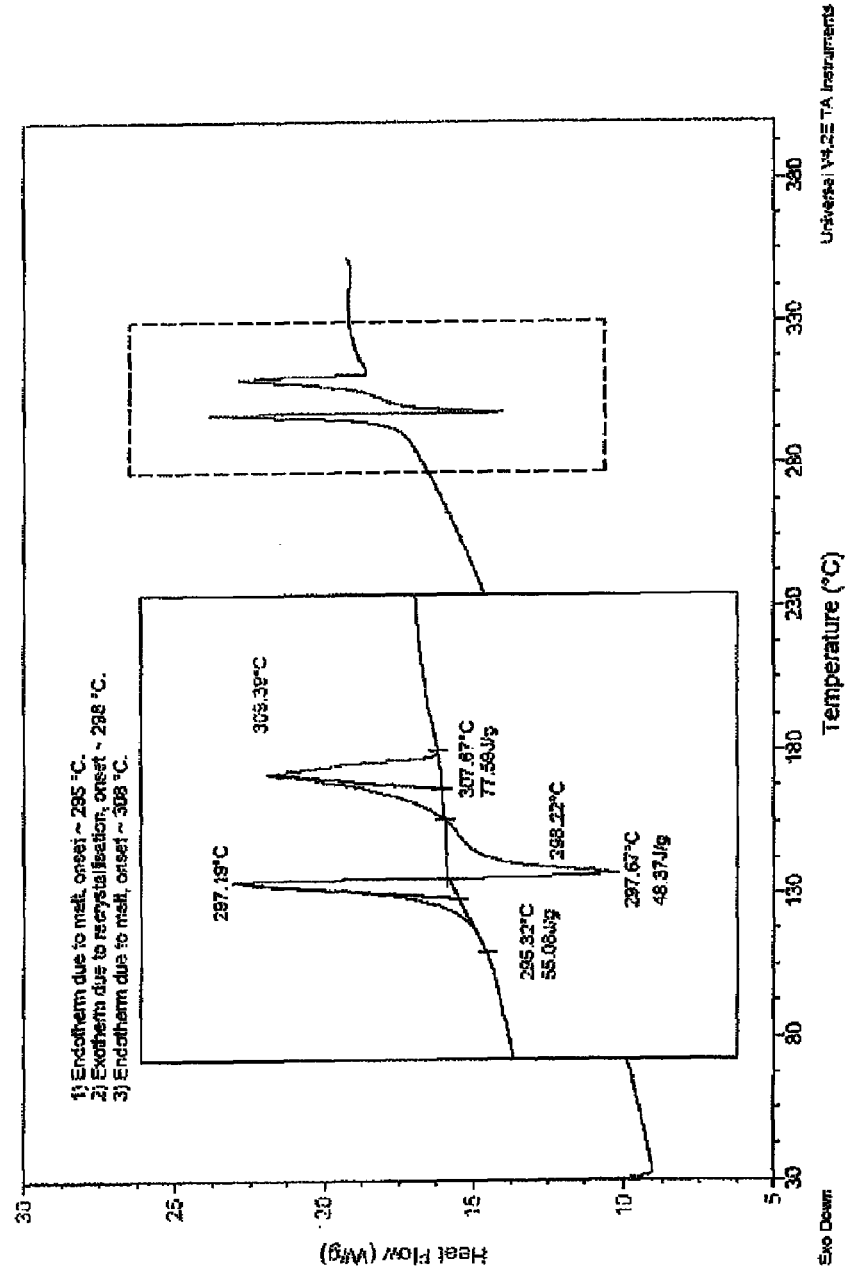
Figure 3: DSC thermogram of [(7R)-1-[(3,4-dichlorophenyl)methyl]-2-(1-methylethyl)-4,5,6,7-tetrahydro-1H-benzimidazol-7-yl]acetic acid (Example 40)

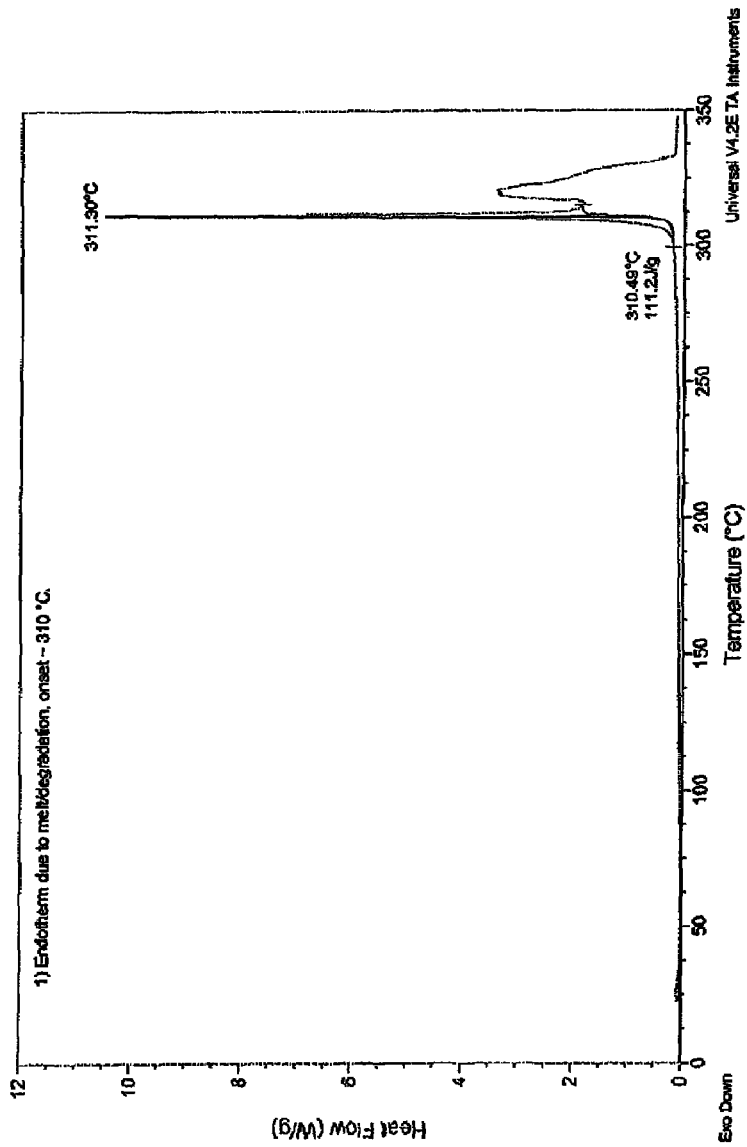
Figure 4: DSC thermogram of [(7R)-1-[(3,4-dichlorophenyl)methyl]-2-(1-methylethyl)-4,5,6,7-tetrahydro-1H-benzimidazol-7-yl]acetic acid (Example 40 (1st Alternative preparation))

BICYCLIC IMIDAZOLE AS DP1 RECEPTOR ANTAGONISTS

CROSS-REFERENCE TO RELATED APPLICATIONS

This application is filed pursuant to 35 USC 371 as a United States National Phase Application of International Patent Application Serial No. PCT/EP2009/067356 filed on Dec. 16, 2009, which claims priority from 61/138,664 filed on Dec. 18, 2008 in the United States.

FIELD OF THE INVENTION

The present invention relates to bicyclic imidazole compounds, processes for their preparation, pharmaceutical compositions containing these compounds, and their use in the treatment of allergic disorders, such as allergic rhinitis and asthma.

BACKGROUND OF THE INVENTION

Allergic rhinitis, which can be seasonal (hay fever) or perennial, is an upper-airway disorder that typically results in sneezing, nasal irritation, rhinorrhea and nasal congestion.

Asthma, which affects approximately 10% of the population, is a disorder that results in obstruction of the airways, bronchial hypereactivity and airway inflammation. The primary symptoms of asthma are coughing, wheezing, dyspnoea and tightening of the chest.

Local allergen challenge in sensitised individuals prompts an allergic and immune response, of which mast cells are known to play a central role. Mast cells become activated on challenge with IgE dependent stimuli, resulting in the release of chemical mediators. Various mast cell mediators, such as histamine, prostaglandin $D_2$ ($PGD_2$), leukotrienes and cytokines, have been implicated in the pathogenesis of allergic disorders.

Prostaglandins are produced by mast cells through the metabolism of arachidonic acid by cyclo-oxygenase (COX). Prostagladin $D_2$ ($PGD_2$) is the major cyclooxygenase derived metabolite produced on immunological challenge (Lewis R A, Soter N A, Diamond P T, Austen K F, Oates J A, Roberts L J II, J Immunol. 129, 1627-1631, 1982). It has been demonstrated that $PGD_2$ concentration in sensitised individuals increases in the presence of an allergen. In asthmatics, a bronchiol allergen challenge leads to a rapid rise in $PGD_2$ levels in the bronchoalveolar lavage (BAL) fluid [Murray J J et al, N. Engl. J. Med. 315, 800-804 (1986)]. Additionally, in individuals with allergic rhinitis and atopic dermatitis, antigen challenge causes a rise in $PDG_2$ levels in the nasal mucosa and skin, respectively (Naclerio R M et al, AM. Rev. Respir. Dis. 128, 597-602 (1983); and Charlesworth E N, J. Immunol. 146, 671-676 (1991)).

Intravenous administration of $PGD_2$ results in intense facial flushing and nasal congestion (Heavey D J et al, 28, 755-767 (1984)). $PGD_2$ is thought to induce nasal congestion in individuals with allergic rhinitis by causing vasodilation in the nasal mucosa (Park Y J, Clin. Allergy Immunol. 2002, 16, 275-293). It has been shown that insufflation of $PGD_2$ in humans results in a dose-dependent increase in nasal congestion.

$PGD_2$ exerts its activity through interaction with two distinct G-Protein-linked receptors: the D-prostanoid receptor 1 ($DP_1$) and the chemoattractant receptor homologous-molecule expressed on $TH_2$ cells ($CRTH_2$).

Allergic and immune responses in patients with allergic disorders are complex. Research has demonstrated that mediators, such as $PGD_2$, are responsible for the antigen-induced responses.

Antagonists of the $DP_1$ receptor may also be useful in the treatment of niacin induced flushing. Niacin, also referred to as nicotinic acid, is a water soluble vitamin that is used in the treatment of hypercholesterolaemia. Niacin reduces levels of low density lipoprotein cholesterol (LDL-C), as well as triglycerides (TG), whilst elevating the levels of high density lipoprotein cholesterol (HDL-C), thereby reducing cardiovascular morbidity and mortality. The most common side effect associated with niacin treatment is flushing, caused by its vasodilatory properties. Antagonism of the $DP_1$ receptor has been shown to limit or prevent niacin induced flushing.

There is a need for therapeutic agents which act as $DP_1$ receptor antagonists. Disclosed herein are bicyclic imidazole compounds that represent a novel class of $DP_1$ receptor antagonists.

SUMMARY OF THE INVENTION

According to the invention there is provided a compound of formula (I) or a pharmaceutically acceptable salt or solvate thereof:

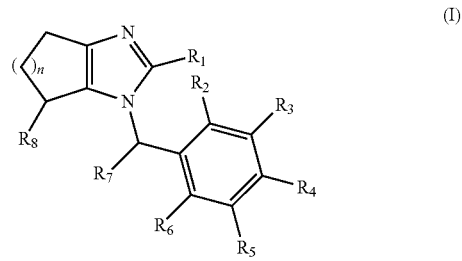

(I)

wherein:
$R_1$ represents $C_{3-6}$ alkyl or $C_{3-6}$ cycloalkyl;
$R_2$, $R_3$, $R_4$, $R_5$ and $R_6$ each independently represent hydrogen or halogen;
$R_7$ represents hydrogen, $C_{1-4}$ alkyl or $C_{1-4}$ alkoxy;
$R_8$ represents $-O(CH_2)_x COOH$ or $-(CH_2)_x COOH$
wherein,
x is 1 or 2; and
n represents 1, 2 or 3.

BRIEF DESCRIPTION OF THE DRAWINGS

FIG. 1 is an X-ray Powder Diffraction (XRPD) pattern of [(7R)-1-[(3,4-dichlorophenyl)methyl]-2-(1-methylethyl)-4,5,6,7-tetrahydro-1H-benzimidazol-7-yl]acetic acid (Example 40)

FIG. 2 is an X-ray Powder Diffraction (XRPD) pattern of [(7R)-1-[(3,4-dichlorophenyl)methyl]-2-(1-methylethyl)-4,5,6,7-tetrahydro-1H-benzimidazol-7-yl]acetic acid (Example 40 ($1^{st}$ Alternative preparation))

FIG. 3 is an DSC thermogram of [(7R)-1-[(3,4-dichlorophenyl)methyl]-2-(1-methylethyl)-4,5,6,7-tetrahydro-1H-benzimidazol-7-yl]acetic acid (Example 40)

FIG. 4 is an DSC thermogram of [(7R)-1-[(3,4-dichlorophenyl)methyl]-2-(1-methylethyl)-4,5,6,7-tetrahydro-1H-benzimidazol-7-yl]acetic acid (Example 40 ($1^{st}$ Alternative preparation))

DETAILED DESCRIPTION

As used herein, the term "alkyl" refers to a straight or branched hydrocarbon chain containing the specified number of carbon atoms. For example, $C_{3-6}$ alkyl means a straight or branched alkyl chain containing at least three, and at most six, carbon atoms. Illustrative examples of "alkyl" as used herein include propyl, butyl, pentyl or hexyl.

As used herein, the term "alkoxy" refers to an —O-alkyl group wherein "alkyl" is defined above.

As used herein, the term "cycloalkyl" refers to a cyclic, saturated hydrocarbon containing the specified number of carbon atoms. For example, $C_{3-6}$ cycloalkyl means a cyclic, saturated hydrocarbon containing at least three, and at most six, carbon atoms. Illustrative examples of cycloalkyl as used herein include cyclopropyl, cyclobutyl, cyclopentyl or cyclohexyl.

As used herein, the term "halogen" refers to F, Cl, or Br. The term "halogen" also includes I.

In one embodiment $R_1$ is propyl, butyl, cyclopropyl, or cyclopentyl.

In another embodiment $R_1$ is iso-propyl.

In another embodiment $R_7$ is hydrogen, $R_8$ is —($CH_2$)COOH and $R_4$ is halogen.

In another embodiment, $R_4$ is chloro.

In a further embodiment there is a compound of formula (I), or a pharmaceutically acceptable salt or solvate thereof, wherein:
$R_1$ is iso-propyl;
$R_2$, $R_5$, $R_6$ and $R_7$ are hydrogen;
$R_3$ is chloro or hydrogen;
$R_4$ is chloro;
$R_8$ is —($CH_2$)COOH; and
n represents 1, 2 or 3.

In a further embodiment the invention provides a compound of formula (I) selected from the group consisting of:
[3-[(4-chlorophenyl)methyl]-2-(1-methylethyl)-3,4,5,6-tetrahydrocyclopenta[d]imidazol-4-yl]acetic acid,
[1-[(4-chlorophenyl)methyl]-2-(1-methylethyl)-4,5,6,7-tetrahydro-1H-benzimidazol-7-yl]acetic acid,
[3-[(4-chlorophenyl)methyl]-2-(1-methylethyl)-3,4,5,6,7,8-hexahydrocyclohepta[d]imidazol-4-yl]acetic acid,
[3[(3,4-dichlorophenyl)methyl]-2-(1-methylethyl)-3,4,5,6-tetrahydrocyclopenta[d]imidazol-4-yl]acetic acid,
[1-[(3,4-dichlorophenyl)methyl]-2-(1-methylethyl)-4,5,6,7-tetrahydro-1H-benzimidazol-7-yl]acetic acid, and
[3-[(3,4-dichlorophenyl)methyl]-2-(1-methylethyl)-3,4,5,6,7,8-hexahydrocyclohepta[d]imidazol-4-yl]acetic acid;
or a pharmaceutically acceptable salt or solvate thereof.

In yet a further embodiment the invention provides a compound of formula (I) selected from the group consisting of:
(+)-[3-[(3,4-dichlorophenyl)methyl]-2-(1-methylethyl)-3,4,5,6,7,8-hexahydrocyclohepta[d]imidazol-4-yl]acetic acid,
(+)-[3-[(3,4-dichlorophenyl)methyl]-2-(1-methylethyl)-3,4,5,6-tetrahydrocyclopenta[d]imidazol-4-yl]acetic acid,
(−)-[1-[(4-chlorophenyl)methyl]-2-(1-methylethyl)-4,5,6,7-tetrahydro-1H-benzimidazol-7-yl]acetic acid, and
(−)-[1-[(3,4-dichlorophenyl)methyl]-2-(1-methylethyl)-4,5,6,7-tetrahydro-1H-benzimidazol-7-yl]acetic acid,
or a pharmaceutically acceptable salt or solvate thereof.

In a further embodiment there is a compound of formula (I), or a pharmaceutically acceptable salt or solvate thereof, wherein:
$R_1$ is iso-propyl;
$R_2$, $R_5$, $R_6$ and $R_7$ are hydrogen;
$R_3$ and $R_4$ are chloro;
$R_8$ is —($CH_2$)COOH; and
n represents 3.

In yet a further embodiment the invention provides:
(+)-[3-[(3,4-dichlorophenyl)methyl]-2-(1-methylethyl)-3,4,5,6,7,8-hexahydrocyclohepta[d]imidazol-4-yl]acetic acid,

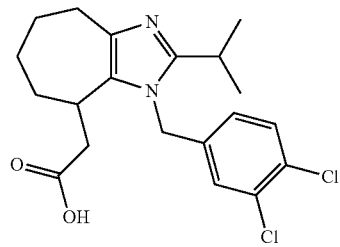 [SMILES: CC(C)c1nc2c(n1Cc1ccc(Cl)c(Cl)c1)C(CC(=O)O)CCCC2]

or a pharmaceutically acceptable salt or solvate thereof.

In yet a further embodiment the invention provides:
(−)-[1-[(3,4-dichlorophenyl)methyl]-2-(1-methylethyl)-4,5,6,7-tetrahydro-1H-benzimidazol-7-yl]acetic acid, of formula

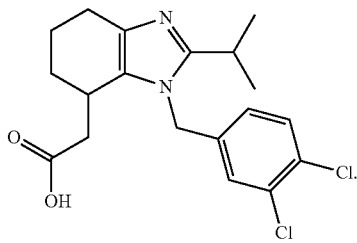 [SMILES: CC(C)c1nc2c(n1Cc1ccc(Cl)c(Cl)c1)C(CC(=O)O)CCC2]

In yet a further embodiment the invention provides:
(−)-[1-[(3,4-dichlorophenyl)methyl]-2-(1-methylethyl)-4,5,6,7-tetrahydro-1H-benzimidazol-7-yl]acetic acid, of formula

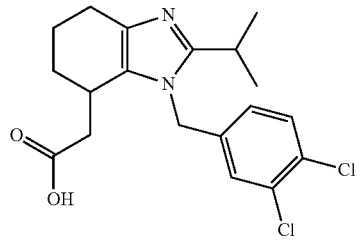 [SMILES: CC(C)c1nc2c(n1Cc1ccc(Cl)c(Cl)c1)C(CC(=O)O)CCC2]

or a pharmaceutically acceptable salt or solvate thereof.

In yet a further embodiment the invention provides:
[(7R)-1-[(3,4-dichlorophenyl)methyl]-2-(1-methylethyl)-4,5,6,7-tetrahydro-1H-benzimidazol-7-yl]acetic acid

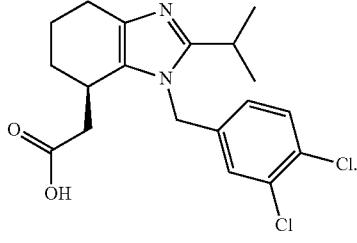 [SMILES: CC(C)c1nc2c(n1Cc1ccc(Cl)c(Cl)c1)[C@@H](CC(=O)O)CCC2]

It is understood that the present invention covers all combinations of substituent groups referred to herein above.

Compounds of formula (I), or pharmaceutically acceptable salts or solvates thereof, may exist in stereoisomeric forms as they may contain either one or two stereogenic centres. The individual stereoisomers (enantiomers and diastereomers) and mixtures of these are included within the scope of the present invention.

Salts of the compounds of formula (I) are included within the scope of the invention. Because of their potential use in medicine, the salts of the compounds of formula (I) are preferably pharmaceutically acceptable. Suitable pharmaceutically acceptable salts include both base addition salts and acid addition salts. A pharmaceutically acceptable base addition salt can be formed by reaction of a compound of formula (I) with a suitable inorganic or organic base (e.g. triethylamine, ethanolamine, triethanolamine, arginine, lysine or histidine), optionally in a suitable solvent such as an organic solvent, to give the base addition salt which is usually isolated for example by crystallisation and filtration. A pharmaceutically acceptable acid addition salt can be formed by reaction of a compound of formula (I) with a suitable inorganic or organic acid (such as hydrobromic, hydrochloric, hydroiodic, sulfuric, nitric, phosphoric, p-toluenesulfonic, methanesulfonic or naphthalenesulfonic acid), optionally in a suitable solvent such as an organic solvent, to give the salt which is usually isolated for example by crystallisation and filtration. Examples of pharmaceutically acceptable acid addition salts of a compound of formula (I) include the HCl, HBr, HI, sulfate or bisulfate, nitrate, phosphate or hydrogen phosphate, fumarate, maleate, saccharate, citrate, tartrate, gluconate, camsylate, methanesulfonate, ethanesulfonate, benzenesulfonate, p-toluenesulfonate and pamoate salts.

For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopaedia of Pharmaceutical Technology, Marcel Dekker Inc, New York 1996, Volume 13, page 453-497. Other salts that are not deemed pharmaceutically acceptable may be useful in the preparation of compounds of formula (I) and are included within the scope of the invention, such as ammonia and trifluoroacetic acid. The present invention encompasses all possible stoichiometric and non-stoichiometric forms of the salts of the compounds of formula (I).

The invention also includes all suitable isotopic variations of a compound of formula (I) or a salt or solvate thereof. An isotopic variation of a compound of formula (I), or a salt or solvate thereof, is defined as one in which at least one atom is replaced by an atom having the same atomic number but an atomic mass different from the atomic mass usually found in nature. Examples of isotopes that can be incorporated into compounds of the invention include isotopes of hydrogen, carbon, nitrogen, oxygen, fluorine and chlorine such as $^2$H, $^3$H, $^{13}$C, $^{14}$C, $^{15}$N, $^{17}$O, $^{18}$O, $^{18}$F and $^{36}$Cl, respectively. Certain isotopic variations of a compound of formula (I) or a salt or solvate thereof, for example, those in which a radioactive isotope such as $^3$H or $^{14}$C is incorporated, are useful in drug and/or substrate tissue distribution studies. Tritiated, i.e., $^3$H, and carbon-14, i.e., $^{14}$C, isotopes are particularly preferred for their ease of preparation and detectability. Further, substitution with isotopes such as deuterium, i.e., $^2$H, may afford certain therapeutic advantages resulting from greater metabolic stability, for example, increased in vivo half-life or reduced dosage requirements and hence may be preferred in some circumstances. Isotopic variations of a compound of formula (I), or a salt or solvate thereof, can generally be prepared by conventional procedures such as by the illustrative methods or by the preparations described in the Examples hereafter using appropriate isotopic variations of suitable reagents.

A compound of formula (I), or a pharmaceutically acceptable salt or solvate thereof, may be in amorphous or crystalline form. Moreover, a compound of formula (I), or a pharmaceutically acceptable salt or solvate thereof, may exist in one or more crystalline forms. Consequently, the present invention includes within its scope all forms of a compound of formula (I), or a pharmaceutically acceptable salt or solvate thereof.

The person skilled in the art will appreciate that many organic compounds can form complexes with solvents in which they are reacted or from which they are precipitated or crystallised. These complexes are known as "solvates". Where the solvent is water the complex is known as a "hydrate". The present invention encompasses all solvates of the compounds of formula (I).

The role of the $DP_1$ receptor in allergic disease has been investigated in a number of studies. In one such study, mice that were genetically deficient in $DP_1$ receptors had a lower concentration of $TH_2$ cytokines and reduced lymphocyte accumulation, in comparison with wild type mice (Matsuoka et al; Science, 2000, 287, 2013-2017). Additionally, the mutant mice showed only marginal infiltration of eosinophils and failed to develop airway hyperreactivity. In a further study, the effects of administering a $DP_1$ receptor antagonist, S-5751, to various allergic inflammation guinea pig models was assessed. In an allergic rhinitis model, early and late nasal responses were inhibited by oral administration of S-5751. Moreover, S-5751 alleviated antigen-induced eosinophil infiltration into the lung in an asthma model (Arimura et al; J. Pharmacol. Exp. Ther., 2001, 298, 411-419). Thus, a $DP_1$ receptor antagonist may be useful in the treatment of allergic disorders, such as allergic rhinitis.

Antagonists of the $DP_1$ receptor may also be useful in the treatment of niacin induced flushing. Niacin, also referred to as nicotinic acid, is a water soluble vitamin that is used in the treatment of hypercholesterolaemia. Niacin reduces levels of low density lipoprotein cholesterol (LDL-C), as well as triglycerides (TG), whilst elevating the levels of high density lipoprotein cholesterol (HDL-C), thereby reducing cardiovascular morbidity and mortality. The most common side effect associated with niacin treatment is flushing, caused by the vasodilatory property of niacin. Antagonism of the $DP_1$ receptor has been shown to limit or prevent niacin induced flushing (Paolini, John F. et al. American Journal of Cardiology (2008), 101(5), 625-630).

In a further embodiment the present invention also provides a compound of formula (I), or a pharmaceutically acceptable salt or solvate thereof, for use in therapy.

In yet a further embodiment the present invention provides a compound of formula (I), or a pharmaceutically acceptable salt or solvate thereof, for use in the treatment of an allergic disorder.

Allergic rhinitis is an allergic disorder of particular interest. Consequently, in yet a further embodiment the present invention provides a compound of formula (I), or a pharmaceutically acceptable salt or solvate thereof, for use in the treatment of allergic rhinitis.

In another embodiment the present invention includes the use of a compound of formula (I), or a pharmaceutically acceptable salt or solvate thereof, in the manufacture of a medicament for use in the treatment of an allergic disorder.

In another embodiment the present invention includes the use of a compound of formula (I), or a pharmaceutically acceptable salt or solvate thereof, in the manufacture of a medicament for use in the treatment of allergic rhinitis.

In another embodiment the present invention includes the use of a compound of formula (I), or a pharmaceutically acceptable salt or solvate thereof, in the manufacture of a medicament for use in the treatment of niacin induced flushing.

In a further embodiment the present invention provides a method for treating an allergic disorder, which comprises administering to a patient in need of treatment a therapeutically effective amount of a compound of formula (I), or a pharmaceutically acceptable salt or solvate thereof.

In a further embodiment the present invention provides a method for treating allergic rhinitis, which comprises administering to a patient in need of treatment a therapeutically effective amount of a compound of formula (I), or a pharmaceutically acceptable salt or solvate thereof.

In a further embodiment the present invention provides a method for treating niacin induced flushing, which comprises administering to a patient in need of treatment a therapeutically effective amount of a compound of formula (I), or a pharmaceutically acceptable salt or solvate thereof.

As used herein, the term "treatment" refers to prophylaxis of the condition, ameliorating or stabilising the specified condition, reducing or eliminating the symptoms of the condition, slowing or eliminating the progression of the condition, and preventing or delaying reoccurrence of the condition in a previously afflicted patient or subject.

As used herein, the term "therapeutically effective amount" refers to the quantity of a compound of formula (I), or a pharmaceutically acceptable salt or solvate thereof, which will elicit the desired biological response in an animal or human body.

A compound of formula (I), or a pharmaceutically acceptable salt or solvate thereof, may be administered for use in therapy as the raw chemical. Alternatively, a compound of formula (I), or a pharmaceutically acceptable salt or solvate thereof, may be presented as a suitable pharmaceutical composition. Thus, a further embodiment of the invention provides a pharmaceutical composition, which comprises a compound of formula (I), or a pharmaceutically acceptable salt or solvate thereof, in combination with one or more pharmaceutically acceptable carriers and/or excipients.

In yet a further embodiment the invention provides a pharmaceutical composition comprising [3-[(3,4-dichlorophenyl)methyl]-2-(1-methylethyl)-3,4,5,6,7,8-hexahydrocyclohepta[d]imidazol-4-yl]acetic acid, or a pharmaceutically acceptable salt or solvate thereof, and one or more pharmaceutically acceptable carriers or excipients.

In yet a further embodiment the invention provides a pharmaceutical composition comprising (−)-[1-[(3,4-dichlorophenyl)methyl]-2-(1-methylethyl)-4,5,6,7-tetrahydro-1H-benzimidazol-7-yl]acetic acid, or a pharmaceutically acceptable salt or solvate thereof, and one or more pharmaceutically acceptable carriers or excipients.

In yet a further embodiment the invention provides a pharmaceutical composition comprising [(7R)-1-[(3,4-dichlorophenyl)methyl]-2-(1-methylethyl)-4,5,6,7-tetrahydro-1H-benzimidazol-7-yl]acetic acid, or a pharmaceutically acceptable salt or solvate thereof, and one or more pharmaceutically acceptable carriers or excipients.

A pharmaceutical composition of a compound of formula (I), or a pharmaceutically acceptable salt or solvate thereof, may be formulated for administration by any appropriate route, for example by the nasal, inhaled, oral (including buccal or sublingual), topical (including buccal, sublingual, transdermal, epicutaneous) or parenteral (subcutaneous, intramuscular, intravenous, intradermal) route. Thus, a pharmaceutical composition of a compound of formula (I), or a pharmaceutically acceptable salt or solvate thereof, may be formulated as, for example, a solution or suspension (aqueous or non-aqueous), tablet, capsule, powder, granule, lozenge, lotion, cream, ointment, gel, foam or reconstitutable powder depending on the particular route of administration. Such pharmaceutical compositions may be prepared by any method known in the art of pharmacy, for example by bringing into association the active ingredient with the carrier(s) and/or excipient(s).

Tablets and capsules for oral administration may be in unit dose presentation form, and may contain conventional excipients such as binding agents, for example syrup, acacia, gelatine, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatine, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Pharmaceutical compositions of a compound of formula (I) or a pharmaceutically acceptable salt or solvate thereof, for topical administration, may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The compositions may also contain compatible conventional carriers, such as cream or ointment bases and ethanol or oleyl alcohol for lotions. Such carriers may be present as from about 1% up to about 98% of the composition. More usually they will form up to about 80% of the composition.

Pharmaceutical compositions adapted for parenteral administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Pharmaceutical compositions for topical administration to the lung or nose may include aerosol compositions and dry powder compositions.

Aerosol compositions may be developed, with the use of a suitable liquefied propellant, for delivery from pressurised packs, such as a metered dose inhaler. Aerosol compositions can be either a suspension or a solution and generally contain the compound of formula (I), or a pharmaceutically acceptable salt or solvate thereof, and a suitable propellant such as a fluorocarbon or hydrogen-containing chlorofluorocarbon or mixtures thereof, particularly hydrofluoroalkanes, especially 1,1,1,2-tetrafluoroethane, 1,1,1,2,3,3,3-heptafluoro-n-propane or a mixture thereof. The aerosol composition may optionally contain additional formulation excipients well known in the art such as surfactants eg oleic acid or lecithin and cosolvents eg ethanol. Aerosol compositions will generally be retained in a pressurised canister (eg an aluminium canister) closed with a valve (eg a metering valve) and fitted into an actuator with a mouthpiece. Aerosol compositions may also include aqueous solutions or suspensions that are delivered to the nose or lungs by nebulisation.

Dry powder compositions for topical delivery to the lungs or nose generally contain a powder mix of a compound of formula (I) or a pharmaceutically acceptable salt or solvate thereof and a suitable carrier, such as lactose or starch. Dry powder compositions for topical delivery to the lung or nose may, for example, be presented in capsules and cartridges for use in an inhaler or insufflator of, for example, gelatine. Each capsule or cartridge may generally contain between 20 µg-10 mg of the compound of formula (I), or a pharmaceutically acceptable salt or solvate thereof. Alternatively, the compounds of formula (I), or pharmaceutically acceptable salts or solvates thereof, may be presented without excipients. Packaging of the pharmaceutical composition may be suitable for unit dose or multi-dose delivery. In the case of multi-dose delivery, the composition can be pre-metered (eg as in Diskus, see GB 2242134 or Diskhaler, see GB 2178965, 2129691 and 2169265) or metered in use (eg as in Turbuhaler, see EP 69715). An example of a unit-dose device is Rotahaler (see GB 2064336). The Diskus inhalation device comprises an elongate strip formed from a base sheet having a plurality of recesses spaced along its length and a lid sheet hermetically but peelably sealed thereto to define a plurality of containers, each container having therein an inhalable composition comprising a compound of formula (I), or a pharmaceutically acceptable salt or solvate thereof, preferably combined with a carrier, such as lactose. Preferably, the strip is sufficiently flexible to be wound into a roll. The lid sheet and base sheet will preferably have leading end portions which are not sealed to one another and at least one of the said leading end portions is constructed to be attached to a winding means. Also, preferably the hermetic seal between the base and lid sheets extends over their whole width. The lid sheet may preferably be peeled from the base sheet in a longitudinal direction from a first end of the said base sheet.

Medicaments for administration by inhalation desirably have a controlled particle size. The optimum particle size for inhalation into the bronchial system is usually 1-10 µm, preferably 2-5 µm. Particles having a size above 20 µm are generally too large when inhaled to reach the small airways. To achieve these particle sizes the particles of compound of formula (I), or a pharmaceutically acceptable salt or solvate thereof, may be size reduced by conventional means eg by micronisation. The desired fraction may be separated out by air classification or sieving. Preferably, the particles will be crystalline, prepared for example by a process which comprises mixing in a continuous flow cell in the presence of ultrasonic radiation a flowing solution of compound of formula (I), or a pharmaceutically acceptable salt or solvate thereof, as medicament in a liquid solvent with a flowing liquid antisolvent for said medicament (eg as described in International Patent Application PCT/GB99/04368). Alternatively, the particles may be prepared by a process which comprises admitting a stream of solution of the substance in a liquid solvent and a stream of liquid antisolvent for said substance tangentially into a cylindrical mixing chamber having an axial outlet port such that said streams are thereby intimately mixed through formation of a vortex and precipitation of crystalline particles of the substance is thereby caused (eg as described in International Patent Application PCT/GB00/04237). When an excipient such as lactose is employed, generally, the particle size of the excipient will be much greater than the inhaled medicament within the present invention. When the excipient is lactose it will typically be present as milled lactose, wherein not more than 85% of lactose particles will have a MMD of 60-90 µm and not less than 15% will have a MMD of less than 15 µm.

Pharmaceutical compositions for topical administration to the nose may also be developed for delivery by nasal spray or as nasal droplets. Pharmaceutical compositions for nasal administration may be developed in such a way to allow the medicament(s) to be delivered to all appropriate areas of the nasal cavities (the target tissue). Moreover, a pharmaceutical composition may be developed for nasal administration, which permits the medicament(s) to remain in contact with the target tissue for an increased period of time.

A suitable dosing regime for a pharmaceutical composition administered topically to the nose by use of a nasal spray may be for the patient to inhale slowly through the nose subsequent to the nasal cavity being cleared. During inhalation, the composition may be administered to one nostril while the other is manually compressed. This procedure may then be repeated for the other nostril. Generally, one or two sprays per nostril may be administered by the above procedure up to two or three times each day. Typically, each spray to the nostril may deliver from about 25 to about 100 µL of the pharmaceutical composition.

Pharmaceutical compositions for topical administration to the nose by nasal spray or as nasal drops may be prepared as a solution or suspension. The solution or suspension may be aqueous or non-aqueous based, and may contain one or more pharmaceutically acceptable excipients, such as suspending agents, preservatives, isotonicity adjusting agents, buffering agents, wetting agents, anti-oxidants, sweetening agents and taste-masking agents.

A pharmaceutical composition prepared as a suspension for topical administration by nasal spray or as nasal drops may contain one or more suspending agents. Examples of suspending agents include carboxymethylcellulose, methylcellulose, veegum, tragacanth, bentonite and polyethylene glycols.

Pharmaceutical compositions for nasal administration by nasal spray or nasal drops containing suspended medicament(s) may include one or more pharmaceutically acceptable wetting agent(s), which function to wet the particles of the medicament, thereby facilitating their dispersion in the aqueous phase of the composition. Examples of pharmaceutically acceptable wetting agents include fatty alcohols, esters and ethers, such as polyoxyethylene (20) sorbitan monooleate (polysorbate 80).

One or more preservatives may be present in the pharmaceutical composition for nasal administration by nasal spray or nasal drops to prevent microbial contamination or growth. Examples of pharmaceutically acceptable preservatives or anti-microbial agents may include chelating agents (e.g EDTA), quaternary ammonium compounds (e.e benzalkonium chloride, benzethonium chloride, cetrimide and cetylpyridinium chloride), mercurial agents (e.g. phenylmercuric nitrate, phenylmercuric acetate and thimerosal), alcoholic agents (e.g. chlorobutanol, phenylethyl alcohol and benzyl alcohol), antibacterial esters (e.g. esters of para-hydroxybenzoic acid) and other anti-microbial agents such as chlorhexidine, chlorocresol, sorbic acid and its salts (e.g. potassium sorbate), and polymyxin. A pharmaceutical composition for nasal administration by nasal spray or nasal drops may be prepared unpreserved.

An isotonicity adjusting agent may be included in the pharmaceutical composition for nasal administration by nasal spray or nasal drops to achieve isotonicity with the target tissue in the nasal cavity, resulting in reduced levels of irritancy. Examples of isotonicity adjusting agents suitable for pharmaceutical compositions include sodium chloride, dextrose, xylitol and calcium chloride.

Pharmaceutical compositions for nasal administration by nasal spray or nasal drops may be buffered by the addition of pharmaceutically acceptable buffering agents, such as sodium citrate and citric acid.

It should be understood that in addition to the ingredients particularly mentioned above, the pharmaceutical compositions may include other agents conventional in the art having regard to the type of formulation in question.

A compound of formula (I), or a pharmaceutically acceptable salt or solvate thereof, may also be used in combination with one or more other therapeutically acceptable agents, for example antagonists of the H1 receptor (e.g. diphenhydramine, loratadine, desloratadine, fexofenadine, azelastine, ceterizine, promethazine, levocabastine and clemastine), antagonists (and/or inverse agonists) of the H4 receptor (e.g. compounds disclosed in Jablonowski et al., *J. Med. Chem.* 46:3957-3960 (2003)), dual H1/H3 receptor antagonists (e.g. compounds disclosed in WO 2007/071691) and $DP_2$ ($CRTH_2$) antagonists.

A compound of formula (I), or a pharmaceutically acceptable salt or solvate thereof, may be useful in the treatment of niacin induced flushing. Consequently, in yet a further embodiment the invention provides the use of a compound of formula (I), or a pharmaceutically acceptable salt or solvate thereof, in combination with niacin for the manufacture of a medicament for the treatment of hypercholesterolaemia and the reduction of concomitant niacin induced flushing.

It will be clear to a person skilled in the art that, where appropriate, the other therapeutic agent(s) may be used in the form of salts, or prodrugs, or as esters (e.g lower alkyl esters), or as solvates (e.g. hydrates) to optimise the activity and/or stability and/or physical characteristics (e.g. solubility) of the therapeutic agent. It will be clear also that, where appropriate, the therapeutic agent(s) may be used in optically pure form.

The invention thus provides in a further embodiment a combination comprising a compound of formula (I), or a pharmaceutically acceptable salt or solvate thereof, together with one or more further therapeutic agents.

Compounds of formula (I), or pharmaceutical acceptable salts or solvates thereof, may be prepared in a variety of ways. In the following reaction schemes and hereafter, $R_9$ is as defined in the text describing reaction scheme 1. These processes form further aspects of the invention.

Throughout the specification, general formulae are designated by Roman numerals (I), (II), (III), (IV) etc. Subsets of these general formulae are defined as (Ia), (Ib), (Ic) etc. . . . (IVa), (IVb), (IVc) etc.

Acids of the general formula (I) may be prepared from esters (II) (for example $R_9$=ethyl or benzyl) according to reaction scheme 1 by treatment with a suitable base (for example sodium hydroxide) in a polar solvent (such as methanol or tetrahydrofuran).

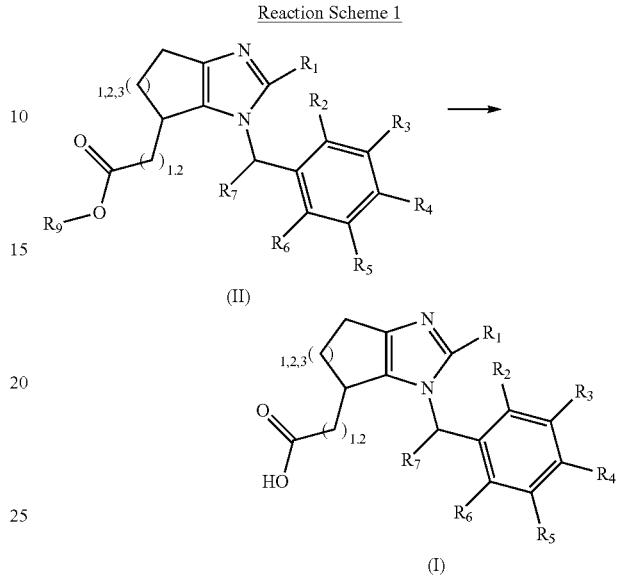

Reaction Scheme 1

Benzyl esters of the general formula (IIa) may be prepared from acids (I) according to reaction scheme 2 by treatment with an appropriate carbodiimide coupling reagent, such as DCC or EDC, in the presence of benzyl alcohol and DMAP in an appropriate solvent such as dichloromethane. Benzyl esters of this nature may be resolved into two enantiomers by chiral chromatography by elution of the mixture of enantiomers in a mobile phase (for example ethanol in heptane) over a chiral stationary phase (such as Chiralpack AD or Chiralcel OJ).

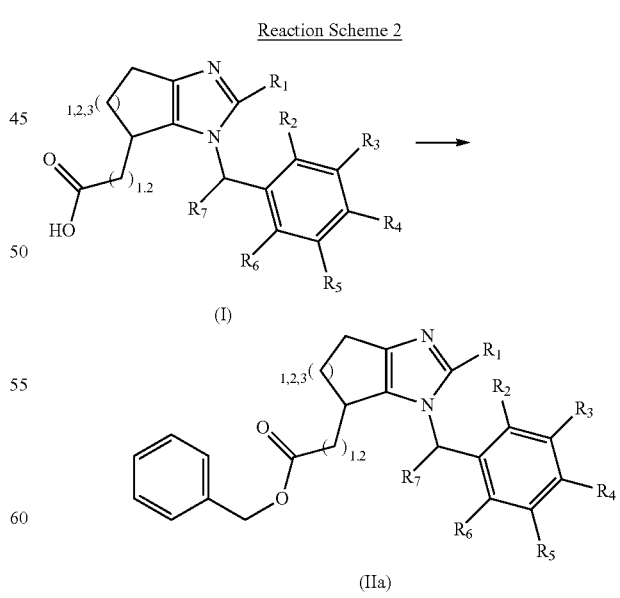

Reaction Scheme 2

Acids of the general formula (Ia) may also be prepared from tris-esters (III) according to reaction scheme 3 by a two-step process for example treatment with a suitable base (such as sodium hydroxide) in a suitable protic solvent (such as methanol) followed by removal of solvent and treatment with an acidic solvent (such as acetic acid).

Reaction Scheme 3

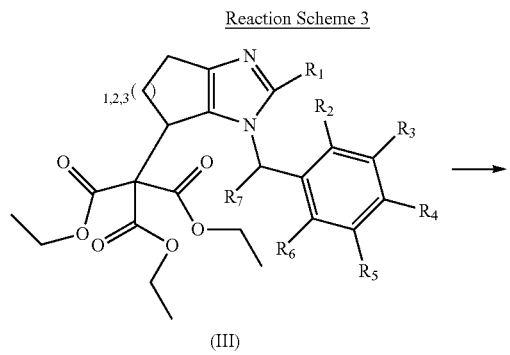

(III)

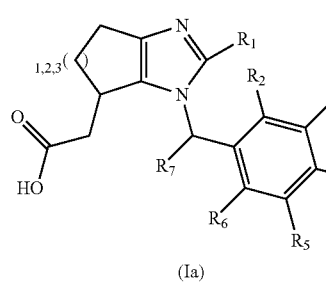

(Ia)

Tris-esters of the general formula (III) may be prepared from alcohols of the general formula (IV) according to reaction scheme 4 by treatment with an alcohol activating mixture (such as DIAD and trimethylphosphine) in the presence of triethyl-methanetricarboxylate in a suitable solvent (such as a mixture of tetrahydrofuran and toluene). Enantio-enriched (III) may be obtained from enantio-enriched (IV) using the above protocol. The enantiomers of (III) may be resolved into two enantiomers by chiral chromatography by elution of the mixture of enantiomers in a mobile phase (for example ethanol in heptane) over a chiral stationary phase (such as Chiralpack AD). The entiomeric excess (ee) of enantio-enriched samples of (III) may be increased by crystallisation of the racemic material, for example by seeding with a racemic sample, followed by filtration, providing enantio-enriched (III) upon concentration of the filtrate.

Reaction Scheme 4

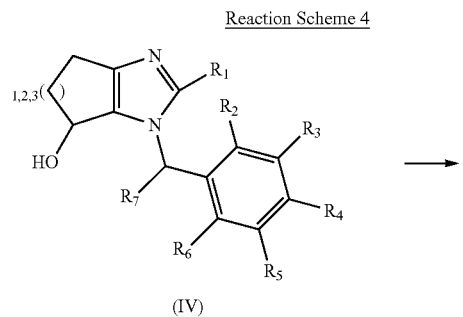

(IV)

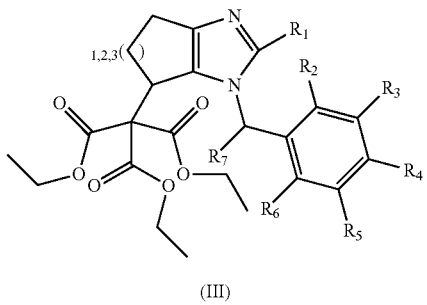

(III)

Alcohols of the general formula (IV) may be prepared from the corresponding ketones (V) according to reaction scheme 5 by treatment with a suitable hydride-based reducing agent (such as sodium borohydride) in the presence of an appropriate solvent (such as a mixture of dichloromethane and methanol). The enantiomers of (IV) may be resolved into two enantiomers by chiral chromatography by elution of the mixture of enantiomers in a mobile phase (for example ethanol in heptane) over a chiral stationary phase (such as Chiralpack AD). Enantio-enriched (IV) may also be obtained by treatment of (V) with borane in the presence of an enantioselective reducing agent such as (S)-(−)-2-methyl-CBS-oxazaborolidine.

Reaction Scheme 5

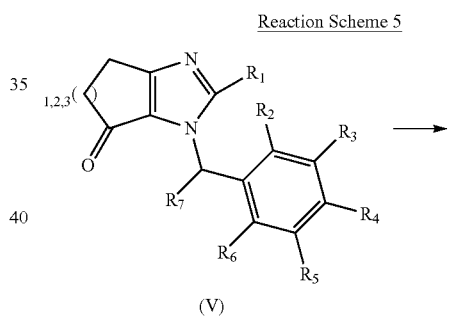

(V)

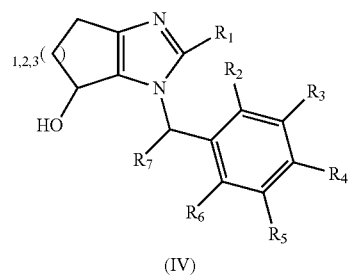

(IV)

Compounds of the general formula (V) may be prepared by the alkylation of compounds of the general formula (VI) according to reaction scheme 6 by treatment with an alkyl bromide (such as (VII)) in the presence of a suitable basic aqueous medium (such as aqueous sodium hydroxide), a phase-transfer catalyst (such as tetrabutylammonium bromide) in a solvent that is immiscible with water (such as toluene).

Reaction Scheme 6

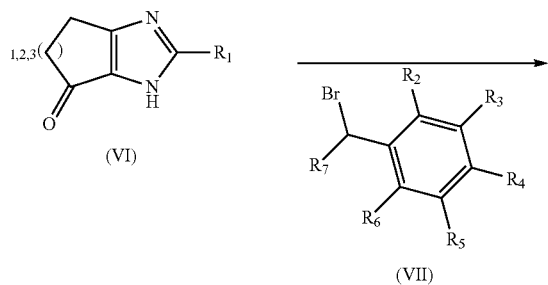

Compounds of the general formula (VI) may be prepared from (VIII) according to reaction scheme 7 by treatment with aminidines of the general formula (IX) in the presence of a suitable base (such as potassium carbonate) in an aprotic solvent (such as N,N-dimethylformamide). Compounds of the formula (VIII) have been reported in the literature (n=1: Curran, D. P., Jasperse, C. P. *J. Am. Chem. Soc,* 1990, 5601; n=2: Shepherd, R. G., White, A. C. *J. Chem. Soc. Perkin Trans.* 1, 1987, 1972.).

Reaction Scheme 7

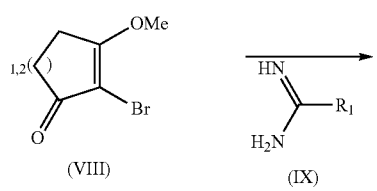

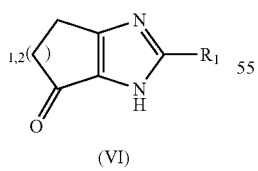

Compounds of the general formula (X) may be prepared from (XI) according to reaction scheme 8 by treatment with amidines (IX) in the presence of a suitable basic aqueous medium (such as aqueous sodium hydroxide), a phase-transfer catalyst (such as tetrabutylammonium bromide) in a solvent that is immiscible with water (such as toluene).

Reaction Scheme 8

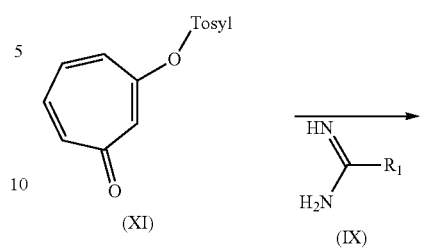

Compounds of the general formula (VIa) may be prepared from (X) according to reaction scheme 9 by hydrogenation over a suitable metal catalyst (such as palladium on carbon) in an appropriate solvent (such as methanol).

Reaction Scheme 9

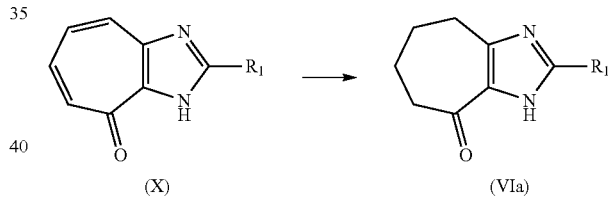

Compounds of the general formula (IIb) may be prepared from (XII) according to reaction scheme 10 by treatment with a siliyl chloride (such as TMSCI) and an iodide source (such as sodium iodide) in a suitable polar aprotic solvent (such as acetonitrile).

Reaction Scheme 10

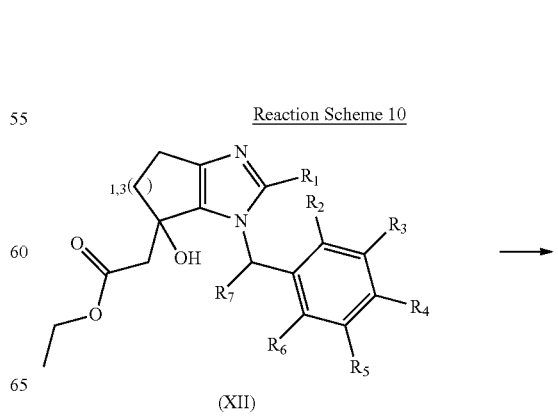

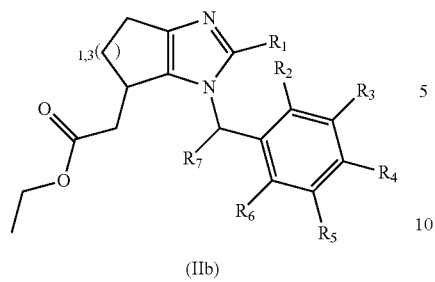

(IIb)

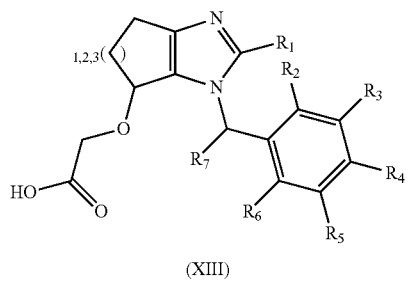

(XIII)

Compounds of the general formula (XII) may be prepared from (V) according to reaction scheme 11 by pre-treatment of ethyl acetate with a strong base (such as LiHMDS) in a polar aprotic solvent (such as tetrahydrofuran) and then treatment with (V).

Compounds of the general formula (Ib) may also be prepared from (XIV) according to reaction scheme 13 by hydrogenation over a suitable metal catalyst (such as palladium on carbon) in an appropriate solvent (such as methanol) followed by treatment with a base (such as sodium hydroxide) in a polar solvent (such as ethanol).

Reaction Scheme 11

Reaction Scheme 13

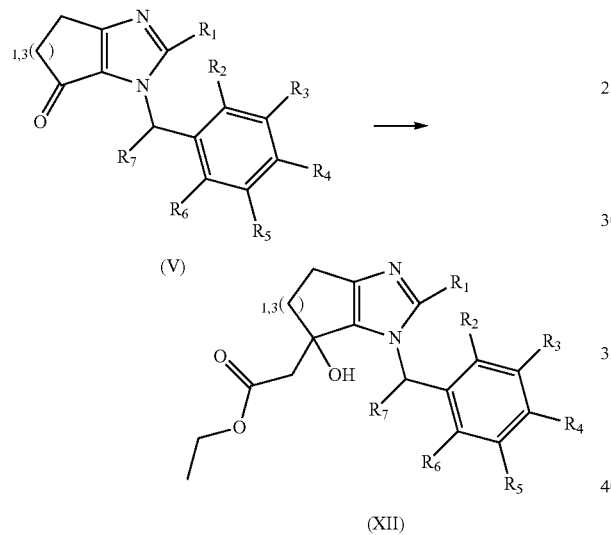

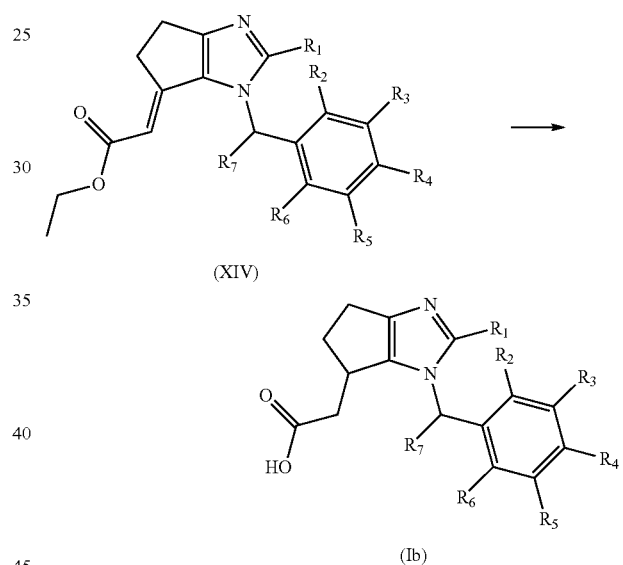

Compounds of the general formula (XIII) may be prepared from (VI) according to scheme 12 by treatment with a strong base (such as sodium hydride) and an appropriate alpha-bromoacetate (XXVI) (such as ethyl bromoacetate) in a polar aprotic solvent (such as tetrahydrofuran). The acid (XIII) may be delivered directly by this approach; however a second hydrolysis step of the intermediate ester may be achieved using an appropriate base (for example sodium hydroxide) in a polar solvent (such as methanol or tetrahydrofuran).

Compounds of the general formula (XIV) may be prepared from (XIIa) according to reaction scheme 14 by treatment with a silyl chloride (such as TMSCI) and an iodide source (such as sodium iodide) in a suitable polar aprotic solvent (such as acetonitrile).

Reaction Scheme 12

Reaction Scheme 14

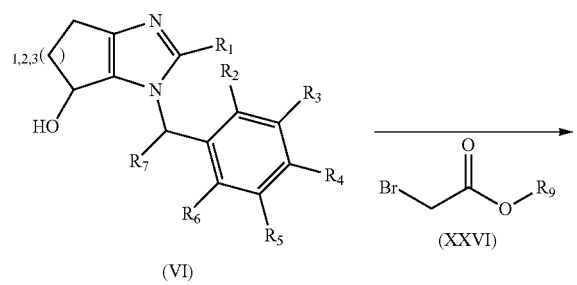

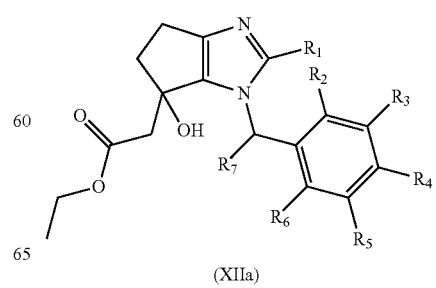

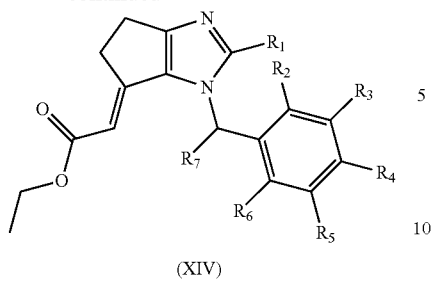

(XIV)

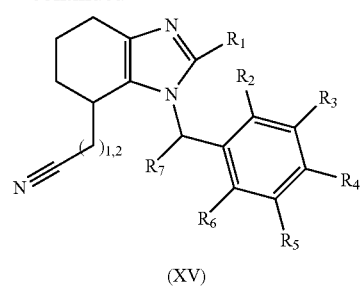

(XV)

Compounds of the general formula (Ic) may also be prepared from (XV) according to reaction scheme 15 by treatment with a base (such as lithium hydroxide) in an appropriate polar protic solvent (such as methanol).

Compounds of the general formula (XVI) may be prepared from (XVII) according to reaction scheme 17 by treatment with an appropriate hydride reducing agent (such as lithium aluminium hydride) or using a borane source, such as borane-dimethylsulfide complex, in an appropriate aprotic solvent (such as tetrahydrofuran).

Reaction Scheme 15

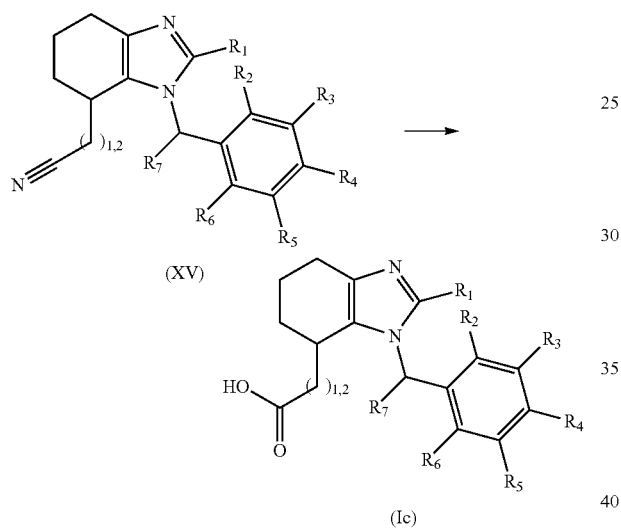

Reaction Scheme 17

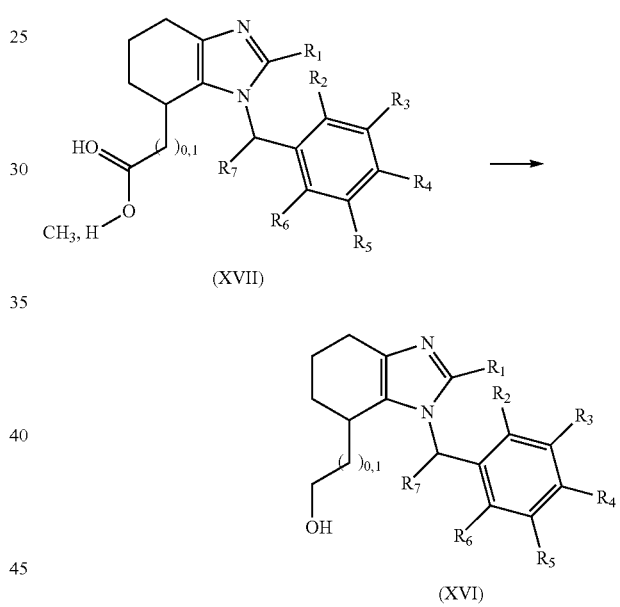

Compounds of the general formula (XV) may be prepared from (XVI) according to reaction scheme 16 in a two-step procedure firstly by treatment with an alcohol activating agent (such as mesyl chloride) in an appropriate aprotic solvent (such as dichloromethane) followed by treatment with a source of cyanide (such as sodium cyanide) in a polar aprotic solvent (such as dimethyl sulfoxide). Nitriles of this nature may be resolved into two enantiomers by chiral chromatography by elution of the mixture of enantiomers in a mobile phase (for example ethanol in heptane) over a chiral stationary phase (such as Chiralpack AD).

Compounds of the general formula (XVIIa) may be prepared from (XVIII) according to reaction scheme 18 by treatment with an acrylate ester (such as methyl acrylate) in the absence of solvent.

Reaction Scheme 16

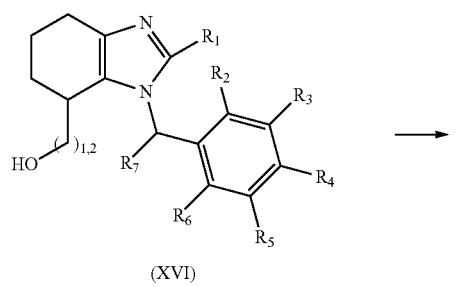

(XVI)

Reaction Scheme 18

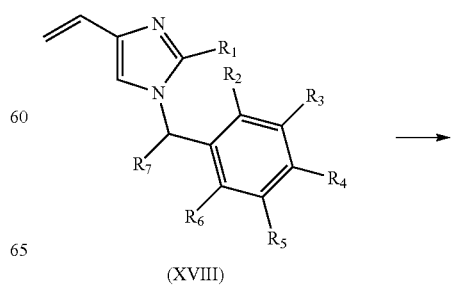

(XVIII)

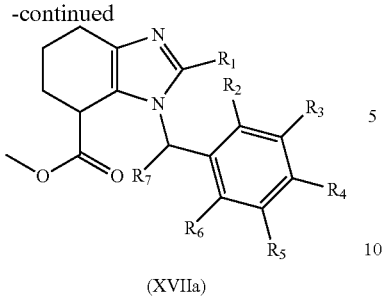

(XVIIa)

Compounds of the general formula (XVIII) may be prepared from (XIX) according to reaction scheme 19 by treatment with a vinyl metal transfer reagent (such as tributylvinyl tin) in the presence of a source of palladium (such as Pd$_2$dba$_3$) and a suitable phosphine ligand (such as triphenylphosphine) in an appropriate solvent (such as N,N-dimethylformamide).

Reaction Scheme 19

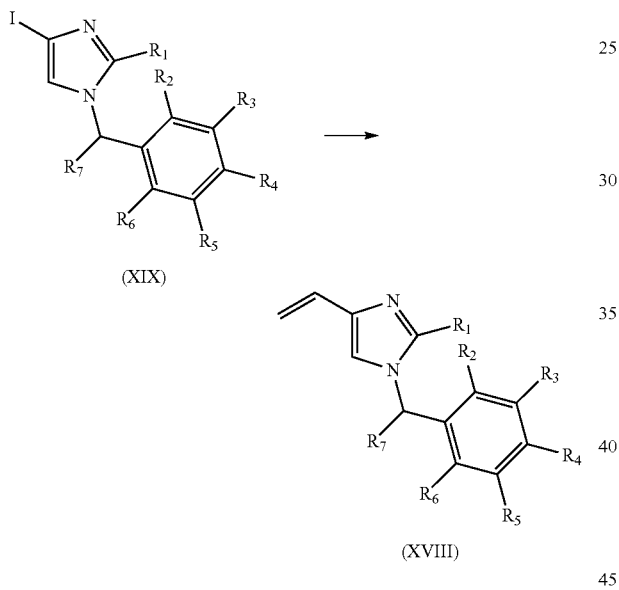

(XVIII)

Compounds of the general formula (XIX) may be prepared from (XX) according to reaction scheme 20 by treatment with a Grignard reagent (such as ethylmagnesium bromide) in an appropriate aprotic solvent (such as diethyl ether or tetrahydrofuran) followed by treatment with an acidic source (such as ammonium chloride).

Reaction Scheme 20

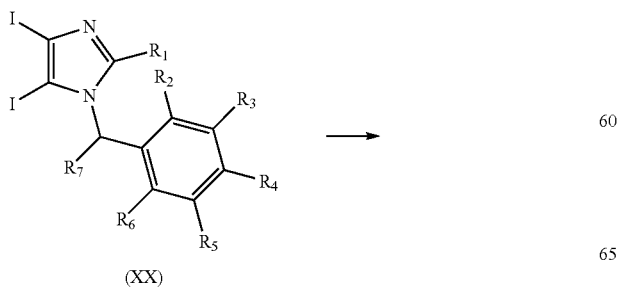

(XX)

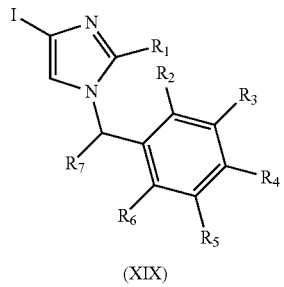

(XIX)

Compounds of the general formula (XX) may be prepared from (XXI) (such as 2-isopropyl-4,5-diiodoimidazole; Aissaoui, H., Boss, C., Gude, M., Koberstein, Ralf., Sifferlen, T. PCT Int. Appl. (2008), WO2008078291A1) according to reaction scheme 21 firstly by treatment with a base (such as NaHMDS) then by an alkyl bromide (VII) (such as 4-chlorobenzyl bromide) in an aprotic solvent (such as toluene).

Reaction Scheme 21

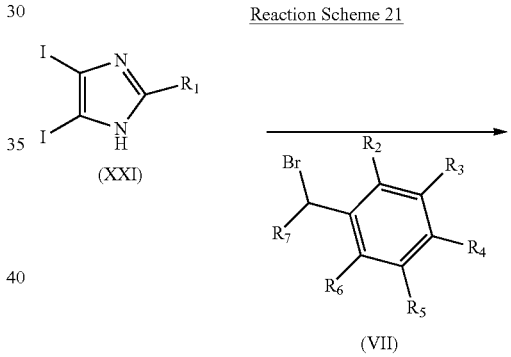

(XXI)                    (VII)

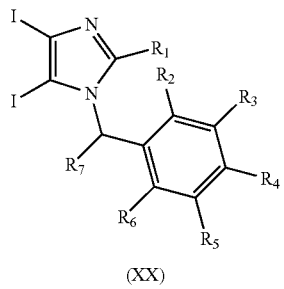

(XX)

Compounds of the general formula (IIc) may also be prepared from (XXII) according to reaction scheme 22 by treatment with an aliphatic carboxaldehyde (XXIII) (such as cyclopentane carboxaldehyde) an amine (XXIV) (such as 3,4-dichlorobenzylamine) a source of ammonia (such as ammonium chloride) and an acid (such as acetic acid) in an appropriate aprotic solvent (such as chloroform).

Reaction Scheme 22

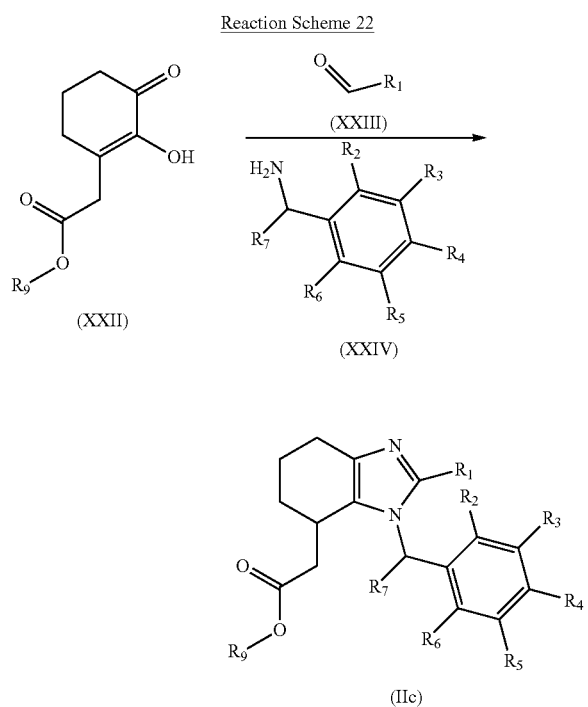

Compounds of the general formula (XXII) may be prepared from diones (XXV) (such as cyclohexane dione) according to reaction scheme 23 by treatment of (XXV) with two equivalents of a strong base (such as lithium diisopropylamide, generated from butyllithium and diisopropylamine) then reaction with an alpha-bromoacetate (XXVI) (such as ethyl bromoacetate) in a polar aprotic solvent (such as 2-methyl tetrahydrofuran). Isomerisation under acidic conditions (such as silica column chromatography) provides predominantly the enol isomer shown.

Reaction Scheme 23

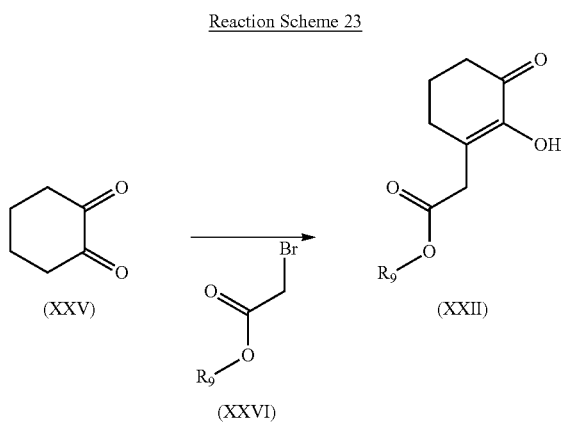

Compounds of the general formula (XIIIa) may also be prepared from (XXVII) according to reaction scheme 24 by treatment with a strong acid (such as TFA) in an appropriate solvent (such as dichloromethane)

Reaction Scheme 24

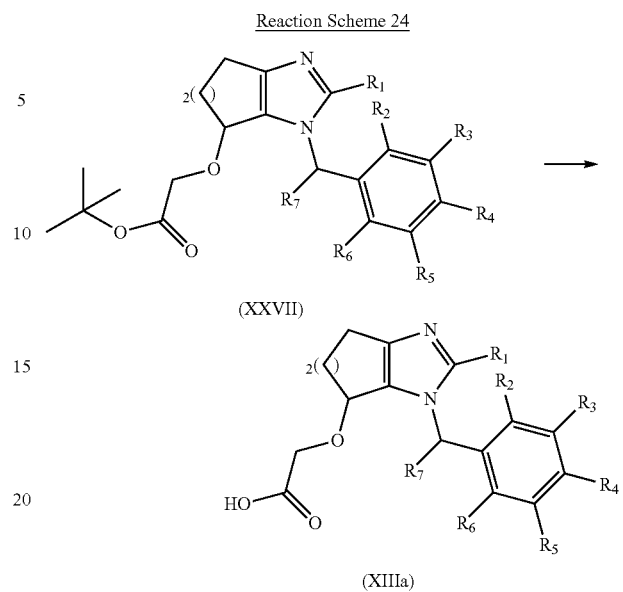

LCMS Analysis Conditions

The following conditions are representative of those used for the generation of analytical LCMS data.

1) Formic Acid Generic Analytical UPLC Open Access LC/MS (2 Minute Method)

The UPLC analysis was conducted on an Acquity UPLC BEH C18 column (2.1 mm×50 mm i.d. 1.7 μm packing diameter) at 40 degrees centigrade.

The solvents employed were:
A=0.1% v/v solution of Formic Acid in Water.
B=0.1% v/v solution of Formic Acid in Acetonitrile.
The gradient employed was:

| Time (min) | Flow Rate (ml/min) | % A | % B |
|---|---|---|---|
| 0 | 1 | 97 | 3 |
| 1.5 | 1 | 0 | 100 |
| 1.9 | 1 | 0 | 100 |
| 2.0 | 1 | 97 | 3 |

The UV detection was an averaged signal from wavelength of 210 nm to 350 nm and mass spectra were recorded on a mass spectrometer using alternate-scan positive and negative mode electrospray ionization.

2) Formic Acid Generic Analytical HPLC Open Access LC/MS (5 Minute Method)

The HPLC analysis was conducted on a Sunfire C18 column (30 mm×4.6 mm i.d. 3.5 μm packing diameter) at 30 degrees centigrade.

The solvents employed were:
A=0.1% v/v solution of Formic Acid in Water.
B=0.1% v/v solution of Formic Acid in Acetonitrile.
The gradient employed was:

| Time (min) | Flow Rate (ml/min) | % A | % B |
|---|---|---|---|
| 0 | 3 | 97 | 3 |
| 0.1 | 3 | 97 | 3 |
| 4.2 | 3 | 0 | 100 |

-continued

| Time (min) | Flow Rate (ml/min) | % A | % B |
|---|---|---|---|
| 4.8 | 3 | 0 | 100 |
| 4.9 | 3 | 97 | 3 |
| 5.0 | 3 | 97 | 3 |

The UV detection was an averaged signal from wavelength of 210 nm to 350 nm and mass spectra were recorded on a mass spectrometer using alternate-scan positive and negative mode electrospray ionization.

3) Trifluoroacetic Acid Generic Analytical HPLC Open Access LC/MS (5 Minute Method—TFA Modifier)

The HPLC analysis was conducted on a Sunfire C18 column (30 mm×4.6 mm i.d. 3.5 μm packing diameter) at 30 degrees centigrade.

The solvents employed were:
A=0.1% v/v solution of Trifluoroacetic Acid in Water.
B=0.1% v/v solution of Trifluoroacetic Acid in Acetonitrile.

The gradient employed was:

| Time (min) | Flow Rate (ml/min) | % A | % B |
|---|---|---|---|
| 0 | 3 | 97 | 3 |
| 0.1 | 3 | 97 | 3 |
| 4.2 | 3 | 0 | 100 |
| 4.8 | 3 | 0 | 100 |
| 4.9 | 3 | 97 | 3 |
| 5.0 | 3 | 97 | 3 |

The UV detection was an averaged signal from wavelength of 210 nm to 350 nm and mass spectra were recorded on a mass spectrometer using positive electrospray ionization.

4) High pH Generic Analytical HPLC Open Access LC/MS (5 Minute Method—High pH)

The HPLC analysis was conducted on an XBridge C18 column (50 mm×4.6 mm i.d. 3.5 μm packing diameter) at 30 degrees centigrade.

The solvents employed were:
A=10 mM Ammonium Bicarbonate in water adjusted to pH 10 with Ammonia solution.
B=Acetonitrile.

The gradient employed was:

| Time (min) | Flow Rate (ml/min) | % A | % B |
|---|---|---|---|
| 0 | 3 | 99 | 1 |
| 0.1 | 3 | 99 | 1 |
| 4.0 | 3 | 3 | 97 |
| 5.0 | 3 | 3 | 97 |

The UV detection was an averaged signal from wavelength of 210 nm to 350 nm and mass spectra were recorded on a mass spectrometer using alternate-scan positive and negative mode electrospray ionization.

MDAP Purification Conditions

Method A: Formic Acid Mass-Directed Autoprep (MDAP)

The HPLC analysis was conducted on a Sunfire C18 column (150 mm×30 mm i.d. 5 μm packing diameter) at ambient temperature.

The solvents employed were:
A=0.1% v/v solution of Formic Acid in Water.
B=0.1% v/v solution of Formic Acid in Acetonitrile.

The gradient was selected according to the analytical retention time.

The UV detection was an averaged signal from wavelength of 210 nm to 350 nm and mass spectra were recorded on a mass spectrometer using alternate-scan positive and negative mode electrospray ionization.

Method B: High pH Mass-Directed Autoprep (MDAP)

The HPLC analysis was conducted on an XBridge C18 column (150 mm×30 mm i.d. 5 μm packing diameter) at ambient temperature.

The solvents employed were:
A=10 mM Ammonium Bicarbonate in water adjusted to pH 10 with Ammonia solution.
B=Acetonitrile.

The gradient was selected according to the analytical retention time.

The UV detection was an averaged signal from wavelength of 210 nm to 350 nm and mass spectra were recorded on a mass spectrometer using alternate-scan positive and negative mode electrospray ionization.

Method C: Trifluoroacetic Acid Focused Mass-Directed Autoprep (MDAP)

The HPLC analysis was conducted on a Sunfire C18 column (150 mm×30 mm i.d. 5 μm packing diameter) at ambient temperature.

The solvents employed were:
A=0.1% v/v solution of Trifluoroacetic Acid in Water.
B=0.1% v/v solution of Trifluoroacetic Acid in Acetonitrile.

The gradient was selected according to the analytical retention time.

The UV detection was an averaged signal from wavelength of 210 nm to 350 nm and mass spectra were recorded on a mass spectrometer using positive electrospray ionization.

X-Ray Powder Diffraction (XRPD)

X-ray powder diffraction (XRPD) patterns were acquired on a PANalytical X'Pert Pro powder diffractometer, model PW3040/60, serial number DY1850 using an XCelerator detector. The acquisition conditions were: radiation: Cu Kα, generator tension: 40 kV, generator current: 45 mA, start angle: 2.0° 2θ, end angle: 40.0° 2θ, step size: 0.0167° 2θ, time per step: 31.75 seconds. The sample was prepared by mounting a few milligrams of sample on a Si wafer (zero background) plates, resulting in a thin layer of powder.

Differential Scanning Calorimetry (DSC)

The DSC thermogram of Example 40 was obtained using a Perkin Elmer Pyris 1 DSC, serial number 537N9062304. The sample was weighed into an aluminium pan, a pan lid placed on top and crimped. The experiment was conducted using a heating rate of 10 C min$^{-1}$. The data are illustrated in FIG. 3.

The DSC thermogram of Example 40 ($1^{st}$ Alternative Preparation) was obtained using a TA Q2000 calorimeter, serial number 1000-0126. The sample was weighed into an aluminium pan, a pan lid placed on top and lightly crimped without sealing the pan. The experiment was conducted using a heating rate of 10 C min$^{-1}$. The data are illustrated in FIG. 4.

ABBREVIATIONS gm=gram
DIAD=diisopropyl azodicaboxylate
tlc=thin-layer chromatography
SM=Starting Material
CV=Column Volumes
TBME=tert-Butyl methylether
TFA=Trifluoroacetic Acid SPE=Solid Phase Extraction
RM=Reaction Mixture
Temp.=Temperature
Sat.=Saturated
Aq.=Aqueous
EtOAc=Ethyl acetate
LiHMDS=Lithium hexamethyldisilazide
THF=Tetrahydrofuran
2methylTHF, 2MeTHF, methyl-THF, methyltetrahydrofuran=2-methyltetrahydrofuran
sol.=Solution
TMSCl=Trimethylsilylchloride
MDAP=Mass directed autopreparative high performance liquid chromatography
RT/rt=room temperature
DCM=dichloromethane
DP=desired product
Atm.=atmosphere
hr.=Hour
DMAP=4-N,N-dimethylaminopyridine
EDC=N'-(3-dimethylaminopropyl)-N-ethylcarbodiimide hydrochloride
SCX=strong cation exchange (sulfonic acid resin)
MeCN=ACN=acetonitrile
LiAlH=Lithium aluminium Hydride
Mesyl=methanesulfonyl
DMSO=dimethylsulfoxide
DCC=dicyclohexyl carbodiimide
MeOH=methanol Intermediate 1
2-(1-methylethyl)cyclohepta[d]imidazol-4(1H)-one

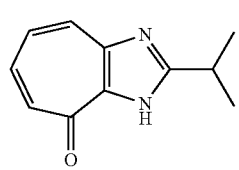

To a mixture of sodium hydroxide 30% in water (24 g) and toluene (30 mL), tropolone tosylate (5 g), isopropylcarbamidine hydrochloride (2.2 g) and tetrabutylammonium bromide (2.3 g) were added successively and the RM was stirred and heated at 30° C. for 1 hour. The reaction mixture was cooled down to room temp, diluted with an excess of sat. aq. NH4Cl solution and then extracted with EtOAc (3×40 ml). The aqueous phase was again extracted with EtOAc (3×50 ml). All the organics were combined, dried (hydrophobic frit) and concentrated under vacuum. The residue was purified by reverse phase chromatography using an acetonitrile-0.1% TFA:Water-0.1% TFA 5%-50% gradient and a 50%-95% gradient. The desired fractions were combined and concentrated under vacuum to yield the title compound (3.4 g). LC/MS MH+ 189, Rt 1.18 min (5 minute run)

Intermediate 2 2-(1-methylethyl)-5,6,7,8-tetrahydrocyclohepta[d]imidazol-4(1H)-one

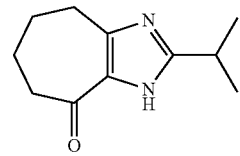

A solution of Intermediate 1 (3.4 g) in methanol (700 mL) was hydrogenated using the H-Cube (settings: room temp, 1.4 ml/min flow rate) and 10% Pd/C CatCart 30 as the catalyst. The solvent was concentrated under vacuum to give the title compound (3.5 g). LC/MS MH+ 193, Rt 0.42 min (2 minute run).

Intermediate 3 3-[(4-chlorophenyl)methyl]-2-(1-methylethyl)-5,6,7,8-tetrahydrocyclohepta[d]imidazol-4(3H)-one

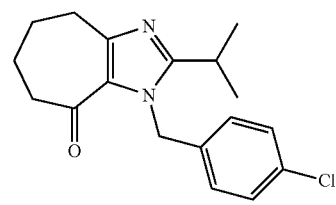 [SMILES: CC(C)c1nc2c(n1Cc1ccc(Cl)cc1)C(=O)CCCC2]

Tetrabutylammonium bromide (1.7 g) was added to a stirred mixture of Intermediate 2 (2 g) and 4-chlorobenzyl bromide (2.4 g) in sodium hydroxide 20% aq. (14.2 mL) and Toluene (7 mL). The RM was stirred at room temp under nitrogen atm for 3 hours. An excess of sat NH4Cl aq. solution was added and the mixture was extracted with EtOAc (3×30 ml). The organics were combined, dried (hydrophobic frit) and concentrated under vacuum. The residue was purified on silica using a cyclohexane:ethyl acetate 0-100% gradient. The desired fractions were combined and concentrated under vacuum to give the title compound (1.5 g). LC/MS MH+ 317, Rt 1.91 min (5 minute run).

Intermediate 4 Ethyl [3-[(4-chlorophenyl)methyl]-4-hydroxy-2-(1-methylethyl)-3,4,5,6,7,8-hexahydrocyclohepta[d]imidazol-4-yl]acetate

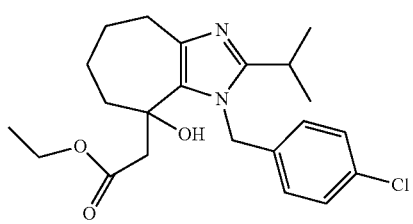 [SMILES: CCOC(=O)CC1(O)CCCCc2nc(C(C)C)n(Cc3ccc(Cl)cc3)c21]

Ethyl acetate (1.08 mL) in 2-methylTHF (1 ml) was added dropwise to a stirred solution of LiHMDS, 1M in THF (11.1 mL) cooled to −78° C. under nitrogen atm. The mixture was stirred at −78° C. under nitrogen for 30 mins. Then Intermediate 3 (700 mg) in 2-methylTHF (5 ml) was added dropwise. The RM was stirred at −78° C. under nitrogen for 4 hours. An excess of sat NH4Cl aq. sol. was added and the resulting suspension was warmed up to room temp and extracted with EtOAc (100 ml). The phases were separated and the aqueous layer was again extracted with EtOAc (50 ml), the phases were separated. The organics were combined, dried (hydrophobic frit) and concentrated under vacuum. The residue was purified on silica (100 g) using a dichloromethane:ethyl acetate 0-100% gradient. The desired fractions were combined and concentrated under vacuum to give the title compound (670 mg) LC/MS MH+ 405, Rt 0.89 min (2 minute run).

Intermediate 5 Ethyl [3-[(4-chlorophenyl)methyl]-2-(1-methylethyl)-3,4,5,6,7,8-hexahydrocyclohepta[d]imidazol-4-yl]acetate

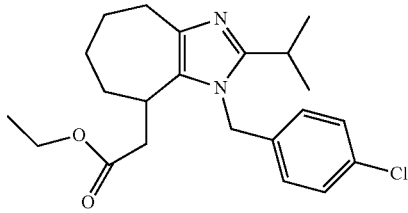 [SMILES: CCOC(=O)CC1CCCCc2nc(C(C)C)n(Cc3ccc(Cl)cc3)c21]

A mixture of TMSCI (0.846 mL) and sodium iodide (992 mg) in acetonitrile (12 ml) was added dropwise to a stirred suspension of Intermediate 4 (670 mg) in acetonitrile, cooled to −6° C. and keeping the temperature under 0° C. The RM was stirred at −6° C. and gradually warmed up to room temp overnight. The reaction mixture was partitioned between EtOAc (50 ml) and sat NaHCO3 aq. sol.: water (1:1, 50 ml). The two phases were separated and the aqueous phase was extracted again with EtOAc (50 ml). The phases were separated; the organic extracts were combined, dried (hydrophobic frit) and concentrated under vacuum. The residue was purified on silica using a cyclohexane:ethyl acetate 0-100% gradient. The desired fractions were combined and concentrated under vacuum to give the title compound (94 mg). LC/MS MH+ 389, Rt 1.32 min (2 minute run).

Example 1

[3-[(4-chlorophenyl)methyl]-2-(1-methylethyl)-3,4,5,6,7,8-hexahydrocyclohepta[d]imidazol-4-yl]acetic acid

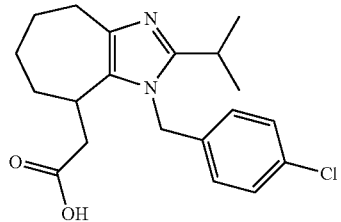 [SMILES: CC(C)c1nc2c(n1Cc1ccc(Cl)cc1)C(CC(=O)O)CCCC2]

Intermediate 5 (94 mg) was dissolved in methanol (2 ml) and treated with sodium hydroxide, 2 M aq. (2 ml). The RM was left in solution for 1 hour. The RM was concentrated under vacuum. The residue was purified by MDAP (Method A). The desired fractions were combined and concentrated under nitrogen blowdown to give the title compound (53 mg). LC/MS MH+ 361, Rt 1.63 min (5 minute run).

Intermediate 6 3-[(4-chlorophenyl)methyl]-2-(1-methylethyl)-3,4,5,6,7,8-hexahydrocyclohepta[d]imidazol-4-ol

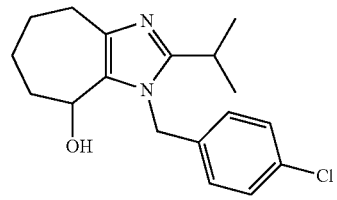 [SMILES: CC(C)c1nc2c(n1Cc1ccc(Cl)cc1)C(O)CCCC2]

Sodium borohydride (100 mg) was added to a stirred solution of Intermediate 3 (420 mg) in dichloromethane (3 ml) and methanol (3.00 ml). The reaction mixture was stirred for 1 hour. The reaction mixture was partitioned between EtOAc (50 ml) and water (30 ml). The two phases were separated and the aqueous phase was extracted again with EtOAc (30 ml). The phases were separated, the organic extracts were combined, dried (hydrophobic frit) and concentrated under vacuum to give the title compound (376 mg). LC/MS MH+ 319, Rt 0.77 min (2 minute run).

Example 2

{[3-[(3,4-chlorophenyl)methyl]-2-(1-methylethyl)-3,4,5,6,7,8-hexahydrocyclohepta[d]imidazol-4-yl]oxy}acetic acid ammonia salt

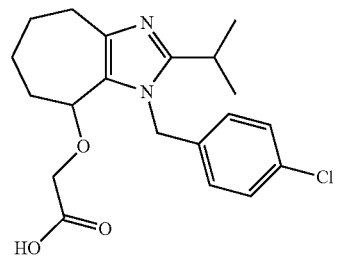 [SMILES: CC(C)c1nc2c(n1Cc1ccc(Cl)cc1)C(OCC(=O)O)CCCC2]

To a stirred solution of Intermediate 6 (90 mg) in anhydrous tetrahydrofuran (3 mL) at 0° C. under an atmosphere of nitrogen was added sodium hydride (15.81 mg, as a 60% by weight suspension on mineral oil) in one charge. The reaction was stirred at 0° C. for 30 min. To the reaction was added neat ethyl bromoacetate (0.041 mL) in one charge. The reaction was then gradually allowed to warm to ambient temperature under an atmosphere of nitrogen overnight. The RM was concentrated under vacuum and the residue dissolved in MDAP (method B). The desired fractions were combined and concentrated under nitrogen blowdown to give the title compound. LC/MS MH+ 377, Rt 1.97 min (5 minute run).

Intermediate 7 3-[(3,4-dichlorophenyl)methyl]-2-(1-methylethyl)-5,6,7,8-tetrahydrocyclohepta[d]imidazol-4(3H)-one

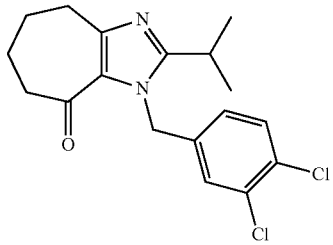 [SMILES: CC(C)c1nc2c(n1Cc1ccc(Cl)c(Cl)c1)C(=O)CCCC2]

Tetrabutylammonium bromide (419 mg) was added to a stirred mixture of Intermediate 2 (500 mg, 2.60 mmol) and 3,4-dichlorobenzylbromide (624 mg) in sodium hydroxide 20% aq (3.50 mL) and Toluene (9 mL). The RM was stirred at 30° C. under nitrogen atm for 3 hours. An excess of sat NH4Cl aq solution was added and the mixture was extracted with EtOAc (3×30 ml). The organics were combined, dried (hydrophobic frit) and concentrated under vacuum. The residue was purified on silica using a cyclohexane:ethyl acetate 0-100% gradient. The desired fractions were combined and concentrated under vacuum to give the title compound (630 mg). LC/MS MH+ 351/353, Rt 3.16 min (5 minute run).

Intermediate 8 3-[(3,4-dichlorophenyl)methyl]-2-(1-methylethyl)-3,4,5,6,7,8-hexahydrocyclohepta[d]imidazol-4-ol

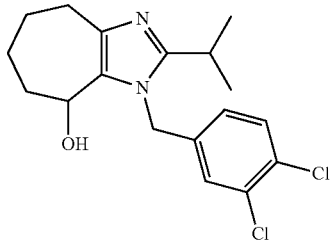 [SMILES: CC(C)c1nc2c(n1Cc1ccc(Cl)c(Cl)c1)C(O)CCCC2]

Sodium borohydride (204 mg) was added to a stirred solution of Intermediate 7 (630 mg) in dichloromethane (2 mL) and methanol (2 mL). The reaction mixture was stirred for 3 hours. The reaction mixture was partitioned between EtOAc (50 ml) and water (30 ml). The two phases were separated and the aqueous phase was extracted again with EtOAc (30 ml). The phases were separated; the organic extracts were combined, dried (hydrophobic frit) and concentrated under vacuum to give the title compound (600 mg). LC/MS MH+ 353/355, Rt 1.13 min (2 minute run).

Intermediate 8 (1st Alternative Preparation) 3-[(3,4-dichlorophenyl)methyl]-2-(1-methylethyl)-3,4,5,6,7,8-hexahydrocyclohepta[d]imidazol-4-ol

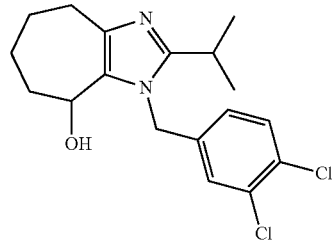 [SMILES: CC(C)c1nc2c(n1Cc1ccc(Cl)c(Cl)c1)C(O)CCCC2]

Sodium borohydride (0.218 g) was added to a solution of 3-[(3,4-dichlorophenyl)methyl]-2-(1-methylethyl)-5,6,7,8-tetrahydrocyclohepta[d]imidazol-4(3H)-one (prepared by a similar method to that provided for Intermediate 7) (1.69 g) in Dichloromethane (DCM) (10.8 mL) and Methanol (10.80 mL). After 60 minutes stirring LCMS showed around >90% conversion. The reaction was quenched with 100 mL of water, then the product was extracted in EtOAc (100 mL). The organic layer was concentrated in vacuo. LC/MS MH+ 353, Rt 2.02 mins (5 min run, TFA buffer). The enantiomers of this material were separated on Chiralpack AD eluting with a heptane/ethanol gradient and are reported in order of elution.

Intermediate 72 3-[(3,4-dichlorophenyl)methyl]-2-(1-methylethyl)-3,4,5,6,7,8-hexahydrocyclohepta[d]imidazol-4-ol (Isomer 1)

643 mg, LC/MS MH+ 353, Rt 1.86 mins (5 min run)

Intermediate 73 3-[(3,4-dichlorophenyl)methyl]-2-(1-methylethyl)-3,4,5,6,7,8-hexahydrocyclohepta[d]imidazol-4-ol (Isomer 2)

714 mg LC/MS MH+ 353, Rt 2.00 mins (5 min run)

Intermediate 9 Triethyl [3-[(3,4-dichlorophenyl)methyl]-2-(1-methylethyl)-3,4,5,6,7,8-hexahydrocyclohepta[d]imidazol-4-yl]methanetricarboxylate

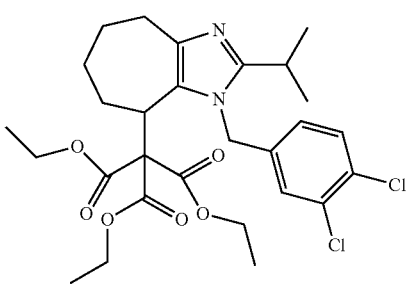 [SMILES: CCOC(=O)C(C(=O)OCC)(C(=O)OCC)C1CCCCc2nc(C(C)C)n(Cc3ccc(Cl)c(Cl)c3)c21]

To a suspension of Intermediate 8 (270 mg) and triethylmethanetricarboxylate (0.324 ml) in toluene (4 ml) and methyltetrahydrofuran (4.00 ml), stirred at RT under an inert atmosphere of nitrogen, was added trimethylphosphine, 1M in toluene (1.529 ml). The resulting solution was cooled to −78°

C. and diisopropyl azodicarboxylate (0.301 ml) was added dropwise via syringe and the reaction was stirred at −78° C. for 45 mins. The reaction mixture was removed from the cold bath and allowed to warm to RT and stirred under N2 atmosphere overnight. Reaction mixture concentrated slowly in vacuo using the rotavapor with the water bath at 50° C. The residue was taken up in DCM (20 ml) and washed with water (20 mL). The 2 phases were separated; the aqueous was extracted again with DCM (20 mL). The organic extracts were combined, dried (hydrophobic frit) and concentrated under vacuum. The residue was purified by silica using a cyclohexane:ethyl acetate 0-100% gradient. The desired fractions were combined and concentrated under vacuum to give the title compound (435 mg).

LC/MS MH+ 567, Rt 3.77 min (5 minute run).

Example 3

[3-[(3,4-dichlorophenyl)methyl]-2-(1-methylethyl)-3,4,5,6,7,8-hexahydrocyclohepta[d]imidazol-4-yl] acetic acid ammonia salt

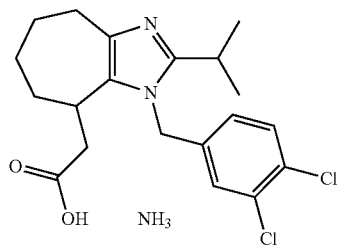

A mixture of Intermediate 9 (435 mg) and Sodium hydroxide, 2M aq (2.3 mL) in Ethanol (6 mL) was stirred at RT for 5 mins and then at 80° C. for 3 hr. The solvent was concentrated under vacuum, the residue suspended in acetic acid (6.00 mL) and heated at 120° C. for 2 hr. The solvent was removed under vacuum and the residue was purified by reverse phase chromatography using acetonitrile water with an ammonium carbonate modifier. The desired fractions were combined and concentrated under vacuum to give a white solid (210 mg). LC/MS MH+ 395, Rt 2.10 min (5 minute run).

Intermediate 10 Phenylmethyl [3-[(3,4-dichlorophenyl)methyl]-2-(1-methylethyl)-3,4,5,6,7,8-hexahydrocyclohepta[d]imidazol-4-yl]acetate

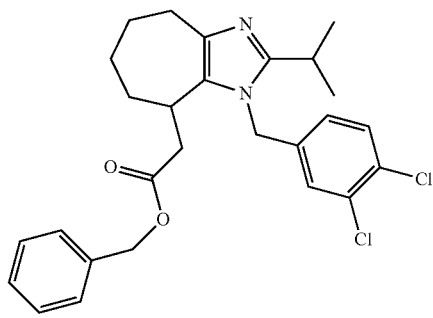 [SMILES: CC(C)c1nc2c(n1Cc1ccc(Cl)c(Cl)c1)C(CC(=O)OCc1ccccc1)CCCC2]

To a stirred suspension of Example 3 (180 mg) in dichloromethane (5 mL) at 0° C. was added benzyl alcohol (0.095 mL), 4-dimethylamino pyridine (10 mg) and N'-(3-dimethylaminopropyl)-N-ethylcarbodiimide hydrochloride (100 mg) sequentially. The reaction was stirred at 0° C. under an atmosphere for 1.5 hr. The reaction was allowed to achieve ambient temperature and stirred for a further 18 hr. The reaction mixture was partitioned between dichloromethane (10 mL) and water (10 mL). The aqueous phase was back extracted with dichloromethane (10 mL). The combined organics were dried (hydrophobic frit) and concentrated in vacuo to give 274 mg of product. The sample was purified on silica using 0-100% ethyl acetate-cyclohexane. The appropriate fractions were combined and evaporated in vacuo to give the title compound (159 mg). LC/MS MH+ 485, 487, Rt 2.28 min (5 minute run).

The enantiomers were separated on a 5 cm×20 cm Chiralcel OJ (20 um) column (3 injections) eluting with 5% EtOH/Heptane. The compounds are listed in the order they eluted from the column.

Intermediate 11 Phenylmethyl [3-[(3,4-dichlorophenyl)methyl]-2-(1-methylethyl)-3,4,5,6,7,8-hexahydrocyclohepta[d]imidazol-4-yl]acetate (isomer 1)

66 mg LC/MS MH+ 485, 487, Rt 2.29 min (5 minute run).

Intermediate 12 Phenylmethyl [3-[(3,4-dichlorophenyl)methyl]-2-(1-methylethyl)-3,4,5,6,7,8-hexahydrocyclohepta[d]imidazol-4-yl]acetate isomer (isomer 2)

66 mg. LC/MS MH+ 485, 487, Rt 2.30 min (5 minute run).

Example 4

(+)-[3-[(3,4-dichlorophenyl)methyl]-2-(1-methylethyl)-3,4,5,6,7,8-hexahydrocyclohepta[d]imidazol-4-yl]acetic acid (isomer 1)

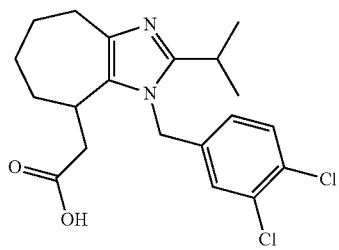 [SMILES: CC(C)c1nc2c(n1Cc1ccc(Cl)c(Cl)c1)C(CC(=O)O)CCCC2]

To a stirred solution of Intermediate 11 (isomer 1) (66 mg) in tetrahydrofuran (3 mL) at ambient temperature was added 2M aqueous sodium hydroxide (0.5 mL). The reaction was stirred at ambient temperature for 16 hr. A further aliquot of 2M aqueous sodium hydroxide (1 mL) was added and the reaction stirred for a further 24 hr. The reaction was neutralised using 2M aqueous hydrochloric acid and concentrated in vacuo to give a white solid. The solid was taken up in 1:1 acetonitrile:water and purified by SPE on sulphonic acid 10 g (SCX) washing with 1:1 acetonitrile:water and eluting with 2M ammonia in methanol. The product came through in the acetonitrile:water wash and this fraction was concentrated in vacuo to give a white solid (product plus salts). The solid was suspended in ethyl acetate and heated to reflux for 30 mins. The mixture was filtered hot and the filtrated concentrated in vacuo to give 32 mg of the title compound.

LC/MS MH+ 395, 397, Rt 1.78 min (5 minute run). [α]$_D$=+10.4 (24° C., 1:1 methanol:DCM). ¹H NMR (DMSO-d6) δ 1.03 (d, 3H), 1.09 (d, 3H), 1.25-1.45 (m, 4H), 1.66-1.88 (m, 4H), 2.23 (dd, 1H), 2.44 (dd, 1H), 2.58 (m, 1H), 2.69 (m, 1H), 2.96 (m, 1H), 3.03 (m, 1H), 5.24 (d, 1H—'roofed' AB system), 5.29 (d, 1H—'roofed' AB system), 6.83 (dd, 1H), 7.23 (br.s, 1H), 7.63 (d, 1H), 12.2 (br.s, 1H).

Example 5

[3-[(3,4-dichlorophenyl)methyl]-2-(1-methylethyl)-3,4,5,6,7,8-hexahydrocyclohepta[d]imidazol-4-yl]acetic acid (isomer 2)

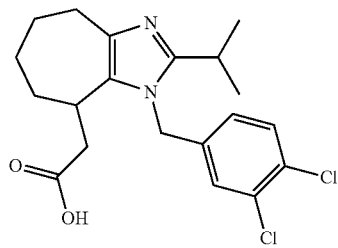 [SMILES: CC(C)c1nc2c(n1Cc1ccc(Cl)c(Cl)c1)C(CC(=O)O)CCCC2]

Prepared in exactly the same manner as Example 4 from Intermediate 12 (isomer 2) (66 mg) to provide 30 mg of the title compound.
LC/MS MH+ 395, 397, Rt 1.78 min (5 minute run).

Intermediate 63 2-(1,1-dimethylethyl)cyclohepta[d]imidazol-4(1H)-one

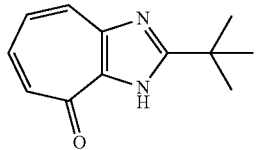

To a mixture of sodium hydroxide 30% in water (12.06 g) and toluene (20 mL), tropolone tosylate (2.5 g), tert-butylcarbamidine hydrochloride (1.236 g) and tetrabutylammonium bromide (1.167 g) were added successively and the RM was stirred and heated at 30° C. for 1 hour. The reaction mixture was cooled down to room temp, diluted with an excess of sat. aq. NH4Cl solution and then extracted with EtOAc (3×50 ml). The combined organics were dried (hydrophobic frit) and concentrated under vacuum. The residue was purified by reverse phase chromatography using an acetonitrile-0.1% TFA:water-0.1% TFA (5%-95% gross gradient). The desired fractions were combined and concentrated under vacuum to yield the title compound (1.9 g). LC/MS MH+ 203, Rt 0.62 min (2 minute run).

Intermediate 13 2-(1,1-dimethylethyl)-5,6,7,8-tetrahydrocyclohepta[d]imidazol-4(1H)-one

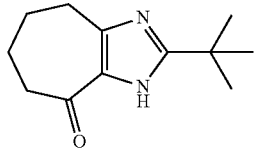

A solution of Intermediate 63 (1.9 g) in methanol (400 mL) was hydrogenated using the H-Cube (settings: room temp, 1.3 ml/min flow rate) and 10% Pd/C CatCart 30 as the catalyst. The solvent was concentrated under vacuum to give the title compound (1.7 g). LC/MS MH+ 207 Rt 0.75 min (5 minute run).

Intermediate 14 3-[(4-chlorophenyl)methyl]-2-(1,1-dimethylethyl)-5,6,7,8-tetrahydrocyclohepta[d]imidazol-4(3H)-one

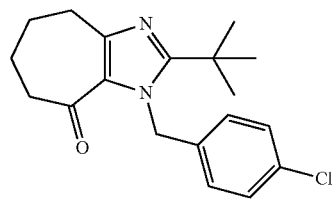 [SMILES: CC(C)(C)c1nc2c(n1Cc1ccc(Cl)cc1)C(=O)CCCC2]

Tetrabutylammonium bromide (1.33 g) was added to a stirred mixture of Intermediate 13 (1.7 g), 4-chlorobenzyl bromide (1.86 g) in sodium hydroxide 20% aq. (12 mL) and toluene (6 mL). The RM was stirred at room temp under nitrogen atm for 3 hours. An excess of sat. NH4Cl aq. solution was added and the mixture was extracted with EtOAc (3×30 ml). The organics were combined, dried (hydrophobic frit) and concentrated under vacuum. The residue was purified on silica using a cyclohexane:ethyl acetate 0-100% gradient. The desired fractions were combined and concentrated under vacuum to give crude material. It was purified by reverse phase chromatography using an acetonitrile-0.1% NH3:water—with an amonium carbonate buffer modifier (pH=10) 5%-95% gradient. The desired fractions were combined and concentrated under vacuum to yield the title compound (650 mg). LC/MS MH+ 331 Rt 2.04 min (5 minute run).

Intermediate 15 Ethyl [3-[(4-chlorophenyl)methyl]-2-(1,1-dimethylethyl)-4-hydroxy-3,4,5,6,7,8-hexahydrocyclohepta[d]imidazol-4-yl]acetate

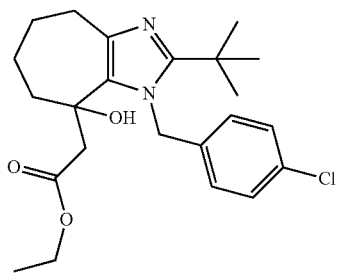 [SMILES: CCOC(=O)CC1(O)CCCCc2nc(C(C)(C)C)n(Cc3ccc(Cl)cc3)c21]

Ethyl acetate (0.695 mL) was added dropwise to a stirred solution of LiHMDS, 1M in THF (7.10 ml) cooled to −78° C. under nitrogen atmosphere. The mixture was stirred at −78° C. for 30 minutes. Intermediate 14 was dissolved in THF (3 ml) and added dropwise. The RM was stirred at −78° C. under nitrogen for 2 hours. An excess of sat. NH4Cl aq. sol. added and the resulting suspension warmed up to room temp and extracted with EtOAc (100 ml). The phases were separated and the aqueous layer was again extracted with EtOAc (50 ml), the phases were separated. The organics were combined, dried (hydrophobic frit) and concentrated under vacuum. The residue was purified on silica using a Dichloromethane:Ethyl acetate 0-100% gradient. The desired fractions were combined and concentrated under vacuum to give the title compound (420 mg). LC/MS MH$^+$419, Rt 1.93 min (5 minute run).

Intermediate 16 ethyl [3-[(4-chlorophenyl)methyl]-2-(1,1-dimethylethyl)-3,4,5,6,7,8-hexahydrocyclohepta[d]imidazol-4-yl]acetate

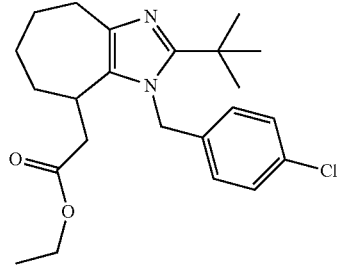 [SMILES: CCOC(=O)CC1CCCCc2nc(C(C)(C)C)n(Cc3ccc(Cl)cc3)c21]

A mixture of TMSCl (0.513 mL), sodium iodide (601 mg) and acetonitrile (9 ml) was added to a stirred suspension of Intermediate 15 (420 mg) in acetonitrile (3 ml). The RM was stirred at room temp under nitrogen overnight. The reaction mixture was partitioned between EtOAc (50 ml) and sat. NaHCO3 aq. sol.: water (1:1, 50 ml). The two phases were separated and the aqueous phase was extracted again with EtOAc (50 ml). The phases were separated; the organic extracts were combined, dried (hydrophobic frit) and concentrated under vacuum. The residue was purified by reverse phase chromatography using an acetonitrile—0.1% NH3:water—with an amonium carbonate buffer modifier (pH=10) 5%-35% gradient. The desired fractions were combined and concentrated under vacuum. The mixture was purified by MDAP (Method B). The desired fractions were combined and concentrated under nitrogen blowdown to give the title compound (22 mg). LC/MS MH$^+$ 403 Rt 1.09 min (2 minute run).

Example 6

[3-[(4-chlorophenyl)methyl]-2-(1,1-dimethylethyl)-3,4,5,6,7,8-hexahydrocyclohepta[d]imidazol-4-yl] acetic acid

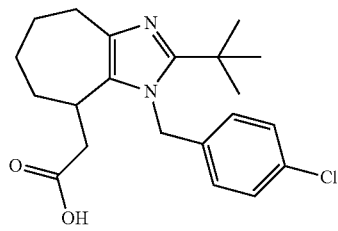 [SMILES: CC(C)(C)c1nc2c(n1Cc1ccc(Cl)cc1)C(CC(=O)O)CCCC2]

Intermediate 16 (22 mg) was dissolved in Methanol (1 ml) and treated with sodium hydroxide, 2M aq. (1 mL). The RM was left in solution for 1 hour. The residue was purified by MDAP (Method A). The desired fractions were combined and concentrated under nitrogen blowdown to give the title compound (17 mg). LC/MS MH$^+$ 375, Rt 1.72 min (5 minute run).

Intermediate 17 2-(1-methylethyl)-5,6-dihydrocyclopenta[d]imidazol-4(1H)-one

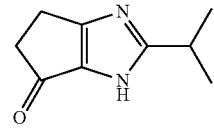

A mixture of 2-methylpropanimidamide hydrochloride (0.770 g), 2-bromo-3-(methyloxy)-2-cyclopenten-1-one (1 g) and potassium carbonate (2.17 g) in N,N-dimethylformamide (15 mL) were heated at 100° C. for 4.5 hr and then heated at 110° C. for 1 hour. The reaction mixture was cooled down to room temperature and dichloromethane was added. The white suspension (potassium carbonate) was filtered off and the filtrate concentrated under vacuum. The residue was purified by reverse phase chromatography using an acetonitrile—0.1% NH3:water—with an ammonium carbonate buffer modifier using a 5%-95% gradient. The desired fractions were combined and concentrated under vacuum to yield the title compound (531 mg). LC/MS MH$^+$ 165, Rt 0.36 min (2 minute run).

Intermediate 18 3-[(4-chlorophenyl)methyl]-2-(1-methylethyl)-5,6-dihydrocyclopenta[d]imidazol-4 (3H)-one

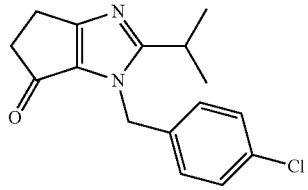 [SMILES: CC(C)c1nc2c(n1Cc1ccc(Cl)cc1)C(=O)CC2]

Tetrabutylammonium bromide (785 mg) was added to a stirred mixture of Intermediate 17 (800 mg), 4-chlorobenzyl bromide (1101 mg) in sodium hydroxide 20% aq. (9 mL) and toluene (20 mL). The RM was stirred at room temp under nitrogen atm. for 1.5 hours. Sat. NH4Cl aq solution (50 mL) was added and the mixture was extracted with EtOAc (2×50 ml). The organics were combined, dried (hydrophobic frit) and concentrated under vacuum. The residue was purified on silica using a cyclohexane:ethyl acetate 0-100% gradient. The desired fractions were combined and concentrated under vacuum to give the title compound (467 mg). LC/MS MH$^+$ 289, Rt 0.92 min (2 minute run).

Intermediate 19 3-[(4-chlorophenyl)methyl]-2-(1-methylethyl)-3,4,5,6-tetrahydrocyclopenta[d]imidazol-4-ol

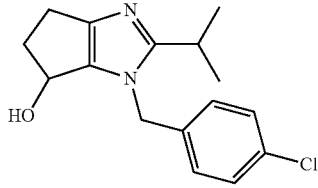 [SMILES: CC(C)c1nc2c(n1Cc1ccc(Cl)cc1)C(O)CC2]

Sodium borohydride (76 mg) was added to a stirred solution of Intermediate 18 (290 mg) in dichloromethane (3 ml) and methanol (3 ml). The reaction mixture was stirred for 3 hours. The reaction mixture was concentrated under vacuum, partitioned between EtOAc (20 ml) and water (15 ml). The two phases were separated and the aqueous phase was extracted again with EtOAc (2×10 ml). The phases were separated, the organic extracts were combined, dried (hydrophobic frit) and concentrated under vacuum to give the title compound (272 mg). LC/MS MH+ 291, Rt 1.35 min (5 minute run).

Intermediate 20 Triethyl [3-[(4-chlorophenyl)methyl]-2-(1-methylethyl)-3,4,5,6-tetrahydrocyclopenta[d]imidazol-4-yl]methanetricarboxylate

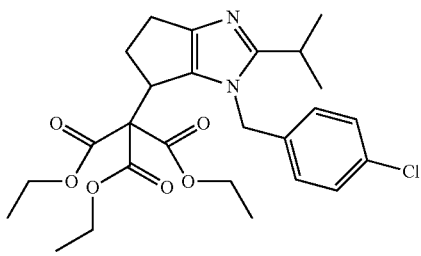 [SMILES: CCOC(=O)C(C(=O)OCC)(C(=O)OCC)C1CCc2nc(C(C)C)n(Cc3ccc(Cl)cc3)c21]

To a solution of Intermediate 19 (50 mg) and triethylmethanetricarboxylate (0.073 ml) in toluene (1.5 ml) and tetrahydrofuran (1.5 ml), stirred at RT under an inert atmosphere of nitrogen, was added trimethylphosphine, 1M in toluene (0.344 ml). The resulting solution was cooled to −78° C. and diisopropyl azodicarboxylate (0.068 ml) was added dropwise via syringe and the reaction was stirred at −78° C. for 45 mins. The reaction mixture was removed from the cold bath and allowed to warm to RT and stirred under N2 atmosphere overnight. Reaction mixture concentrated in vacuo. The residue was taken up in DCM (20 ml) and washed with water (20 mL). The 2 phases were separated, the organic extract was dried (hydrophobic frit) and concentrated under vacuum. The residue was purified on silica using a cyclohexane:ethyl acetate 0-100% gradient. The desired fractions were combined and concentrated under vacuum to give the title compound (48 mg). LC/MS MH+ 505, Rt 3.41 min (5 minute run).

Example 7

[3-[(4-chlorophenyl)methyl]-2-(1-methylethyl)-3,4,5,6-tetrahydrocyclopenta[d]imidazol-4-yl]acetic acid ammonia salt

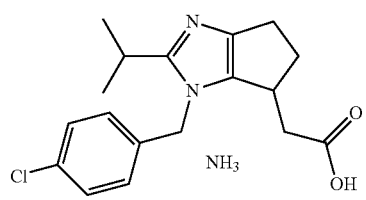

Intermediate 20 (50 mg) was dissolved in methanol (3 ml) and the resulting soln. was treated with sodium hydroxide, 3M aq. (1 ml). The resulting suspension was heated to reflux for 4 hr. The reaction mixture was allowed to cool and concentrated in vacuo. The crude residue was taken up in acetic acid (10 ml) and heated to reflux for 2 h.

Reaction mixture concentrated in vacuo and the residue partitioned between DCM (10 mL) and 2M aq. HCl (5 mL). The 2 phases were separated, the aqueous phase was extracted with more DCM (2×10 mL). The organic extracts were combined, dried (hydrophobic frit) and concentrated under vacuum. The aqueous phase was combined with the organic residue, concentrated under vacuum and the residue was purified by MDAP (Method B). The solvent was evaporated in vacuo to give the required product (16 mg). LC/MS MH+ 333, Rt 1.84 min (5 minute run).

Example 8

{[3-[(4-chlorophenyl)methyl]-2-(1-methylethyl)-3,4,5,6-tetrahydrocyclopenta[d]imidazol-4-yl]oxy}acetic acid ammonia salt

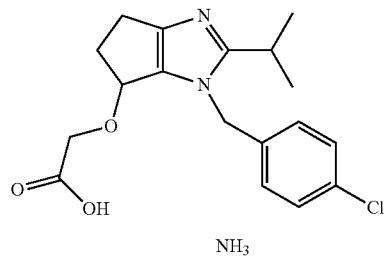

To a stirred solution of Intermediate 19 (210 mg) in anhydrous N,N-dimethylformamide (3 mL) at 0° C. under an atmosphere of nitrogen was added sodium hydride (40.4 mg) as a 60% by weight suspension on mineral oil in one charge. The reaction mixture was stirred at 0° C. for 30 min. To the reaction mixture was added neat ethyl bromoacetate (0.105 mL) in one charge the reaction was then left stirring at 0° C. for 1 hour and then warmed to ambient temperature and left stirring under nitrogen atm. for 1 hour. The RM was cooled down to 0° C., sodium hydride (40.4 mg) as a 60% by weight suspension on mineral oil was then added in one charge. The reaction mixture was stirred at 0° C. for 30 min. To the reaction mixture was again added neat ethyl bromoacetate (0.105 mL) in one charge the reaction was gradually warmed to ambient temperature under nitrogen atm. overnight. The RM was concentrated under vacuum. The residue was purified by MDAP (Method B). The desired fractions were combined and concentrated under nitrogen blowdown to give the title compound (61 mg).

LC/MS MH+ 349, Rt 1.83 min (5 minute run).

Intermediate 21 3-[(3,4-dichlorophenyl)methyl]-2-(1-methylethyl)-5,6-dihydrocyclopenta[d]imidazol-4(3H)-one

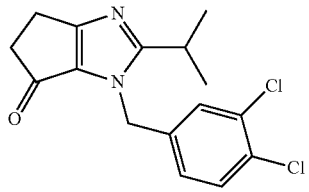 [SMILES: CC(C)c1nc2c(n1Cc1ccc(Cl)c(Cl)c1)C(=O)CC2]

Tetrabutylammonium bromide (520 mg, 1.614 mmol) was added to a stirred mixture of Intermediate 17 (530 mg) and 4-(bromomethyl)-1,2-dichlorobenzene (852 mg) in sodium hydroxide 20% aq. (5.16 mL) and Toluene (6 mL). The RM was stirred at room temp for 3 hours. An excess of sat NH4Cl aq. solution was added and the mixture was extracted with EtOAc (3×30 ml). The organics were combined, dried (hydrophobic frit) and concentrated under vacuum. The residue was purified on silica (100 g) using a cyclohexane:ethyl acetate 0-100% gradient. The desired fractions were combined and concentrated under vacuum to give the title compound (660 mg).

LC/MS MH$^+$ 323, 325, Rt 2.45 min (5 minute run).

Intermediate 22 3-[(3,4-dichlorophenyl)methyl]-2-(1-methylethyl)-3,4,5,6-tetrahydrocyclopenta[d]imidazol-4-ol

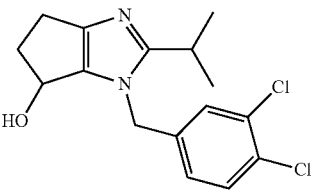 [SMILES: CC(C)c1nc2c(n1Cc1ccc(Cl)c(Cl)c1)C(O)CC2]

Sodium borohydride (155 mg) was added to a stirred solution of Intermediate 21 (660 mg) in dichloromethane (2 mL) and methanol (2 mL). The reaction mixture was stirred for 2.5 hours. More sodium borohydride (155 mg) was added. The RM was left stirring at room temp. under nitrogen for 1 hour. The reaction mixture was partitioned between EtOAc (50 ml) and water (30 ml). The two phases were separated and the aqueous phase was extracted again with EtOAc (30 ml). The phases were separated; the organic extracts were combined, dried (hydrophobic frit) and concentrated under vacuum to give the title compound (660 mg). LC/MS MH$^+$ 325, 327, Rt 1.63 min (5 minute run).

Intermediate 68 Triethyl [3-[(3,4-dichlorophenyl)methyl]-2-(1-methylethyl)-3,4,5,6-tetrahydrocyclopenta[d]imidazol-4-yl]methanetricarboxylate

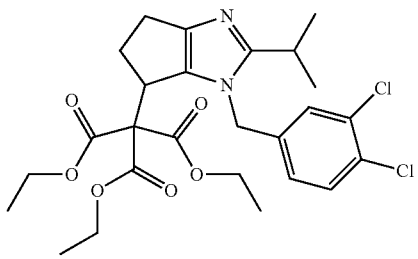 [SMILES: CCOC(=O)C(C(=O)OCC)(C(=O)OCC)C1CCc2nc(C(C)C)n(Cc3ccc(Cl)c(Cl)c3)c21]

To a solution of Intermediate 22 (660 mg) and triethylmethanetricarboxylate (0.86 ml) in toluene (1.5 ml) and tetrahydrofuran (1.5 ml), stirred at RT under an inert atmosphere of nitrogen, was added dropwise trimethylphosphine, 1M in toluene (4.06 ml). The resulting solution was cooled to −78° C. and diisopropyl azodicarboxylate (0.799 ml) was added dropwise via syringe and the reaction was stirred at −78° C. for 2 hours. The reaction mixture was removed from the cold bath and allowed to warm to RT and stirred under N2 atmosphere for 30 mins. Reaction mixture concentrated in vacuo. The residue was taken up in DCM (40 ml) and washed with water (40 mL). The 2 phases were separated; the organic extract was dried (hydrophobic frit) and concentrated under vacuum. The residue was purified on silica using a cyclohexane:ethyl acetate 0-100% gradient. The desired fractions were combined and concentrated under vacuum to give the title compound (750 mg). LC/MS MH$^+$ 539, 541, Rt 2.19 min (5 minute run).

Example 9

[3-[(3,4-dichlorophenyl)methyl]-2-(1-methylethyl)-3,4,5,6-tetrahydrocyclopenta[d]imidazol-4-yl]acetic acid ammonia salt

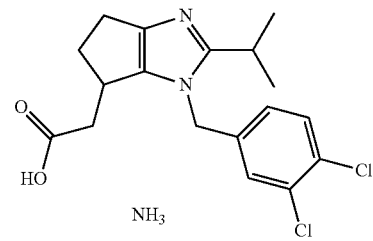

Intermediate 68 (750 mg) was dissolved in methanol (5 ml) and the resulting soln. was treated with sodium hydroxide, 3M aq. (3 ml). The resulting suspension was heated to reflux for 2 hr. The reaction mixture was allowed to cool to room temp and concentrated in vacuo.

The crude residue was taken up in acetic acid (15 ml) and heated to reflux for 2 hr. The RM was concentrated under vacuum. The residue was purified by reverse phase chromatography using an acetonitrile—0.1% NH3:Water—with an amonium carbonate buffer modifier (pH=10) 5%-95% gradient. The desired fractions were combined and concentrated under vacuum to yield the title compound (501 mg). LC/MS MH$^+$ 367, 369, Rt 1.61 min (5 minute run).

Intermediate 23 Phenylmethyl [3-[(3,4-dichlorophenyl)methyl]-2-(1-methylethyl)-3,4,5,6-tetrahydrocyclopenta[d]imidazol-4-yl]acetate

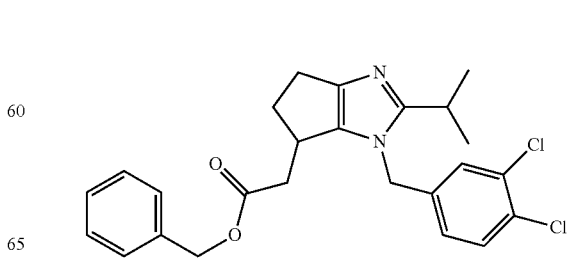

Benzyl alcohol (0.193 mL), DMAP (16.96 mg) and EDC (195 mgl) were successively added to a stirring solution of Example 9 (340 mg) in dichloromethane (5 mL) cooled at 0° C. under nitrogen. The RM was warmed to room temp and left stirring under nitrogen atm. overnight. The reaction mixture was partitioned between dichloromethane (10 mL) and water (10 mL). The aqueous phase was again extracted with DCM (20 ml). The 2 phases were separated; the organic extract was dried (hydrophobic frit) and concentrated under vacuum. The residue was purified on silica using a cyclohexane:ethyl acetate 0-100% gradient. The desired fractions were combined and concentrated under vacuum to give the title compound (380 mg). LC/MS MH+ 457, 459, Rt 3.55 min (5 minute run).

The enantiomers were separated on a 5 cm×20 cm Chiralcel OJ (20 um) column (4 injections) eluting with 10% EtOH/Heptane. The compounds are listed in the order they eluted from the column.

Intermediate 24 Phenylmethyl [3-[(3,4-dichlorophenyl)methyl]-2-(1-methylethyl)-3,4,5,6-tetrahydrocyclopenta[d]imidazol-4-yl]acetate (Isomer 1)

156 mg. LC/MS MH+ 457, Rt 2.09 min (5 minute run).

Intermediate 25 Phenylmethyl [3-[(3,4-dichlorophenyl)methyl]-2-(1-methylethyl)-3,4,5,6-tetrahydrocyclopenta[d]imidazol-4-yl]acetate (Isomer 2)

152 mg. LC/MS MH+ 457, Rt 2.09 min (5 minute run).

Example 10

(+)-[3-[(3,4-dichlorophenyl)methyl]-2-(1-methylethyl)-3,4,5,6-tetrahydrocyclopenta[d]imidazol-4-yl] acetic acid ammonia salt (Isomer 1)

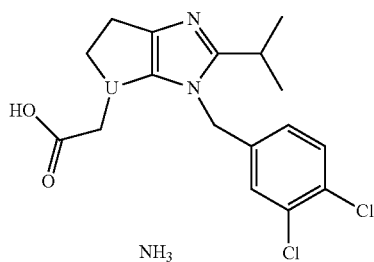

To a stirred solution of Intermediate 24 (isomer 1) (145 mg) in tetrahydrofuran (3 mL) at ambient temperature was added neat 2M aqueous sodium hydroxide (1 mL) in one charge. The reaction was stirred for 24 h. The reaction was adjusted to pH 6-7 with 2N aqueous hydrochloric acid (ca. 1 mL). The reaction was concentrated in vacuo. The residue was taken up in 1:1 acetonitrile: water and purified by SCX (20 g) washing with 1:1 acetonitrile:water and eluting with 2M ammonia in methanol. The appropriate fractions were combined and concentrated in vacuo to give the title compound (96 mg). LC/MS MH+ 367, 369, Rt 1.59 min (5 minute run). [α]$_D$=+25.9° (24° C., 1:1 methanol:DCM). $^1$H NMR δ 1.07 (d, 3H), 1.10 (d, 3H), 1.97 (m, 1H), 2.08 (dd, 1H), 2.39 (m, 2H), 2.55 (m, 2H), 2.87 (pent., 1H), 3.18 (m, 1H), 5.14 (d, 1H), 5.22 (d, 1H), 6.89 (dd, 1H), 7.30 (d, 1H), 7.63 (d, 1H).

Example 11

[3-[(3,4-dichlorophenyl)methyl]-2-(1-methylethyl)-3,4,5,6-tetrahydrocyclopenta[d]imidazol-4-yl]acetic acid ammonia salt (Isomer 2)

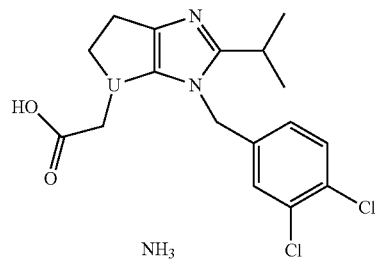

Prepared in exactly the same manner as Example 10 from Intermediate 25 (Isomer 2) (145 mg) to provide the title compound (111 mg). LC/MS MH+ 367, 369, Rt 1.59 min (5 minute run).

Intermediate 26 Ethyl [3-[(4-chlorophenyl)methyl]-4-hydroxy-2-(1-methylethyl)-3,4,5,6-tetrahydrocyclopenta[d]imidazol-4-yl]acetate

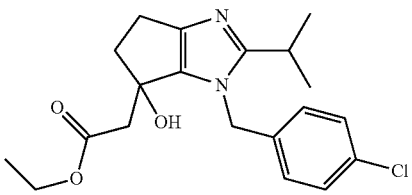 [SMILES: CCOC(=O)CC1(O)CCc2nc(C(C)C)n(Cc3ccc(Cl)cc3)c21]

Ethyl acetate (0.234 mL) in dry THF (1 ml) was added dropwise to a stirred solution of LiHMDS, 1M in THF (2.389 mL) cooled to −78° C. under nitrogen atmosphere. The mixture was stirred at −78° C. for 30 minutes. Then, Intermediate 18 (230 mg) in THF (2 ml) was added dropwise. The RM was stirred at −78° C. under nitrogen for 1 hour.

The reaction was quenched with 10 mL of sat. aq. NH4Cl. The reaction mixture was warmed up to room temperature and partitioned with ethyl acetate (25 mL). The 2 phases were separated, the aqueous phase extracted with EtOAc (2×25 mL), the organic extracts were combined, dried (hydrophobic frit) and concentrated under vacuum to give the title compound (186 mg). LC/MS MH+ 377, Rt 0.79 min (2 minute run).

Intermediate 27 Ethyl-[3-[(4-chlorophenyl)methyl]-2-(1-methylethyl)-5,6-dihydrocyclopenta[d]imidazol-4(3H)-ylidene]ethanoate

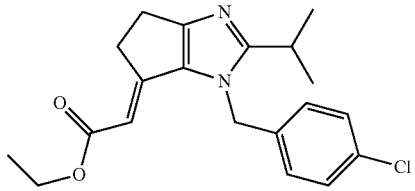 [SMILES: CCOC(=O)/C=C1\CCc2nc(C(C)C)n(Cc3ccc(Cl)cc3)c21]

A mixture of TMSCl (0.252 mL) and sodium iodide (296 mg) in Acetonitrile (3 ml) was added to a stirred suspension of Intermediate 26 (186 mg) in acetonitrile (3 ml). The RM was stirred at room temp under nitrogen overnight. The reaction mixture was partitioned between EtOAc (20 ml) and sat. NaHCO3 aq sol: water (1:1, 20 ml). The two phases were separated and the aqueous phase was extracted again with EtOAc (20 ml). The phases were separated, the organic extracts were combined, dried (hydrophobic frit) and concentrated under vacuum. The residue was purified on silica using a cyclohexane:ethyl acetate 0-100% gradient. The desired fractions were combined and concentrated under vacuum to give the title compound (170 mg). LC/MS MH+ 359, 369, Rt 1.01 min (2 minute run).

Example 12

[2-(1-methylethyl)-3-(phenylmethyl)-3,4,5,6-tetrahydrocyclopenta[d]imidazol-4-yl]acetic acid ammonia salt

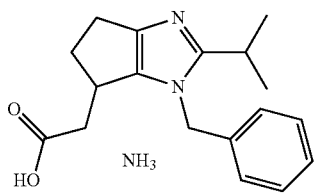

Intermediate 27 (33 mg) was dissolved in methanol (2 mL) and treated with magnesium powder (22.35 mg) at room temperature for 16 h. The reaction mixture was heated at 60° C. for 3 h. The mixture was filtered off on celite and the filtrate concentrated under vacuum to give 30 mg of the SM. The residue was dissolved in methanol (10 mL) and hydrogenated using the H-cube (settings: 18° C., 1 ml/min flow rate) and 10% Pd/C CatCart 30 as the catalyst. The solvent was removed under vacuum and the residue was purified by MDAP (Method B). The solvent from the main peak was evaporated in vacuo to give a colourless oil (17 mg). The residue was dissolved in Ethanol (1 mL) and treated with 2M aq NaOH (500 uL). The solution was left standing overnight. The residue was purified by MDAP (Method B). The solvent was dried under a stream of nitrogen in the Radleys blow-down apparatus to give the required product (17 mg). The residue was dissolved in MeOH:DCM (1:1, 3 mL) and eluted through an NH2 column (1 g). The column was washed with MeOH (2 column volumes) and then with 2M NH3 in MeOH (3 column volumes). The desired fraction was concentrated in vacuo to give the title compound (14 mg). LC/MS MH+ 299, Rt 1.65 min (5 minute run).

Intermediate 28 2-cyclopropyl-5,6-dihydrocyclopenta[d]imidazol-4(1H)-one

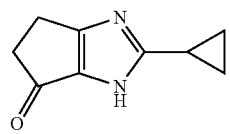 [SMILES: O=C1CCc2nc(C3CC3)[nH]c21]

A mixture of cyclopropanecarboximidamide hydrochloride (0.757 g), 2-bromo-3-(methyloxy)-2-cyclopenten-1-one (1 g) and potassium carbonate (2.171 g) in N,N-dimethylformamide (15 mL) were heated at 100° C. for 3 h. Potassium carbonate (1 g) was added and the mixture heated at 110° C. for further 16 h. The reaction mixture was cooled down to room temperature and partitioned between dichloromethane (60 mL) and sat. aq. NH4Cl (60 mL). The 2 phases were separated, the aqueous was extracted with DCM (2×40 mL), the organic extracts were combined, dried (hydrophobic frit) and concentrated under vacuum. The residue was purified on silica using a cyclohexane:ethyl acetate 0-100% gradient with a 0->20% Ethyl Acetate-MeOH wash at the end. The desired fractions (in the MeOH wash) were combined and concentrated under vacuum to give the title compound (272 mg), used crude in the next reaction. LC/MS MH+ 163, Rt 1.45 min (5 minute run).

Intermediate 29 3-[(4-chlorophenyl)methyl]-2-cyclopropyl-5,6-dihydrocyclopenta[d]imidazol-4(3H)-one

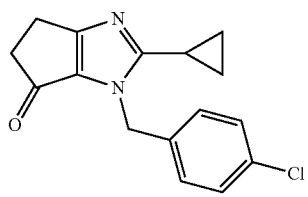 [SMILES: O=C1CCc2nc(C3CC3)n(Cc3ccc(Cl)cc3)c21]

Tetrabutylammonium bromide (270 mg) was added to a stirred mixture of Intermediate 28 (272 mg), 4-chlorobenzyl bromide (414 mg) in sodium hydroxide 20% aq. (3.09 mL) and toluene (10 mL). The RM was stirred at room temp under nitrogen atm. for 16 hours. Sat. NH4Cl aq. solution (50 mL) was added and the mixture was extracted with EtOAc (2×50 ml). The organics were combined, dried (hydrophobic frit) and concentrated under vacuum. The residue was purified on silica using a cyclohexane:ethyl acetate 0-100% gradient. The desired fractions were combined and concentrated under vacuum to give the title compound (238 mg). LC/MS MH+ 387, Rt 2.51 min (5 minute run)

Intermediate 30 3-[(4-chlorophenyl)methyl]-2-cyclopropyl-3,4,5,6-tetrahydrocyclopenta[d]imidazol-4-ol

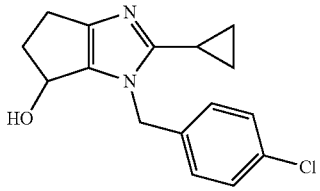 [SMILES: OC1CCc2nc(C3CC3)n(Cc3ccc(Cl)cc3)c21]

Sodium borohydride (94 mg) was added to a stirred solution of Intermediate 29 (238 mg) in dichloromethane (3 ml) and methanol (3.00 ml). The reaction mixture was stirred for 16 hours. The reaction mixture was concentrated under vacuum, partitioned between EtOAc (20 ml) and water (15 ml). The two phases were separated and the aqueous phase was extracted again with EtOAc (2×10 ml). The phases were separated, the organic extracts were combined, dried (hydrophobic frit) and concentrated under vacuum. The residue was purified on silica using a dichloromethane:methanol 0-25% gradient. The fractions were combined and concentrated under vacuum. The residue was purified by MDAP (Method B, UV detection only). The solvent was evaporated in vacuo to give the required product (94 mg).

LC/MS MH$^+$ 289, Rt 2.36 min (5 minute run).

Intermediate 31 Triethyl {3-[(4-chlorophenyl)methyl]-2-cyclopropyl-3,4,5,6-tetrahydrocyclopenta[d]imidazol-4-yl}methanetricarboxylate

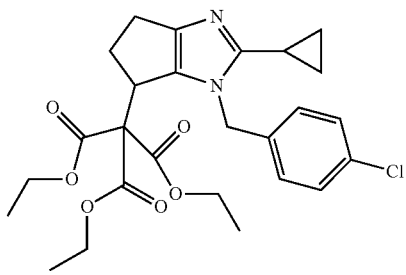 [SMILES: CCOC(=O)C(C(=O)OCC)(C(=O)OCC)C1CCc2nc(C3CC3)n(Cc3ccc(Cl)cc3)c21]

To a solution of Intermediate 30 (95 mg) and triethylmethanetricarboxylate (0.140 ml) in toluene (1.5 ml) and tetrahydrofuran (1.5 ml), stirred at RT under an inert atmosphere of nitrogen, was added trimethylphosphine, 1M in toluene (0.658 ml). The resulting solution was cooled to −78° C. and diisopropyl azodicarboxylate (0.130 ml) was added dropwise via syringe and the reaction was stirred at −78° C. for 45 mins. The reaction mixture was removed from the cold bath and allowed to warm to RT and stirred under N2 atmosphere overnight. Reaction mixture concentrated in vacuo. The residue was taken up in DCM (20 ml) and washed with water (20 mL). The 2 phases were separated, the organic extract was dried (hydrophobic frit) and concentrated under vacuum. The residue was purified on silica using a cyclohexane:ethyl acetate 0-100% gradient. The desired fractions were combined and concentrated under vacuum to give the title compound (146 mg). LC/MS MH$^+$503, Rt 3.37 min (5 minute run).

Example 13

{3-[(4-chlorophenyl)methyl]-2-cyclopropyl-3,4,5,6-tetrahydrocyclopenta[d]imidazol-4-yl}acetic acid ammonia salt

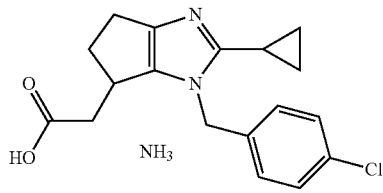

Intermediate 31 (143 mg) was dissolved in ethanol (5 ml) and the resulting soln. was treated with sodium hydroxide, 3M aq. (1 ml). The resulting suspension was heated to reflux for 2 hr. The reaction mixture was allowed to cool and concentrated in vacuo.

The crude residue was taken up in acetic acid (10 ml) and heated to reflux for 1.5 hr. Reaction mixture concentrated in vacuo. The residue was purified by MDAP (Method B). The solvent was evaporated in vacuo to give the required product (77 mg). LC/MS MH$^+$ 331, Rt 1.77 min (5 minute run).

Intermediate 32 2-(1,1-dimethylethyl)-5,6-dihydrocyclopenta[d]imidazol-4(1H)-one

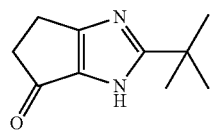

A mixture of 2,2-dimethylpropanimidamide hydrochloride (0.858 g), 2-bromo-3-(methyloxy)-2-cyclopenten-1-one (1 g) and potassium carbonate (2.53 g) in N,N-dimethylformamide (15 mL) were heated at 80° C. for 20 h. The reaction mixture was cooled down to room temperature and DCM (20 mL) was added. The mixture was filtered and the filtrate concentrated under vacuum. The residue was purified by reverse phase chromatography using Acetonitrile Water with an ammonium carbonate modifier gradient (5-40%). The desired fractions were combined and concentrated under vacuum to yield 685 mg of the title compound. LC/MS MH$^+$ 179, Rt 1.48 min (5 minute run).

Intermediate 33 3-[(4-chlorophenyl)methyl]-2-(1,1-dimethylethyl)-5,6-dihydrocyclopenta[d]imidazol-4(3H)-one

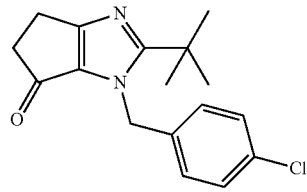 [SMILES: CC(C)(C)c1nc2c(n1Cc1ccc(Cl)cc1)C(=O)CC2]

Tetrabutylammonium bromide (317 mg) was added to a stirred mixture of Intermediate 32 (350 mg), 4-chlorobenzyl bromide (444 mg) in sodium hydroxide 15% aq. (10 mL) and toluene (15 mL). The RM was stirred at room temp under nitrogen atm. for 16 hours. Sat. NH4Cl aq. solution (10 mL) was added and the mixture was extracted with EtOAc (2×50 ml). The organics were combined, dried (hydrophobic frit) and concentrated under vacuum The residue was purified on silica (50 g) using a cyclohexane:ethyl acetate 0-100% gradient. The desired fractions were combined and concentrated under vacuum to give the title compound (421 mg). LC/MS MH+ 303, Rt 2.51 min (5 minute run).

Intermediate 34 3-[(4-chlorophenyl)methyl]-2-(1,1-dimethylethyl)-3,4,5,6-tetrahydrocyclopenta[d]imidazol-4-ol

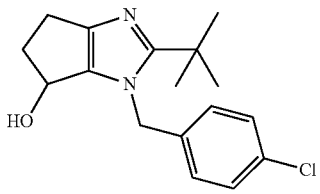

Sodium borohydride (158 mg) was added to a stirred solution of Intermediate 33 (421 mg) in dichloromethane (3 ml) and methanol (3.00 ml). The reaction mixture was stirred for 16 hours. The reaction mixture was concentrated under vacuum, partitioned between EtOAc (40 ml) and water (40 ml). The two phases were separated and the aqueous phase was extracted again with EtOAc (30 ml). The phases were separated, the organic extracts were combined, dried (hydrophobic frit) and concentrated under vacuum to give the required product (404 mg). LC/MS MH+ 305, Rt 2.59 min (5 minute run).

Intermediate 35 Triethyl [3-[(4-chlorophenyl)methyl]-2-(1,1-dimethylethyl)-3,4,5,6-tetrahydrocyclopenta[d]imidazol-4-yl]methanetricarboxylate

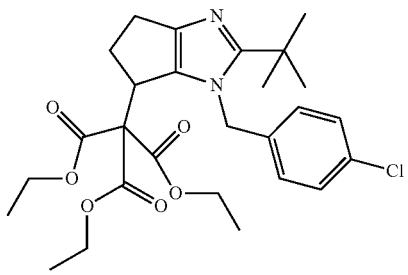 [SMILES: CCOC(=O)C(C(=O)OCC)(C(=O)OCC)C1CCc2nc(C(C)(C)C)n(Cc3ccc(Cl)cc3)c21]

To a suspension of Intermediate 34 (300 mg) and triethylmethanetricarboxylate (0.417 ml) in toluene (3.5 ml) and methyltetrahydrofuran (3.50 ml), stirred at RT under an inert atmosphere of nitrogen, was added trimethylphosphine, 1M in toluene (1.97 ml). The resulting solution was cooled to −78° C. and diisopropyl azodicarboxylate (0.39 ml) was added dropwise via syringe and the reaction was stirred at −78° C. for 45 mins. The reaction mixture was removed from the cold bath and allowed to warm to RT and stirred under N2 atmosphere overnight. Reaction mixture concentrated in vacuo. The residue was taken up in DCM (20 ml) and washed with water (20 mL). The 2 phases were separated, the organic extract was dried (hydrophobic frit) and concentrated under vacuum. The residue was purified on silica using a cyclohexane:ethyl acetate 0-100% gradient. The desired fractions were combined and concentrated under vacuum to give the title compound (496 mg). LC/MS MH+ 519, Rt 3.53 min (5 minute run)

Example 14

[3-[(4-chlorophenyl)methyl]-2-(1,1-dimethylethyl)-3,4,5,6-tetrahydrocyclopenta[d]imidazol-4-yl]acetic acid ammonia salt

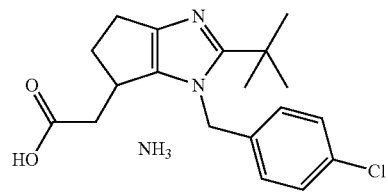

Intermediate 35 (496 mg) was dissolved in ethanol (5 ml) and the resulting soln. was treated with sodium hydroxide, 2M aq (3 ml). The resulting suspension was heated to reflux for 4 hr. The reaction mixture was allowed to cool and concentrated in vacuo. The crude residue was taken up in acetic acid (10.00 ml) and heated to reflux for 1 hr. Reaction mixture concentrated in vacuo. The residue was purified by reverse phase chromatography using acetonitrile water with an ammonium carbonate modifier gradient. The desired fractions were combined and concentrated under vacuum to give the title compound (304 mg) as a white solid. LC/MS MH+ 347, Rt 1.93 min (5 minute run).

Intermediate 36 1-[(4-chlorophenyl)methyl]-4,5-diiodo-2-(1-methylethyl)-1H-imidazole

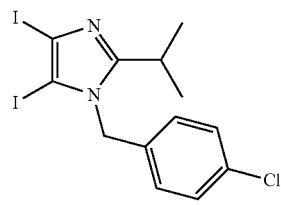 [SMILES: CC(C)c1nc(I)c(I)n1Cc1ccc(Cl)cc1]

Solution A=4,5-diiodo-2-(1-methylethyl)-1H-imidazole (17 g)+tetrahydrofuran (60 ml)+toluene (60.0 ml)
Solution B=NaHMDS in toluene (102 ml, 61.1 mmol)
Solution C=4-chlorobenzylbromide (10.62 g)+toluene (120 mL)

Solution A was cooled in an ice-bath, and solution B added dropwise. The mixture was allowed to stir for 15 minutes, before dropwise addition of solution C. The mixture was then allowed to warm to RT and stirring continued overnight, at which point LCMS indicated no starting benzyl bromide remained. Some of the solvents were removed under reduced pressure, and the remaining material was treated with water. The aqueous was then extracted with EtOAc (2×20 mL), and the combined organics were washed with brine, passed through a hydrophobic frit, and concentrated in vacuo. Purification via flash column chromatography (silica, DCM) afforded 4 UV active peaks. The appropriate fractions (peak 4) were combined and concentrated under reduced pressure to give the title compound (12.5 g), containing 28 mol % DCM. LC/MS MH+ 487, Rt 3.17 min (5 minute run).

Intermediate 37 1-[(4-chlorophenyl)methyl]-4-iodo-2-(1-methylethyl)-1H-imidazole

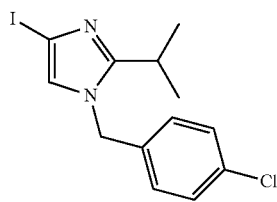 [SMILES: CC(C)c1nc(I)cn1Cc1ccc(Cl)cc1]

Solution A=Intermediate 36+THF (to give a volume of 24 mL)

Solution B=ethylmagnesium bromide in ether (9 mL, 27.0 mmol)+THF (15 mL) 2.0 mL of each reagent were injected into a flow reactor via loading onto 2.5 mL loops on VICI 6-port HPLC valves. The output was collected into 10 mL saturated ammonium chloride solution, which was then treated with ether and the ether phase analysed by LCMS. The remainder of the material was processed under the same conditions, but by running the reagents directly through the pumps—note that not all of solution A was injected. The output was again collected into NH4Cl and treated with ether. The ethereal phase was passed through a hydrophobic frit and concentrated under reduced pressure. Purification via flash column chromatography (silica, 0-50% EtOAc in cyclohexane) afforded a single UV active peak. The appropriate fractions were combined and concentrated under reduced pressure to give the title compound (6.66 g). LC/MS MH+ 361, Rt 2.16 min (5 minute run).

Intermediate 38 1-[(4-chlorophenyl)methyl]-4-ethenyl-2-(1-methylethyl)-1H-imidazole

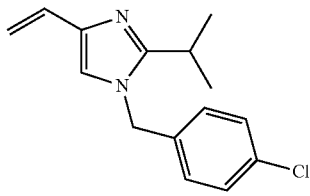 [SMILES: C=Cc1cn(Cc2ccc(Cl)cc2)c(C(C)C)n1]

Intermediate 37 (8.6 g), Tributyl(vinyl) tin (7.56 g), Pd2dba3 (0.436 g), triphenyl phosphine (0.375 g), DMF (100 mL).

The above were mixed together and heated to 90° C. in a flask equipped with a reflux condenser under argon. The mixture was allowed to cool before most of the DMF was stripped in vacuo. The residue was diluted with ethanol and passed through a celite cartridge, which was washed well with EtOH. The eluted solution was concentrated in vacuo, and the residue partitioned between water/EtOAc. The aqueous was further extracted with EtOAc, and the combined organics were passed through a hydrophobic frit and the solvent stripped under reduced pressure. The residue was dissolved in MeCN and washed with pentane (3×50 mL) to remove excess tin. The MeCN layer was then evaporated to dryness and purified by flash column chromatography (silica, 0-100% EtOAc in cyclohexane). The appropriate vials were combined and concentrated under reduced pressure to give the title compound (4.44 g). LC/MS MH+ 261, Rt 1.54 min (5 minute run).

Intermediate 39 Methyl 1-[(4-chlorophenyl)methyl]-2-(1-methylethyl)-4,5,6,7-tetrahydro-1H-benzimidazole-7-carboxylate

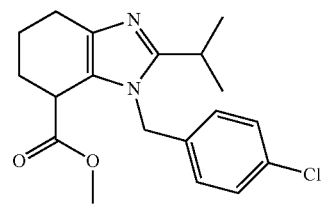 [SMILES: COC(=O)C1CCCc2nc(C(C)C)n(Cc3ccc(Cl)cc3)c21]

Intermediate 38 (4.44 g), methyl acrylate (7.33 g).

The above reagents were mixed together and heated at 130° C. in a flask equipped with a reflux condenser over the weekend. Stirring continued for a further 24 hours but TLC analysis indicated incomplete reaction. Stirring continued for a further 24 hours, at which point the flask was removed from the heat and allowed to cool. The solvents were then stripped in vacuo, and the residue purified by flash column chromatography (silica, 0-100% EtOAc in DCM). The appropriate vials were combined and concentrated under reduced pressure to afford the title compound (4.37 g). LC/MS MH+ 347, Rt 1.70 min (5 minute run).

Intermediate 40 [1-[(4-chlorophenyl)methyl]-2-(1-methylethyl)-4,5,6,7-tetrahydro-1H-benzimidazol-7-yl]methanol

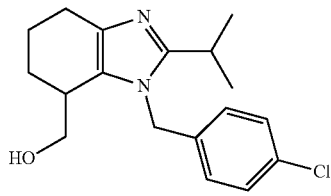 [SMILES: CC(C)c1nc2c(n1Cc1ccc(Cl)cc1)C(CO)CCC2]

Solution A=Intermediate 39 (4.37 g)+THF (12 mL)
Solution B=LiAlH in THF (12.60 mL, 12.60 mmol)
4×1 mL reactions carried out on flow apparatus. Reagents injected (1:1 v/v) via loading onto 2.75 mL PFA loops on VICI 6-port HPLC valves. Toluene used as system solvent. Reaction at 0° C. achieved by placing the reactors in a bowl of iced water. Reactions collected into water, and the organic phase analysed by LCMS.

Reaction scaled-up in 4 mL reactions using conditions with the remaining material. Note that the T-piece mixer blocked during the first injection. The mixer was replaced and the reactors flushed with toluene. The reactor was then replaced for 50' 1.55 mm ID PFA tubing—no further issues with blocking. All of the collected reactions were combined, and the mixture filtered to remove aluminium salts. The filter cake was washed with EtOAc, and the filtrate phases were separated and the aqueous further extracted with EtOAc (×2). The combined organics were passed through a hydrophobic frit and concentrated under reduced pressure and on high-vac to give the title compound by (3.28 g). LC/MS MH+ 319, Rt 1.54 min (5 minute run)

Intermediate 41 [1-[(4-chlorophenyl)methyl]-2-(1-methylethyl)-4,5,6,7-tetrahydro-1H-benzimidazol-7-yl]methyl methanesulfonate

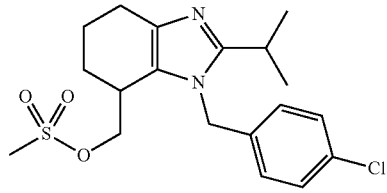 [SMILES: CC(C)c1nc2c(n1Cc1ccc(Cl)cc1)C(COS(C)(=O)=O)CCC2]

Mesyl chloride (0.874 mL) was added dropwise to a suspension of Intermediate 40 (2.98 g) in dichloromethane (100 mL) at 0° C. under N2. Once addition was complete, the reaction was allowed to stir at 0° C. for a further 30 minutes before the bath was removed and the solution warmed to RT. The reaction mixture was quenched with water, and the aqueous extracted with DCM. The combined organics were passed through a hydrophobic frit and concentrated under reduced pressure, azeotroped with MeOH and dried on the high-vac to give the title compound 3.44 g. LC/MS MH+ 397, Rt 1.78 min (5 minute run).

Intermediate 42 [1-[(4-chlorophenyl)methyl]-2-(1-methylethyl)-4,5,6,7-tetrahydro-1H-benzimidazol-7-yl]acetonitrile

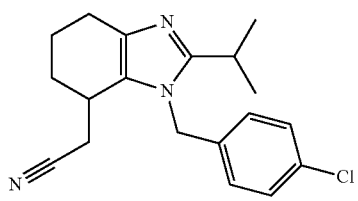 [SMILES: CC(C)c1nc2c(n1Cc1ccc(Cl)cc1)C(CC#N)CCC2]

Intermediate 41 (3.8 g) and sodium cyanide (1.41 g) was dissolved in dimethyl sulfoxide (20 mL) and the mixture was stirred at 60° overnight. The reaction was stopped (only 1 g nitrile required) and cooled to RT before diluting with water/DCM. The aqueous was further extracted with DCM, and the combined organic extracts were passed though a hydrophobic frit, reduced in volume in vacuo, and the residue purified by flash column chromatography (0-15% MeOH in DCM, silica, repeated chromatography required). The appropriate fractions were combined to give the title compound (1.57 g).

1.3 g of the racemic material was resolved by chiral chromatography eluting with 2% EtOH/Heptane, on a 5 cm×20 cm Chiralpak AD (20 um) (self packed) column. The following isomers were isolated, in order of elution off the column.

Intermediate 43 [1-[(4-chlorophenyl)methyl]-2-(1-methylethyl)-4,5,6,7-tetrahydro-1H-benzimidazol-7-yl]acetonitrile (Isomer 1)

LC/MS MH+ 328, Rt 2.06 min (5 min run).

Intermediate 44 [1-[(4-chlorophenyl)methyl]-2-(1-methylethyl)-4,5,6,7-tetrahydro-1H-benzimidazol-7-yl]acetonitrile (Isomer 2)

LC/MS MH+ 328, Rt 2.06 min (5 min run).

Example 15

[1-[(4-chlorophenyl)methyl]-2-(1-methylethyl)-4,5,6,7-tetrahydro-1H-benzimidazol-7-yl]acetic acid

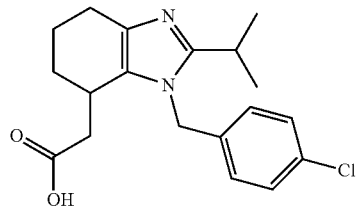 [SMILES: CC(C)c1nc2c(n1Cc1ccc(Cl)cc1)C(CC(=O)O)CCC2]

A solution of Intermediate 42 (45 mg) in methanol (0.4 ml) was treated with 4.5M potassium hydroxide (0.2 ml). The reaction vessel was sealed and heated in CEM Discover using initial 50 W to 150° C. for 30 mins. The mixture was reheated in the microwave at 150° C. for 1 h. A further aliquot of 4.5M potassium hydroxide (0.05 ml) was added and the mixture was heated in the microwave at 160° C. for 30 mins. A further aliquot of 4.5M potassium hydroxide (0.05 ml) was added and the mixture was heated in the microwave at 160° C. for 1 h. The mixture was filtered through a frit and the filtrate diluted with DMSO to 1 ml. The sample was purified by MDAP (Method A). The solvent was dried under a stream of nitrogen in the Radleys blowdown apparatus to give the product (39.2 mg)

LC/MS MH+ 347, 349, Rt 0.76 min (5 min run).

Example 16

[1-[(4-chlorophenyl)methyl]-2-(1-methylethyl)-4,5,6,7-tetrahydro-1H-benzimidazol-7-yl]acetic acid (Isomer 1)

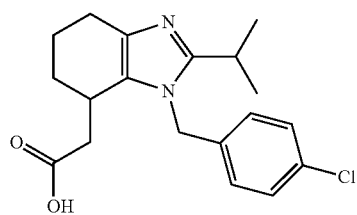 [SMILES: CC(C)c1nc2c(n1Cc1ccc(Cl)cc1)C(CC(=O)O)CCC2]

A solution of Intermediate 43 (isomer 1) (32.8 mg) in ethanol (1 mL) and 10M potassium hydroxide (0.1 mL,) was heated to reflux overnight. Further 10M potassium hydroxide (0.1 mL) was added and the mixture heated for 3 days at reflux. The mixture was cooled. Hydrochloric acid (500 ul) was added and the mixture stirred for 10 minutes. An SCX cartridge (2 g) was washed with 1:1 acetonitrile:water and the reaction mixture passed through. The column was washed with a volume of 1:1 acetonitrile water and a volumn of acetonitrile. The product was eluted in 2M ammonia in methanol. Reduction in vacuo of the latter eluent gave 7 mg of product. The column washings were passed through a second 5 g SCX cartridge and the column washed with a volume of 1:1 acetonitrile water and a volumn of acetonitrile. The product was eluted in 2M ammonia in methanol. This was also reduced in vacuo and the solids combined to give a single batch of the product (23 mg). LC/MS MH+ 347, Rt 1.95 mins (5 min run. TFA modifier).

Example 17

(−)-[1-[(4-chlorophenyl)methyl]-2-(1-methylethyl)-4,5,6,7-tetrahydro-1H-benzimidazol-7-yl]acetic acid ammonia salt (Isomer 2)

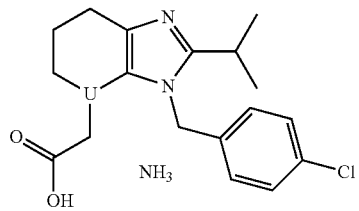

A solution of Intermediate 44 (isomer 2) (513 mg) in methanol (3 mL) and 10M potassium hydroxide (2.5 mL) was added and the mixture heated for 2 days at reflux. The mixture was cooled. Hydrochloric acid (15.65 mL) was added and the mixture stirred for 10 minutes. An SCX cartridge (50 g) was washed with 1:1 acetonitrile:water and the reaction mixture passed through. The column was washed with a volume of 1:1 acetonitrile water and a volume of acetonitrile. The product was eluted in 2M ammonia in methanol. Reduction in vacuo of the latter eluent gave 500 mg of product. The material contained ca 8% methyl ester. LC/MS MH+ 347, Rt 1.94 mins (5 min run. TFA modifier).

Example 32

(−)-[1-[(4-chlorophenyl)methyl]-2-(1-methylethyl)-4,5,6,7-tetrahydro-1H-benzimidazol-7-yl]acetic acid (Isomer 2)

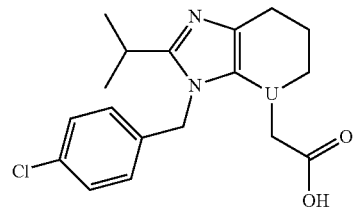

Recrystallisation of Example 17 was attempted using isopropanol. Ca 7 mL of refluxing isopropanol resulted in dissolution of the product (Example 17) at reflux. The mixture was cooled and minimal precipitation was observed therefore the mixture was blown down slowly at 40° C. The resulting solid was suspended in refluxing acetone and allowed to cool. Filtration of the resulting solid provided the product (360 mg, free base). LC/MS MH+ 347, Rt 1.95 mins (5 min run. TFA modifier). [α]$_D$=−19.8° (24° C., 1:1 methanol:DCM). $^1$H NMR (DMSO d6) δ 1.03 (d, 3H), 1.12 (d, 3H), 1.60-1.66 (m, 4H), 2.20-2.46 (m, 4H), 2.81 (pent., 1H), 2.95 (m, 1H), 5.08 (d, 1H), 5.14 (d, 1H), 6.92 (d, 2H), 7.42 (d, 2H), 12.2 (br.s 1H).

Intermediate 45
Ethyl(2-hydroxy-3-oxo-1-cyclohexen-1-yl)acetate

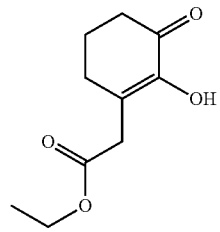

n-Butyl lithium (101 mL, 161 mmol) was added to a stirred solution of diisopropylamine (22.96 mL) in methyl-THF (200 mL) at −10° C. The resulting solution was stirred at −10° C. for 15 mins. 1,2-cyclohexanedione (8.6 g) was added to the reaction mixture as a solution in methyl-THF (28 mL). During the addition the internal temperature of the reaction was maintained between −15° C. and −5° C. by modulation of delivery rate. The resulting dark orange/brown solution was stirred at −10° C. for a further 15 mins. The reaction mixture was then cooled to −78° C. and ethyl bromoacetate (12.76 mL) was added dropwise via syringe. Further ethyl bromoacetate (0.8 mL) was added, no further evolution of heat was observed therefore the reaction was left to stir at −60 to −70° C. (internal temp) for 1 hour 15 minutes. The reaction mixture was quenched at −78° C. with 0.5 M HCl (400 ml), allowed to warm to RT and extracted with diethyl ether (200 ml). The organic layer was washed with water (300 mL) and saturated brine. The crude reaction mixture was purified by flash column chromatography (100 g, silica, ethyl acetate/cyclohexane, 0-50%) to give the title compound (7.1 g). LC/MS MH+ 199, Rt 1.78 mins (5 min system).

NB for future reference—only 1 eq of ethyl bromoacetate is needed. The product was a 3:1 mixture of enol isomers.

Intermediate 46 Ethyl [1-[(2,4-dichlorophenyl)methyl]-2-(1-methylethyl)-4,5,6,7-tetrahydro-1H-benzimidazol-7-yl]acetate

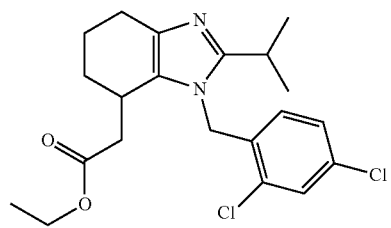 [SMILES: CCOC(=O)CC1CCCc2nc(C(C)C)n(Cc3ccc(Cl)cc3Cl)c21]

2,4-dichlorobenzyl amine (0.080 mL), isovaleraldehyde (0.046 mL), ammonium acetate (38.5 mg), Intermediate 45 (99 mg) and acetic acid (0.143 mL) were mixed in chloroform (1 mL) and heated to 140° C. (Biotage Initiator) for 20 minutes. The mixture was purified by MDAP (Method C). The appropriate fractions were passed through SCX (5 g) and washed with methanol. The products were collected by elution in 2M ammonia in methanol. Title compound (35 mg). LC/MS MH+ 409, Rt 2.38 min (5 min run, TFA modifier).

Example 18

[1-(2,4-dichlorobenzyl)-2-isopropyl-4,5,6,7-tetrahydro-1H-benzimidazol-7-yl]acetic acid ammonia salt

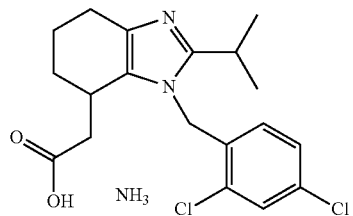

Intermediate 46 (35 mg) was dissolved in 2 ml of MeTHF. Potassium trimethylsilanoate (12.19 mg) was added and the mixture stirred at room temperature overnight. 2 ml further MeTHF was added to the reaction, followed by Methanol. 4 M equivalent of sodium hydroxide was added and the reaction stirred at 50° C. for 2 hours. The reaction mixture passed through an SCX ion exchange column (10 g) and eluted with 2M Ammonia and methanol. (28 mg). LC/MS MH+ 381, Rt 2.06 min (5 min run, TFA modifier).

Intermediate 47 Ethyl [1-[(3,4-dichlorophenyl)methyl]-2-(1-methylethyl)-4,5,6,7-tetrahydro-1H-benzimidazol-7-yl]acetate

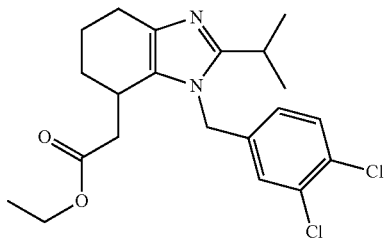 [SMILES: CCOC(=O)CC1CCCc2nc(C(C)C)n(Cc3ccc(Cl)c(Cl)c3)c21]

A solution of Intermediate 45 (600 mg), ammonium acetate (233 mg), 3,4-dichlorobenzylamine (0.484 mL), acetic acid (0.866 mL) and isobutyraldehyde (0.276 mL) in chloroform (6 mL) was heated to 65° C. The reaction was heated for 21 hr, after which time the reaction mixture was partitioned between ethyl acetate (100 mL) and 1 M NaOH aqueous soln. (100 mL). The organic layer was separated and the aqueous layer extracted with further DCM (1×100 mL). The combined organic layers were filtered through a hydrophobic frit and conc. in vacuo to afford 1.18 g of crude product. The crude product was purified by flash column chromatography (silica, 0-100% cyclohexane/ethyl acetate) to afford the desired regioisomer (250 mg). LC/MS MH+ 409/411/413, Rt 2.47 min (5 min run).

Example 19

[1-[(3,4-dichlorophenyl)methyl]-2-(1-methylethyl)-4,5,6,7-tetrahydro-1H-benzimidazol-7-yl]acetic acid

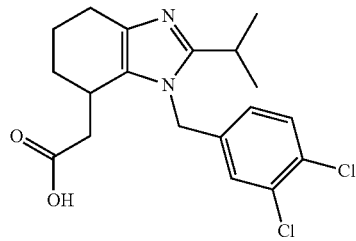 [SMILES: CC(C)c1nc2c(n1Cc1ccc(Cl)c(Cl)c1)C(CC(=O)O)CCC2]

Intermediate 47 (330 mg) was dissolved in methanol (3 mL) and 2M sodium hydroxide (2.42 mL) was added and the mixture stirred overnight. The mixture was blown down by ca 50% and the pH adjusted to 6 by addition of 2M hydrochloric acid. The precipitate was collected by filtration, washed with water and dried in vacuo to provide the title compound (100 mg) LC/MS MH+ 381, Rt 2.03 mins (5 min run, TFA modifier).

Intermediate 48 phenylmethyl [1-[(3,4-dichlorophenyl)methyl]-2-(1-methylethyl)-4,5,6,7-tetrahydro-1H-benzimidazol-7-yl]acetate

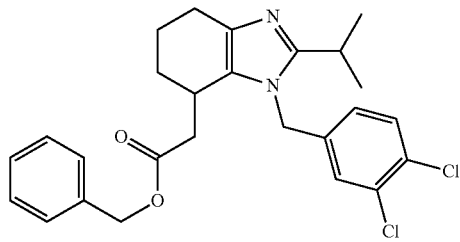 [SMILES: CC(C)c1nc2c(n1Cc1ccc(Cl)c(Cl)c1)C(CC(=O)OCc1ccccc1)CCC2]

Intermediate 47 (250 mg) was dissolved in methanol (5 mL) and sodium hydroxide (160 mg) was added as a 2M aqueous solution. The reaction mixture was left to stir at rt. After stirring for 3 days the reaction mixture was conc. in vacuo, dissolved in acetonitrile/water and loaded onto an SCX column. The column was washed with portions of water and acetonitrile and then the product was eluted with 2M ammonia in methanol. The basic washings were conc. in vacuo to afford 210 mg of the ammonia salt. In a second synthetic step this material (201 mg), benzyl alcohol (0.157 mL) and DMAP (6.2 mg) were stirred in dichloromethane (10 mL) at 0° C. DCC (125 mg) was added and the reaction mixture was stirred and allowed warm to rt. After stirring for 3 hr the reaction mixture was filtered and concentrated in vacuo. The crude product mixture was purified in 3 portions by MDAP (Method B) and the appropriate fractions were combined and concentrated to afford 165 mg of product (165 mg). LC/MS MH+ 471/473/475, Rt 2.71 min (5 min run). The enantiomers were separated by chiral chromatography using 10% EtOH/Heptane on a 5 cm×20 cm Chiralpak AD (20 um)

self packed. The two enantiomers were (in order of elution) Intermediate 49 and Intermediate

Example 20

(−)-[1-[3,4-dichlorophenyl)methyl]-2-(1-methyl-ethyl)-4,5,6,7-tetrahydro-1H-benzimidazol-7-yl]acetic acid ammonia salt (Isomer 2)

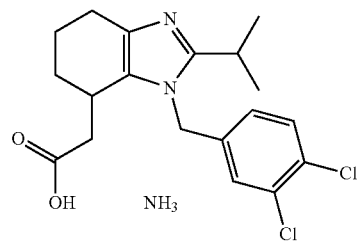

Intermediate 50 (isomer 2) (71.2 mg) was dissolved in methanol (2 mL). Sodium hydroxide (6.04 mg) was added to the stirred reaction mixture as a 3.3 N aqueous soln. After stirring for 18 h the reaction mixture was conc. in vacuo and taken up in acetonitrile/water. The soln. was taken to pH4-5 by the addition of 2 M aqueous HCl and loaded onto an SCX column. After washing with water and acetonitrile, the product was eluted with 2M ammonia soln. in methanol. The washing were conc. in vacuo to afford the ammonium salt of the desired product (60 mg). LC/MS MH$^+$ 381/383/385, Rt 2.06 mins (5 min run). $[\alpha]_D$=−16.9° (24° C., 1:1 methanol:DCM). $^1$H NMR (DMSO d6) δ 1.02 (d, 3H), 1.11 (d, 3H), 1.60-1.75 (m, 4H), 2.21-2.45 (m, 4H), 2.81 (pent., 1H), 2.93 (m, 1H), 5.09 (d, 1H), 5.19 (d, 1H), 6.66 (dd, 1H), 7.23 (d, 1H), 7.62 (d, 1H), (12.3 (br.s, 1H).

Example 21

[1-[(3,4-dichlorophenyl)methyl]-2-(1-methylethyl)-4,5,6,7-tetrahydro-1H-benzimidazol-7-yl]acetic acid ammonia salt (Isomer 1)

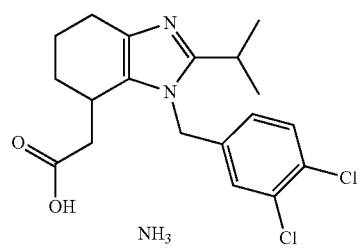

Prepared in exactly the same method as Example 20 from Intermediate 49 (isomer 1) (82 mg) to provide the title compound (58 mg). LC/MS MH$^+$381/383/385, Rt 2.07 mins (5 min run).

Intermediate 51 Ethyl {1-[(4-chlorophenyl)methyl]-2-cyclopentyl-4,5,6,7-tetrahydro-1H-benzimidazol-7-yl}acetate

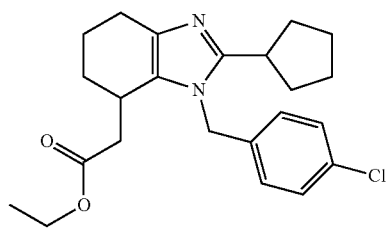 [SMILES: CCOC(=O)CC1CCCc2nc(C3CCCC3)n(Cc3ccc(Cl)cc3)c21]

Intermediate 45 (0.396 g), ammonium acetate (0.154 g), 4-chloro-benzylamine (0.292 ml), were mixed in chloroform (2 mL), to this mixture was added cyclopentanecarbaldehyde (427 ul), propanal (0.144 ml), acetic acid (0.572 ml) and heated to 140° C. (Biotage Initiator) for 20 minutes. The compound was reduced in vacuo and purified with column chromatography. Title compound (170 mg). LC/MS MH$^+$401, Rt 2.47 min (5 min run, TFA modifier).

Example 22

{1-[(4-chlorophenyl)methyl]-2-cyclopentyl-4,5,6,7-tetrahydro-1H-benzimidazol-7-yl}acetic acid ammonia salt

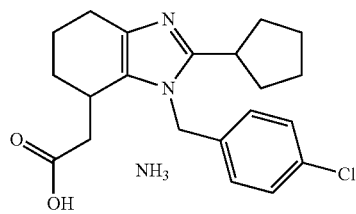

Intermediate 51 (170 mg) was dissolved in 2 ml methanol followed by 4 M equivalent of sodium hydroxide and the mixture stirred at room temperature for 24 hr. The reaction mixture was reduced in vacuo and dissolved in a minimum amount of 1:1 acetonitrile:water. This mixture was passed through an SCX ion exchange column (5 g). The column was washed with 1:1 acetonitrile:water, followed by acetonitrile. The product was eluted with 2M ammonia in methanol and reduced in vacuo. LC/MS MH$^+$ 372, Rt 2.12 mins (5 min run, TFA modifier).

Intermediate 52 2-(1,1-dimethylethyl)-1,5,6,7-tetrahydro-4H-benzimidazol-4-one

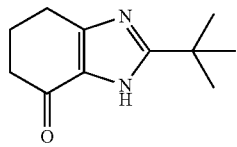

To a stirred solution of 2-bromo-3-(methyloxy)-2-cyclohexen-1-one (0.957 g) in anhydrous N,N-dimethylformamide (20 mL) at ambient temperature was added solid tert-butylcarbamidine hydrochloride (0.638 g) and potassium carbonate (1.613 g, 11.67 mmol). The reaction was then heated to 100° C. under an atmosphere of nitrogen for 2.5 h. The reaction was diluted with dichloromethane (50 mL) the resultant solid was removed by filtration. The filtrate was concentrated in vacuo. The sample was loaded in dichloromethane and purified on silica using a 0-25% methanol-dichloromethane gradient. The appropriate fractions were combined and evaporated in vacuo to give the required product (330 mg).

LC/MS $MH^+$ 193, Rt 0.62 mins (5 min run).

Intermediate 53 3-[(4-chlorophenyl)methyl]-2-(1,1-dimethylethyl)-3,5,6,7-tetrahydro-4H-benzimidazol-4-one

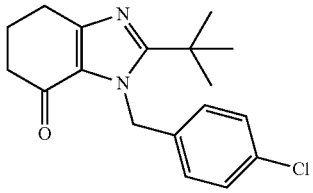 [SMILES: CC(C)(C)c1nc2c(n1Cc1ccc(Cl)cc1)C(=O)CCC2]

To a stirred suspension of Intermediate 52 (325 mg), 1-(bromomethyl)-4-chlorobenzene (417 mg) and tetrabutylammonium bromide (272 mg) in toluene (8 mL) at ambient temperature was added aqueous sodium hydroxide 20% wt (3.25 mL). The reaction was stirred at ambient temperature for 2.5 hr. The reaction was quenched with water (20 mL) and extracted with ethyl acetate (2×20 mL). The combined organics were dried (hydrophobic frit) and concentrated in vacuo. The sample was loaded in dichloromethane and purified on silica using a 0-100% ethyl acetate-cyclohexane gradient. The appropriate fractions were combined and evaporated in vacuo to give the title compound. (126 mg). LC/MS $MH^+$ 317, Rt 2.10 mins (5 min run).

Intermediate 54 1-[(4-chlorophenyl)methyl]-2-(1,1-dimethylethyl)-4,5,6,7-tetrahydro-1H-benzimidazol-7-ol

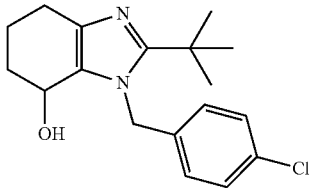

To a stirred solution of Intermediate 53 (120 mg) in a mixture of methanol (1.5 mL) and dichloromethane (1.5 mL) at ambient temperature was added sodium borohydride (30 mg) in one charge. The reaction was stirred at ambient temperature under an atmosphere of nitrogen for 2 hr. The reaction was partitioned between ethyl acetate (20 mL) and water (20 mL). The organics were dried (hydrophobic frit) and concentrated in vacuo to give the title compound (85 mg). LC/MS $MH^+$ 319, Rt 1.92 min (5 min run).

Intermediate 55 Triethyl [1-[(4-chlorophenyl)methyl]-2-(1,1-dimethylethyl)-4,5,6,7-tetrahydro-1H-benzimidazol-7-yl]methanetricarboxylate

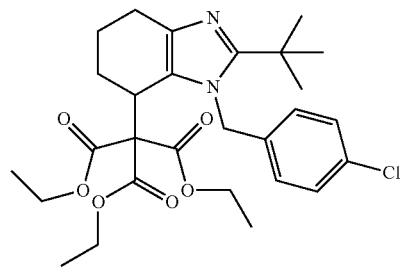 [SMILES: CCOC(=O)C(C(=O)OCC)(C(=O)OCC)C1CCCc2nc(C(C)(C)C)n(Cc3ccc(Cl)cc3)c21]

To a stirred solution of Intermediate 54 (82 mg) and triethylmethanetricarboxylate (0.11 mL) in anhydrous toluene (3 mL) and anhydrous tetrahydrofuran (3.00 mL) under a nitrogen atmosphere was added trimethylphosphine, 1M in toluene (0.52 mL). The reaction was then cooled to −78° C. and diisopropyl azodicarboxylate (0.11 mL) added dropwise via syringe over 1 min. The reaction was stirred at −78° C. under an atmosphere of nitrogen for 60 mins before being allowed to warm to ambient temperature and stirred for a further 16 hr. The reaction was concentrated in vacuo. The residue was taken up in dichloromethane (40 mL) and washed with water (40 mL), dried (hydrophobic frit) and concentrated in vacuo. The sample was loaded in dichloromethane and purified on silica 0-100% ethyl acetate-cyclohexane gradient. The appropriate fractions were combined and evaporated in vacuo to give the required product (100 mg). LC/MS $MH^+$ 533, Rt 2.18 mins (5 min run).

Example 23

[1-[(4-chlorophenyl)methyl]-2-(1,1-dimethylethyl)-4,5,6,7-tetrahydro-1H-benzimidazol-7-yl]acetic acid, formic acid salt

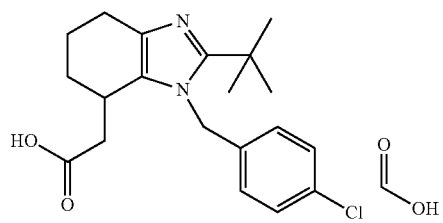

To a stirred solution of Intermediate 55 (95 mg) in ethanol (5 mL) at ambient temperature was added 3.3 M aqueous sodium hydroxide (0.2 mL) in one charge. The reaction was heated at reflux for 4 hr. The reaction was concentrated in vacuo and taken up in glacial acetic acid (10 mL) before heating at reflux for a further 1 hr. The reaction was concentrated in vacuo. The sample was loaded in 1:1 methanol:dichloromethane and purified by SPE on sulphonic acid (SCX) 10 g using sequential solvents methanol, 2M ammonia/methanol. The appropriate fractions were combined and evaporated in vacuo. The sample was dissolved in 1:1 MeOH:DMSO 1 ml and purified by MDAP (Method A). The solvent was dried under a stream of nitrogen in the Radleys blowdown apparatus to give the required product (30 mg) LC/MS MH+ 361, Rt 0.77 min (2 min run).

Intermediate 56 2-(1-methylethyl)-1,5,6,7-tetrahydro-4H-benzimidazol-4-one

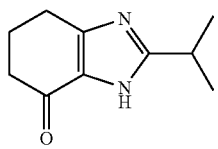

To a stirred solution of 2-bromo-3-(methyloxy)-2-cyclohexen-1-one (1.88 g) in anhydrous N,N-dimethylformamide (35 mL) at ambient temperature was added solid 2-methylpropanimidamide hydrochloride (1.349 g) and potassium carbonate (3.17 g). The reaction was then heated to 100° C. under an atmosphere of nitrogen for 3 hr. The reaction was diluted with dichloromethane (100 mL) the resultant solid was removed by filtration. The filtrate was concentrated in vacuo. The sample was loaded in dichloromethane and purified on silica using a 0-25% methanol-dichloromethane gradient. The appropriate fractions were combined and evaporated in vacuo to give the required product (867 mg). LC/MS MH+ 179, Rt 0.34 min (2 min run).

Intermediate 56 (1st Alternative Preparation) 2-(1-methylethyl)-1,5,6,7-tetrahydro-4H-benzimidazol-4-one

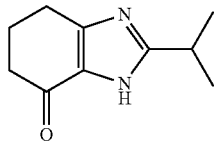

To 2-bromo-3-(ethyloxy)-2-cyclohexen-1-one (160 g) was added N,N-Dimethylformamide (1000 mL) followed by 2-methylpropanimidamide hydrochloride (107 g) and potassium carbonate (151 g). The suspension was then stirred at 50° C. under nitrogen. After 2.75 hr the mixture was filtered and as much DMF as possible was evaporated off under high vacuum. The residue was partitioned between ethyl acetate (400 ml) and a minimum of aq lithium chloride (120 ml). The aqueous layer was extracted well with ethyl acetate (3×200 ml). The combined organics were washed with brine, filtered to give a small amount of a white solid and the filtrate dried (MgSO4), filtered and evaporated, including high vacuum. This was stirred with TBME (350 ml) then filtered to give a white solid, 16.27 gm. The filtrate from this was evaporated and weighed; this partly solidified overnight. Ether and cyclohexane were added to try and precipitate out more product but the solid was oily. The solution was decanted off and gave a golden oil on evaporation, 77 gm. The oily solid was evaporated: 38 gm, dissolved in DCM and purified by column chromatography (silica cartridge), eluting with 0-100% ethyl acetate in dichloromethane over 10 column volumes. Fractions were evaporated and the resulting solid slurried in ether and collected by filtration: This gave a white solid, 4.0 gm. No solid came out from the aqueous phase overnight. So it was extracted with more ethyl acetate and DCM. The organics were dried and evaporated and gave 69 gm of a beige slurry that was stirred with diethyl ether and filtered to give a white solid, 11.3 gm. The filtrate was combined with aqueous extraction solvents from a previous experiment and purified by column chromatography (silica), eluting with 0-100% ethyl acetate in dichloromethane. All product came through in fractions 1 & 2 so they were combined and washed with aq LiCl, dried and re-evaporated to a beige slurry, 46.4 gm, that was stirred in ether and filtered to give a white solid, 5.85 gm. Because all the batches were of the same purity, they were combined: This gave the title compound, a white solid, 37.42 gm.

Intermediate 56 (2nd Alternative Preparation) 2-(1-methylethyl)-1,5,6,7-tetrahydro-4H-benzimidazol-4-one

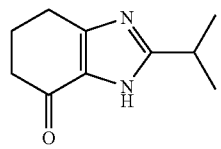

To 2-bromo-3-(ethyloxy)-2-cyclohexen-1-one (38.8 g) in a 1 L round-bottom flask in N,N-Dimethylformamide (DMF) (500 mL) was added 2-methylpropanimidamide hydrochloride (26.1 g) and potassium carbonate (61.2 g). The suspension was then stirred at 80° C. under nitrogen for 2 h. The mixture was filtered and as much DMF as possible was evaporated off under high vacuum. The sample was loaded in dichloromethane and purified by column chromatography over silica using a 0-30% methanol-dichloromethane gradient. The appropriate fractions were combined and evaporated in vacuo to give the required product 14.2 g as a brown solid. LC/MS MH+ 179, Rt 1.4 min (5 min run).

Intermediate 57 3-[(4-chlorophenyl)methyl]-2-(1-methylethyl)-3,5,6,7-tetrahydro-4H-benzimidazol-4-one

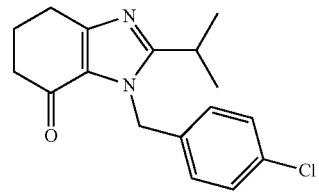 [SMILES: CC(C)c1nc2c(n1Cc1ccc(Cl)cc1)C(=O)CCC2]

To a stirred suspension of Intermediate 56 (867 mg), 1-(bromomethyl)-4-chlorobenzene (1100 mg) and tetrabutylammonium bromide (784 mg) in toluene (20 mL) at ambient temperature was added aqueous sodium hydroxide 20% wt (9 mL). The reaction was stirred at ambient temperature for 2 hr. The reaction was quenched with saturated aqueous ammonium chloride (50 mL) and extracted with ethyl acetate (2×50 mL). The combined organics were dried (hydrophobic frit) and concentrated in vacuo. The sample was loaded in dichloromethane and purified on silica using a 0-100% ethyl acetate-cyclohexane gradient. The appropriate fractions were combined and evaporated in vacuo to give the required product (0.89 g). LC/MS MH+ 303, Rt 2.02 min (5 min run).

Intermediate 58 1-[(4-chlorophenyl)methyl]-2-(1-methylethyl)-4,5,6,7-tetrahydro-1H-benzimidazol-7-ol

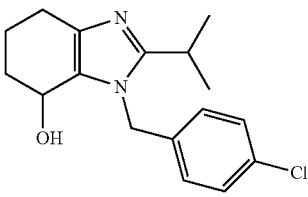 [SMILES: CC(C)c1nc2c(n1Cc1ccc(Cl)cc1)C(O)CCC2]

To a stirred solution of Intermediate 57 (300 mg) in a mixture of methanol (2.5 mL) and dichloromethane (2.5 mL) at ambient temperature was added sodium borohydride (75.0 mg) in one charge. The reaction was stirred at ambient temperature under an atmosphere of nitrogen for 1 hr (incomplete). Stirring continued for 16 hr. The reaction was partitioned between ethyl acetate (40 mL) and water (40 mL). The organic was dried (hydrophobic frit) and concentrated in vacuo to give the title compound (166 mg). LC/MS MH+ 305, 307, Rt 1.38 min (5 min run).

Intermediate 59 Ethyl {[1-[(4-chlorophenyl)methyl]-2-(1-methylethyl)-4,5,6,7-tetrahydro-1H-benzimidazol-7-yl]oxy}acetate

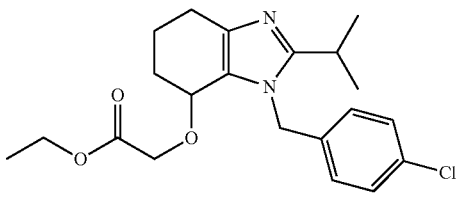 [SMILES: CCOC(=O)COC1CCCc2nc(C(C)C)n(Cc3ccc(Cl)cc3)c21]

To a stirred solution of Intermediate 58 (55 mg) in anhydrous tetrahydrofuran (3 mL) at 0° C. under an atmosphere of nitrogen was added sodium hydride (10 mg) as a 60% by weight suspension on mineral oil in one charge. The reaction was stirred at 0° C. for 30 min. To the reaction was added neat ethyl bromoacetate (0.026 mL) in one charge the reaction was then allowed to warm to ambient temperature under an atmosphere of nitrogen over 30 min. The reaction was quenched with saturated aqueous ammonium chloride (5 mL) and extracted with ethyl acetate (10 mL). The extract was dried (hydrophobic frit) and concentrated in vacuo. The sample was loaded in dichloromethane and purified on silica using a 0-25% methanol-dichloromethane gradient. The appropriate fractions were combined and evaporated in vacuo to provide the title compound (14 mg). LC/MS MH+ 391, Rt 1.84 min (5 min run).

Example 24

{[1-[(4-chlorophenyl)methyl]-2-(1-methylethyl)-4,5,6,7-tetrahydro-1H-benzimidazol-7-yl]oxy}acetic acid, formic acid salt

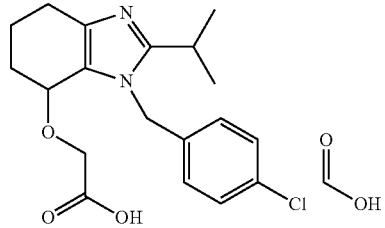

To a solution of Intermediate 59 (12 mg) in tetrahydrofuran (0.5 mL) was added 2M aqueous sodium hydroxide (0.1 mL) in one charge. The reaction was stirred vigorously at ambient temperature for 1 hr. The reaction was concentrated. The sample was dissolved in 1:1 MeOH:DMSO 0.5 ml and purified by MDAP (Method A). The solvent was dried under a stream of nitrogen in the Radleys blowdown apparatus to give the required product (6 mg).

LC/MS MH+ 363, Rt 1.48 min (5 min run).

Intermediate 60 1,1-dimethylethyl {[1-[(4-chlorophenyl)methyl]-2-(1-methylethyl)-4,5,6,7-tetrahydro-1H-benzimidazol-7-yl]oxy}acetate

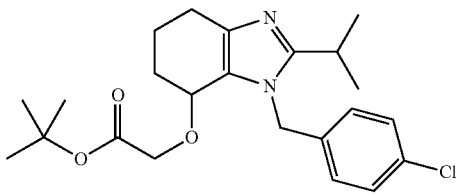 [SMILES: CC(C)c1nc2c(n1Cc1ccc(Cl)cc1)C(OCC(=O)OC(C)(C)C)CCC2]

To a stirred solution of Intermediate 58 (352 mg) in anhydrous N,N-dimethylformamide (15 mL) at 0° C. under an atmosphere of nitrogen was added sodium hydride (55 mg) as a 60% by weight suspension on mineral oil in one charge. The reaction was stirred at 0° C. for 30 min. To the reaction was added neat tert-butyl bromoacetate (0.18 mL) in one charge the reaction was stirred at 0° C. for a further 30 min before allowing to warm to ambient temperature over 1 hr. The reaction was stirred at ambient temperature for 3 hr. Sodium hydride (55 mg) as a 60% wt suspension on oil was added and the reaction stirred for 30 min. To the reaction was added tert-butyl bromoacetate (0.18 mL) in one charge. The reaction was quenched with water (75 mL) and extracted with ethyl acetate (75 mL). The extract was dried (hydrophobic frit) and concentrated in vacuo. The sample was loaded in dichloromethane and purified on silica using a 0-25% methanol-dichloromethane gradient. Separation poor all product containing fractions were combined and concentrated in vacuo. The sample was loaded in dichloromethane and purified on silica using a 0-100% ethyl acetate-cyclohexane gradient.

The appropriate fractions were combined and concentrated in vacuo to give the title compound (130 mg). LC/MS MH+ 419, 421, Rt 1.00 min (2 min run). Chiral separation of this material using a chiralpak AD column eluting with 5% ethanol in heptane to provide the two enantiomers in order of elution:

Intermediate 61 (1,1-dimethylethyl{[1-[(4-chlorophenyl)methyl]-2-(1-methylethyl)-4,5,6,7-tetrahydro-1H-benzimidazol-7-yl]oxy}acetate (isomer 1)

21 mg LC/MS MH+ 419, Rt 2.07 min (5 min run).

Intermediate 62 (1,1-dimethylethyl{[1-[(4-chlorophenyl)methyl]-2-(1-methylethyl)-4,5,6,7-tetrahydro-1H-benzimidazol-7-yl]oxy}acetate (isomer 2)

14 mg LC/MS MH+ 419, Rt 2.08 min (5 min run).

Example 25

{[1-[(4-chlorophenyl)methyl]-2-(1-methylethyl)-4,5,6,7-tetrahydro-1H-benzimidazol-7-yl]oxy}acetic acid formic acid salt (isomer 1)

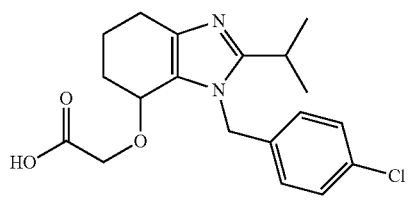 [SMILES: CC(C)c1nc2c(n1Cc1ccc(Cl)cc1)C(OCC(=O)O)CCC2]

To a stirred solution of Intermediate 61 isomer 1 (21 mg) in dichloromethane (2 mL) was added neat trifluoroacetic acid (0.1 mL) in one charge. The reaction was stirred at 40° C. for 18 h. The reaction was concentrated. The sample was dissolved in 1:1 MeOH:DMSO 0.5 ml and purified by MDAP (Method A). The solvent was dried under a stream of nitrogen in the Radleys blowdown apparatus to give the required product (3.2 mg). LC/MS MH+ 363, Rt 1.47 min (5 min run).

Example 26

{[1-[(4-chlorophenyl)methyl]-2-(1-methylethyl)-4,5,6,7-tetrahydro-1H-benzimidazol-7-yl]oxy}acetic acid formic acid salt (isomer 2)

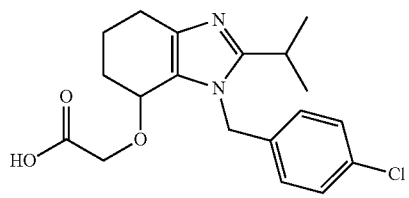 [SMILES: CC(C)c1nc2c(n1Cc1ccc(Cl)cc1)C(OCC(=O)O)CCC2]

Prepared in exactly the same way as Example 25 from 14 mg of Intermediate 62. (5.5 mg).

LC/MS MH+ 363, Rt 1.51 min (5 min run). NB insufficient material to obtain an optical rotation.

Intermediate 64 Triethyl [1-[(4-chlorophenyl)methyl]-2-(1-methylethyl)-4,5,6,7-tetrahydro-1H-benzimidazol-7-yl]methanetricarboxylate

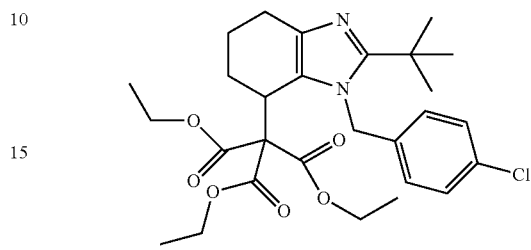

To a stirred solution of Intermediate 58 (99 mg) and triethylmethanetricarboxylate (0.14 mL) in anhydrous Toluene (3 mL) and anhydrous Tetrahydrofuran (THF) (3.00 mL) under a nitrogen atmosphere was added trimethylphosphine, 1M in Toluene (0.650 mL). The reaction was then cooled to −78° C. and diisopropyl azodicarboxylate (0.13 mL) added dropwise via syringe over 1 min. The reaction was stirred at −78° C. under an atmosphere of nitrogen for 90 mins before being allowed to warm to ambient temperature and stirred for a further 1 h. The reaction was concentrated in vacuo. The residue was taken up in dichloromethane (40 mL) and washed with water (40 mL), dried (hydrophobic frit) and concentrated in vacuo. The sample was loaded in dichloromethane and purified on silica using a 0-100% ethyl acetate-cyclohexane gradient. The appropriate fractions were combined and evaporated in vacuo to give the required product (139 mg). LC/MS MH+ 519, Rt 2.15 min (5 min run).

Example 27

[1-[(4-chlorophenyl)methyl]-2-(1-methylethyl)-4,5,6,7-tetrahydro-1H-benzimidazol-7-yl]acetic acid ammonia salt

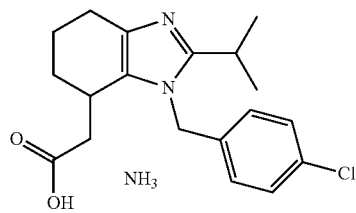

To a stirred solution of triethyl Intermediate 64 (130 mg) in methanol (6 mL) at ambient temperature was added 3.3 M aqueous sodium hydroxide (2.25 mL) in one charge. The reaction was heated to reflux for 16 h. The reaction was allowed to cool and concentrated in vacuo. The residue was taken up in glacial acetic acid (20 mL) and heated to reflux for a further 1 h. The reaction was concentrated in vacuo. The residue was taken up in methanol and flushed through a silica plug (2 g). The eluent was concentrated in vacuo. The sample was loaded in methanol and purified by SPE on sulphonic acid (SCX) 20 g washed with 1:1 methanol:dichloromethane and eluted with 2M ammonia in methanol. The appropriate fractions were combined and evaporated in vacuo to give the required product. (30 mg).

LC/MS MH+ 347, Rt 1.53 min (5 min run).

Example 28

[3-[(4-chlorophenyl)methyl]-2-(1-methylethyl)-3,4,5,6-tetrahydrocyclopenta[d]imidazol-4-yl]acetic acid

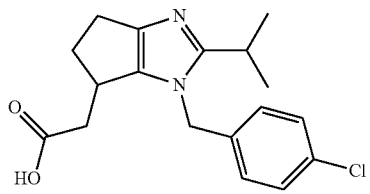 [SMILES: CC(C)c1nc2c(n1Cc1ccc(Cl)cc1)C(CC(=O)O)CC2]

Intermediate 20 (250 mg) was dissolved in ethanol (10 ml) and the resulting soln was treated with sodium hydroxide, 3M aq (4 ml). The resulting suspension was heated to reflux for 4 h. The reaction mixture was allowed to cool and concentrated in vacuo. The crude residue was taken up in Acetic Acid (10.00 ml) and heated to reflux for 2 h. Reaction mixture concentrated in vacuo and was purified by Reverse Phase chromatography using a 5->80% gradient of Acetonitrile/water with an ammonium carbonate modifier over 12 column volumes. The desired fractions were combined and concentrated under vacuum to give material that was repurified by Reverse Phase chromatography using a 5->80% gradient of acetonitrile water with 0.1% formic acid. The desired fractions were combined and concentrated under vacuum to give the title compound (33 mg). MH+=333 LC/MS MH+333, Rt 1.84 min (5 min run).

Example 29

[1-[(3,4-dichlorophenyl)methyl]-2-(1-methylethyl)-4,5,6,7-tetrahydro-1H-benzimidazol-7-yl]acetic acid trifluoroacetic acid salt

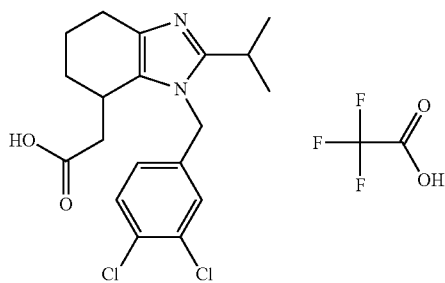 [SMILES: CC(C)c1nc2c(n1Cc1ccc(Cl)c(Cl)c1)C(CC(=O)O)CCC2 ; O=C(O)C(F)(F)F]

Intermediate 47 (36 mg) was dissolved in methanol (1 mL) and sodium hydroxide (3.52 mg) was added as a 3.3 N soln in water. The reaction mixture was left to stir at RT for 4 h. The reaction mixture was diluted with water (20 ml) and neutralised with 2M aqueous hydrogen chloride solution. The aqueous mixture was extracted with ether (2×20 ml), filtered through a phase separator and conc in vacuo to afford the crude product. The aqueous phase was run down a SCX column, washed with methanol and flushed with ammonia/methanol to obtain to product. However, this led to formation of a considerable amount of the methyl ester. The product obtained from both aqueous and organic phases were purified by MDAP (Method C) and the product-containing fraction was blown down to afford 13.6 mg of the title compound. LC/MS MH+ 381/383/385, Rt 2.10 mins (5 min system).

Intermediate 65 Phenylmethyl(2-hydroxy-3-oxo-1-cyclohexen-1-yl)acetate

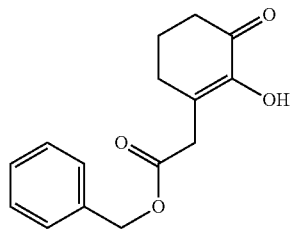 [SMILES: O=C(CC1=C(O)C(=O)CCC1)OCc1ccccc1]

A 1.6M solution of n-butyl lithium (81 mL, 130 mmol) was added to a stirred solution of diisopropylamine (18.26 mL) in methyl-THF (150 mL) at −10° C. The resulting solution was stirred at −10° C. for 15 mins. 1,2-cyclohexanedione (6.84 g) was added to the reaction mixture as a solution in methyl-THF (30 mL). During the addition the internal temperature of the reaction was maintained between −15° C. and −5° C. by modulation of delivery rate. The resulting dark orange/brown solution was stirred at −10 to −20° C. for a further 15 mins. The reaction mixture was then cooled to −50° C. and benzyl bromoacetate (12.62 mL, 79 mmol) was added dropwise via syringe. The mixture was stirred at this temperature for 10 minutes then aged at −78° C. for 1½ hours. The reaction mixture was quenched at −78° C. by dropwise addition of 1M HCl (300 ml). Ethyl acetate (200 mL) was added and the mixture allowed to warm to room temperature. The layers were separated and the organic phase washed with saturated brine (150 mL) and dried over sodium sulfate then reduced in vacuo. The resulting solid was purified by column chromatography, eluting with 0-25% ethyl acetate in cyclohexane. The appropriate fractions were reduced in vacuo to provide the product as a 1:1 mixture of thermodynamic enol:kinetic enol (registered as thermodynamic enol)

LC/MS MH+ 261, Rt 2.54 min (5 min system).

Intermediate 66 Phenylmethyl [1-[(1S)-1-(4-chlorophenyl)ethyl]-2-(1-methylethyl)-4,5,6,7-tetrahydro-1H-benzimidazol-7-yl]acetate

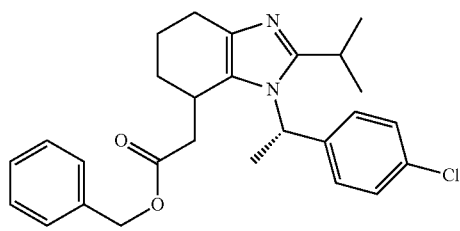 [SMILES: CC(C)c1nc2c(n1[C@@H](C)c1ccc(Cl)cc1)C(CC(=O)OCc1ccccc1)CCC2]

Acetic acid (0.572 mL) and ammonium acetate (154 mg) were mixed, to this were added Intermediate 65 (521 mg), isobutyraldehyde (0.196 mL) and (1S)-1-(4-chlorophenyl)ethanamine (0.362 mL) in chloroform (1.5 mL) and heated to reflux overnight. The mixture was reduced in vacuo and purified by column chromatography (0-100% ethyl acetate in cyclohexane). The appropriate fractions were concentrated in vacuo to yield 171 mg of the title compound. LC/MS MH+ 452, Rt 3.50 mins (5 min system, High ph).

Example 30

[1-[(1S)-1-(4-chlorophenyl)ethyl]-2-(1-methylethyl)-4,5,6,7-tetrahydro-1H-benzimidazol-7-yl]acetic acid ammonia salt

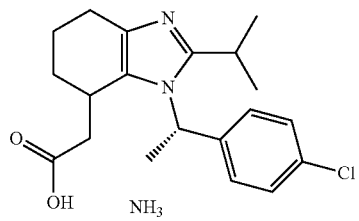

Intermediate 66 (177 mg) was dissolved in methanol (4 mL). NaOH (2 mL, 6.60 mmol) was added to the stirred reaction mixture as a 3.3 N aqueous soln and the reaction mixture. After stirring overnight the reaction mixture was conc in vacuo and taken up in acetonitrile/water. The soln was taken to pH4-5 by the addition of 2 M aqueous HCl and loaded onto an SCX column. After washing with water and acetonitrile, the product was eluted with 2 M ammonia soln in methanol. The washing were conc in vacuo to afford the ammonium salt of the desired product. LC/MS, MH+ 361, Rt 2.01 mins (5 min system).

Intermediate 67 Phenylmethyl {2(1-methylethyl)-1-[(1R)-1-phenylethyl]-4,5,6,7-tetrahydro-1H-benzimidazol-7-yl}acetate

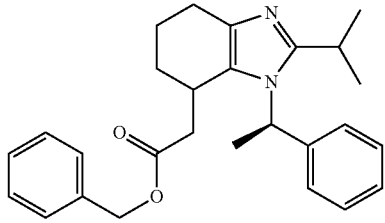 [SMILES: CC(C)c1nc2c(n1[C@H](C)c1ccccc1)C(CC(=O)OCc1ccccc1)CCC2]

Ammonium acetate (0.154 g) was dissolved in acetic acid (0.572 mL), to this was added Intermediate 65 (0.615 g), (1R)-1-phenylethanamine (0.362 mL) and isobutyraldehyde (0.216 mL, 2.363 mmol). The mixture was dissolved in chloroform (1.5 mL) and heated to reflux overnight. The mixture was reduced in vacuo and purified by column chromatography (0-100% ethyl acetate in cyclohexane). The appropriate fractions were concentrated in vacuo to yield 224 mg. LC/MS, MH+ 417, Rt 3.33 mins (5 min system, High ph).

Example 31

{2-(1-methylethyl)-1-[(1R)-1-phenylethyl]-4,5,6,7-tetrahydro-1H-benzimidazol-7-yl}acetic acid ammonia salt

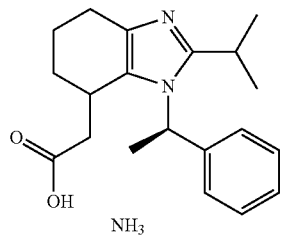

Intermediate 67 (224 mg) was dissolved in methanol (4 mL). NaOH (2 mL, 6.60 mmol) was added to the stirred reaction mixture as a 3.3 N aqueous soln. After stirring overnight the reaction mixture was conc in vacuo and taken up in acetonitrile/water. The soln was taken to pH4-5 by the addition of 2 M aqueous HCl and loaded onto an SCX column. After washing with water and acetonitrile, the product was eluted with 2 M ammonia soln in methanol. The washing were conc in vacuo to afford the ammonium salt of the desired product (84 mg).

LC/MS MH+ 327, Rt 1.84 mins (5 min system).

Intermediate 69 Phenylmethyl [1-[(1R)-1-(4-chlorophenyl)ethyl]-2-(1-methylethyl)-4,5,6,7-tetrahydro-1H-benzimidazol-7-yl]acetate

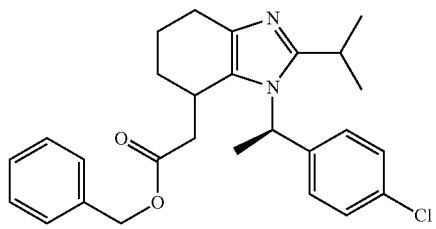 [SMILES: CC(C)c1nc2c(n1[C@H](C)c1ccc(Cl)cc1)C(CC(=O)OCc1ccccc1)CCC2]

Ammonium acetate (0.154 g) was dissolved in acetic acid (0.572 mL), to this was added Intermediate 65 (0.560 g), (1R)-1-(4-chlorophenyl)ethanamine (0.362 mL) and isobutyraldehyde (0.196 mL), the mixture dissolved in chloroform (2 mL) and heated to reflux overnight. The mixture was reduced in vacuo and purified by column chromatography (0-100% ethyl acetate in cyclohexane). The appropriate fractions were concentrated in vacuo to yield the racemic mixture of the desired regioisomer. LC/MS MH+ 452, Rt 3.50 mins (5 min run, High pH).

Example 33

[1-[(1R)-1-(4-chlorophenyl)ethyl]-2-(1-methylethyl)-4,5,6,7-tetrahydro-1H-benzimidazol-7-yl]acetic acid ammonia salt

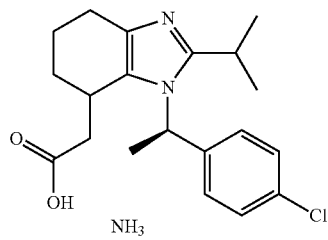

Intermediate 69 (147 mg) was dissolved in Methanol (4 mL). NaOH (2 mL) was added to the stirred reaction mixture as a 3.3 N aqueous soln and the reaction mixture stirred at room temperature. After stirring overnight, LCMS of the reaction mixture demonstrated full consumption of the starting material and the formation of the desired acid product. The reaction mixture was conc in vacuo and taken up in acetonitrile/water. The soln was taken to pH4-5 by the addition of 2 M aqueous HCl and loaded onto an SCX column. After washing with water and acetonitrile, the product was eluted with 2 M ammonia soln in methanol. The washings were conc in vacuo to afford the ammonium salt of the desired product: LC/MS MH+ 361, Rt 2.02 mins (5 min run).

Intermediate 70 Ethyl {[3-[(3,4-dichlorophenyl)methyl]-2-(1-methylethyl)-3,4,5,6,7,8-hexahydrocyclohepta[d]imidazol-4-yl]oxy}acetate

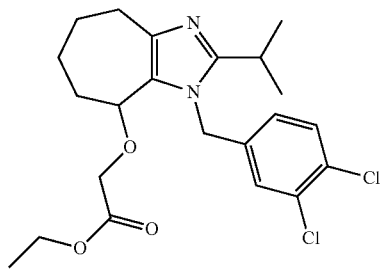 [SMILES: CCOC(=O)COC1CCCCc2nc(C(C)C)n(Cc3ccc(Cl)c(Cl)c3)c21]

To a stirred solution of Intermediate 8 (300 mg) in anhydrous Tetrahydrofuran (THF) (3 mL) at 0° C. under an atmosphere of nitrogen was added sodium hydride (102 mg, 2.55 mmol) as a 60% by weight suspension on mineral oil in one charge. The reaction was stirred at 0° C. for 30 min. To the reaction was added neat ethyl bromoacetate (0.284 mL) in one charge the reaction was then gradually allowed to warm to ambient temperature under an atmosphere of nitrogen over 20 hours. LCMS (high pH) showed a mixture of DP:SM (1:1). The reaction mixture was partitioned between EtOAc (50 ml) and sat NH4Cl aq sol (30 ml). The two phases were separated and the aqueous phase was extracted again with EtOAc (30 ml). The phases were separated, the organic extracts were combined, dried (hydrophobic frit) and concentrated under vacuum. The residue was by column chromatography on silica using a Cyclohexane:Ethyl acetate 0-100% gradient+Ethyl acetate:Methanol 0-20% gradient. The desired fractions were combined and concentrated under vacuum to give the desired product, 220 mg, yellow oil. LC/MS MH+ 439/441, Rt 3.37 mins (5 min run, high pH).

Example 34

{[3-[(3,4-dichlorophenyl)methyl]-2-(1-methylethyl)-3,4,5,6,7,8-hexahydrocyclohepta[d]imidazol-4-yl]oxy}acetic acid ammonia salt

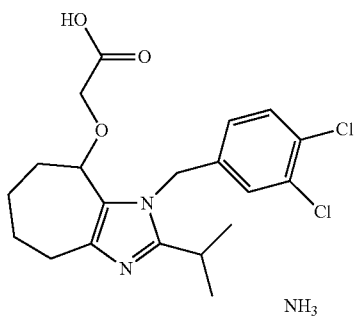

A mixture of Intermediate 70 (110 mg) and Sodium hydroxide, 2M aq (1 mL) in Ethanol (3 mL) was stirred at RT for 16 h. 2M aq HCL was added to reach pH=7. The solvent was concentrated under vacuum. The residue was dissolved in Acetonitrile:water (1:1, 4 mL) and eluted through an SCX column (20 g). The column was washed with Acetonitrile:water (1:1, 2 column volumes) and then with 2M NH3 in MeOH (2 column volumes). The ammonia fraction was concentrated under vacuum to give a white solid (84 mg). LCMS showed the DP contaminated with 20% of the Methyl ester. The residue was purified by MDAP (Method B). The solvent was evaporated in vacuo to give the required product (32 mg, white solid).

LC/MS MH+ 411/413, Rt 2.1 mins (5 min run, High pH).

Intermediate 71 1,1-dimethylethyl{[3-[(3,4-dichlorophenyl)methyl]-2-(1-methylethyl)-3,4,5,6,7,8-hexahydrocyclohepta[d]imidazol-4-yl]oxy}acetate

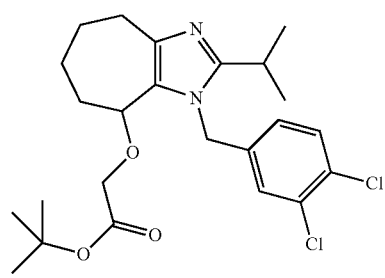 [SMILES: CC(C)c1nc2c(n1Cc1ccc(Cl)c(Cl)c1)C(OCC(=O)OC(C)(C)C)CCCC2]

Intermediate 8 (574 mg) was dissolved in 1,1-dimethylethyl bromoacetate (0.360 mL). NaOH (65.0 mg) was dissolved in Water (0.78 mL) and added to the organic phase. At this point Dichloromethane (DCM) (0.78 mL) was added followed by the phase transfer catalyst tetra-n-butylammonium sulfate (16.55 mg). The reaction mixture was stirred under Nitrogen overnight at room temperature. LCMS showed almost complete conversion to the product. The organic layer was separated from the aqueous layer through a phase separator. The aqueous layer was washed with further fractions of DCM (2 mL). The organic layer was concentrated in vacuo. The residue was preabsorbed on florisil and purified by column chromatography (0-25% EtOAc:Cyclohexane). The product did not come off the column, therefore the column was washed with 250 mL of EtOAc and the sample was concentrated in vacuo to give the pure clean product. LC/MS MH+ 467, Rt 2.62 mins (5 min run, TFA modifier).

Example 35

{[3-[(3,4-dichlorophenyl)methyl]-2-(1-methylethyl)-3,4,5,6,7,8-hexahydrocyclohepta[d]imidazol-4-yl]oxy}acetic acid hydrochloride

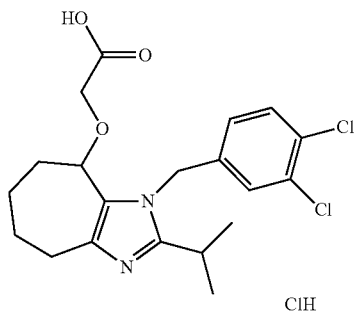 [SMILES: CC(C)c1nc2c(n1Cc1ccc(Cl)c(Cl)c1)C(OCC(=O)O)CCCC2 ; Cl]

Intermediate 71 (0.210 g) was stirred in HCl (0.899 mL) and 1,4-Dioxane (0.9 mL) for 1 hour under an atmosphere of Nitrogen. The reaction was allowed to stir overnight. LCMS showed 60% conversion to the product. The reaction mixture was allowed to stir over a second night. LCMS showed further conversion to the product. The sample was concentrated in vacuo and then re-dissolved in 2 mL of a 1:1 mixture of ACN:H$_2$O. An aminopropyl column was washed with 2 CV of ACN:H$_2$O (1:1), then the sample was loaded onto the column. The column was washed with 3 CV of ACN:H$_2$O (1:1). The product was eluted with 3CV of 2N HCl. The appropriate fraction was concentrated in vacuo to give the product. There is an impurity (about 10%) which has the m/z of the methyl ester of the product.

LC/MS MH+ 410, Rt 2.11 mins (5 min run, high pH).

Intermediate 74 1,1-dimethylethyl{[3-[(3,4-dichlorophenyl)methyl]-2-(1-methylethyl)-3,4,5,6,7,8-hexahydrocyclohepta[d]imidazol-4-yl]oxy}acetate (Isomer 1)

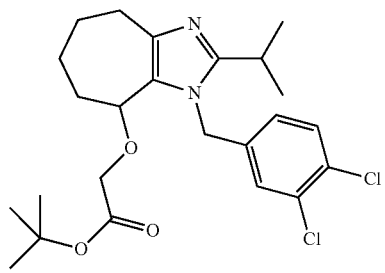 [SMILES: CC(C)c1nc2c(n1Cc1ccc(Cl)c(Cl)c1)C(OCC(=O)OC(C)(C)C)CCCC2]

Intermediate 72 (200 mg) was dissolved in 1,1-dimethylethyl bromoacetate (0.125 mL). NaOH (0.226 mL) and tetra-n-butylammonium sulfate (19.22 mg) were then added. The reaction mixture was stirred for 8 hours under an atmosphere of Nitrogen. LCMS showed a ratio of 2:1 starting material to product. 1,1-dimethylethyl bromoacetat (0.125 mL) was then added. The reaction mixture was then stirred over the weekend. LCMS showed a ratio of 3:2 starting material to product. DCM (50 mL) was added along with 50 mL of 5% Citric acid. The organic layer was separated and the aqueous layer was washed with further fractions of DCM (2×50 mL). The organic layers were combined and concentrated in vacuo. LCMS and NMR showed a ratio of 3:2 starting material to product. The crude mass was 226 mgs. 20 mgs was purified by MDAP (Method B). 2.3 mgs of the ester were isolated. LC/MS MH+ 467, Rt 2.34 mins (5 min run). The remaining mixture was progressed crude to be purified upon conversion to the acid.

Example 36

{[3-[(3,4-dichlorophenyl)methyl]-2-(1-methylethyl)-3,4,5,6,7,8-hexahydrocyclohepta[d]imidazol-4-yl]oxy}acetic acid ammonia salt (Isomer 1)

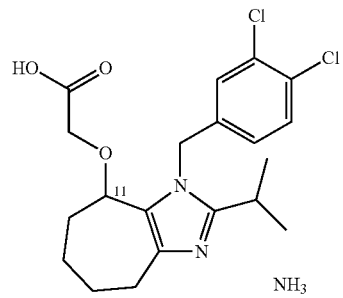

Intermediate 74 (180 mg) was stirred in HCl (1.93 mL) and 1,4-Dioxane (1 mL) for 2.5 hours. LCMS showed complete conversion of the ester to the acid. However there was still about 40% residual alcohol in this sample therefore the sample was concentrated and was re-dissolved in 10 mL of ACN:H$_2$O (1:1) and placed on a 70 g NH$_2$ (amino-propyl column). The column was initially washed with 10 mL of ACN:H$_2$O (1:1). The column (after the sample had been placed on the column) was washed with 5 column volumes of ACN:H$_2$O (1:1). The acid was eluted with 2 column volumes of HCl which had been diluted with water until it reached pH~3. The product did not come off therefore the column was washed with 5 column volumes of 2N HCl. After analysis of the fractions the product came off in the 5 CV of ACN:H$_2$O. This fraction was concentrated in vacuo and LCMS confirmed about a 90:10 ratio of product and an impurity. The sample was purified by pH MDAP method B. The fraction was concentrated in vacuo and dried on the high vac line to give the product. LCMS MH+ 411, Rt 1.82 mins (5 min run).

Intermediate 75 1,1-dimethylethyl{[3-[(3,4-dichlorophenyl)methyl]-2-(1-methylethyl)-3,4,5,6,7,8-hexahydrocyclohepta[d]imidazol-4-yl]oxy}acetate (Isomer 2)

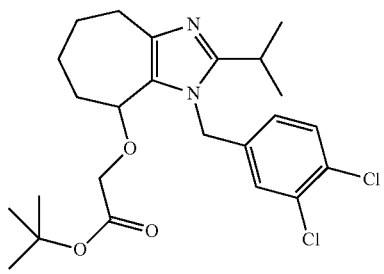 [SMILES: CC(C)c1nc2c(n1Cc1ccc(Cl)c(Cl)c1)C(OCC(=O)OC(C)(C)C)CCCC2]

Intermediate 73 (200 mg) was dissolved in 1,1-dimethylethyl bromoacetate (125 ul). NaOH (226 ul, 5.66 mmol) and tetra-n-butylammonium sulfate (19.2 mg) were then added. The reaction mixture was stirred for 8 hours under an atmosphere of Nitrogen. LCMS showed a ratio of 2:1 starting material to product. 1,1-dimethylethyl bromoacetate (125 ul) was then added. The reaction mixture was then stirred over the weekend. LCMS showed a ratio of 3:2 starting material to product. DCM (50 mL) was added along with 50 mL of 5% Citric acid. The organic layer was separated and the aqueous layer was washed with further fractions of DCM (2×50 mL). The organic layers were combined and concentrated in vacuo. LCMS and NMR showed a ratio of 3:2 starting material to product. The crude mass was 220 mgs. 20 mgs was purified on MDAP (method B). 2.0 mgs of the ester were isolated. LC/MS MH+ 467, Rt 2.30 mins (5 min run). The remainder of the material was used crude in the next step.

Example 37

{[3-[(3,4-dichlorophenyl)methyl]-2-(1-methylethyl)-3,4,5,6,7,8-hexahydrocyclohepta[d]imidazol-4-yl]oxy}acetic acid ammonia salt (Isomer 2)

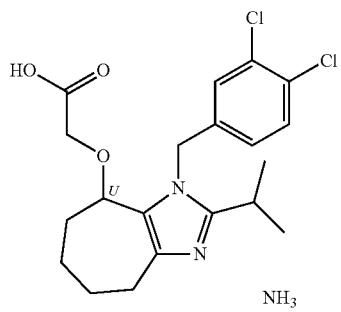

Intermediate 75 (180 mg) was stirred in 2M HCl (3851 ul) for 2 and a half hours. The sample was concentrated and the LCMS showed complete conversion of the ester to the acid. There was still the impurity of the alcohol. The sample was dissolved in 10 mL of ACN:H$_2$O (1:1) and placed on a 50 g NH$_2$ (amino propyl column). The column was initially washed with 10 mL of ACN:H$_2$O (1:1). The column (after the sample had been placed on the column) was washed with 3 column volumes of ACN:H$_2$O (1:1). The acid was eluted with 2 column volumes of HCl which had been diluted with water until it reached pH~3. The sample was concentrated and showed about 20% impurity. The sample was titurated with ACN:H$_2$O (1:1). The impurity was not removed. The column was washed with 5 CV of 2N HCl but did not elute the product. The product was found in the 3 CV ACN:H$_2$O wash and the 2CV wash with HCl. These fractions were concentrated in vacuo. The sample was purified by MDAP (Method B). The appropriate fractions were concentrated in vacuo to give the product.

LCMS, MH+ 411, Rt 1.82 mins (5 min run).

Intermediate 76 2-[1-[(4-chlorophenyl)methyl]-2-(1-methylethyl)-4,5,6,7-tetrahydro-1H-benzimidazol-7-yl]ethanol-borane complex

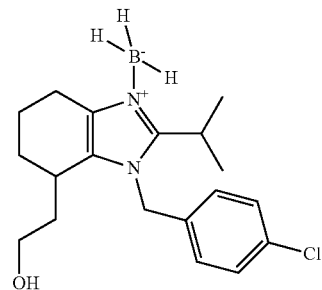 [SMILES: [BH3-][n+]1c2c(n(Cc3ccc(Cl)cc3)c1C(C)C)C(CCO)CCC2]

Example 15 (2 g) was stirred in anhydrous Tetrahydrofuran (THF) (80 mL) under nitrogen and the resulting solution was cooled to −78° C. Borane-dimethylsulfide complex (2.187 mL) was added dropwise via syringe. Once the addition was completed, the reaction mixture was allowed to warm to RT and stirred overnight. LCMS analysis after this time demonstrated consumption of the starting material.

The reaction mixture was quenched with 20 mL water, then partitioned between brine (250 mL) and ether (250 mL). The organic layer was separated and the aqueous phase washed with a further portion of ether (250 mL). The combined organic layers were passed through a hydrophobic frit and concentrated in vacuo to afford 1.72 g of crude product. The product was purified by column chromatography (100 g silica, 0-100% ethyl acetate/cyclohexane) to afford the desired alcohol (1.11 g) LC/MS MH+ 333/335, Rt 1.95 mins (5 min run, TFA modifier). $^1$H NMR (CDCl$_3$ d6) δ 1.22-1.30 (m, 7H), 1.42 (m, 1H), 1.5-1.9 (m, 7H), 2.2 (br.s, 3H), 2.52 (m, 1H), 2.67 (q, 1H), 2.83 (dd, 1H), 3.62 (m, 3H), 5.71 (s, 2H), 6.81 (d, 2H), 7.29 (d, 1H).

It was noted that whilst NMR and LCMS were consistent with the desired alcohol, the LCMS demonstrated a pH-dependent second peak with the mass ion 386/388, the integration of this peak increasing at higher pH. It was also noted that the 1H NMR contained a broad peak around 2 ppm. These phenomena were due to the imidazole existing as a (imidazole)N—BH3 borane complex, the molecular ion, 386/388, of the second peak corresponding to (M+Acetonitrile+BH3-H)+ and it's pH-dependancy resulting from the partial breakdown of this complex in acid-buffered LCMS.

Intermediate 77 2-[1-[(4-chlorophenyl)methyl]-2-(1-methylethyl)-4,5,6,7-tetrahydro-1H-benzimidazol-7-yl]ethyl methanesulfonate-borane complex

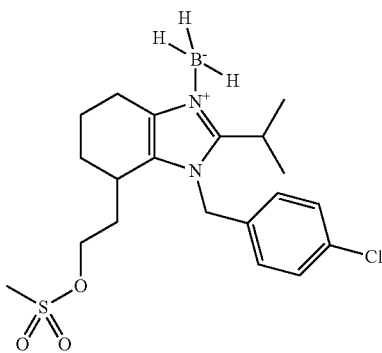 [SMILES: [BH3-][n+]1c2c(n(Cc3ccc(Cl)cc3)c1C(C)C)C(CCOS(C)(=O)=O)CCC2]

A stirred suspension of Intermediate 76 (830 mg) in Dichloromethane (DCM) (40 mL), under nitrogen, was treated with triethylamine (0.501 mL) then cooled to ca. 0° C. (ice bath). Methanesulfonyl chloride (0.222 mL) was added via syringe, then the cooling bath was removed and stirring continued for 2 h. The solution was partitioned between aqueous ammonium chloride (200 ml) and DCM (200 ml). The layers were separated and the aqueous phase was further extracted with DCM (200 ml). The combined organic extracts were washed with water (200 mL), dried (Na2SO4), filtered through a hydrophobic frit and evaporated in vacuo. The crude product was purified by column chromatography (silica, 0-25% Methanol in DCM). The appropriate fractions were combined and concentrated to afford the title compound, 368 mg. LC/MS (M-BH2)-411/413, Rt 2.18 mins (5 min run, TFA modifier).

Intermediate 78 3-[1-[(4-chlorophenyl)methyl]-2-(1-methylethyl)-4,5,6,7-tetrahydro-1H-benzimidazol-7-yl]propanenitrile

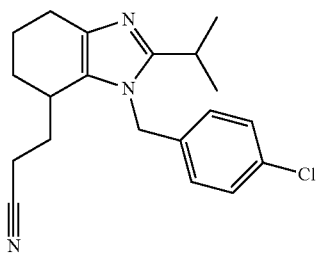 [SMILES: CC(C)c1nc2c(n1Cc1ccc(Cl)cc1)C(CCC#N)CCC2]

A stirred solution of Intermediate 77 (225 mg, 0.530 mmol) in Dimethyl Sulfoxide (DMSO) (2 mL) was treated with sodium cyanide (78 mg, 1.589 mmol) and heated at 60° C. overnight. After cooling the mixture was partitioned between DCM (50 ml) and water (50 ml). The layers were separated and the aqueous phase was further extracted with DCM (50 ml). The combined organic extracts were washed with water (50 ml), dried (Na2SO4), filtered and evaporated in vacuo. The crude product was purified via flash column chromatography (silica, 25-100% EtOAc/cyclohexane) to afford 111.4 mg of product. LC/MS MH+ 342/344, Rt 2.11 mins (5 min run, TFA modifier). The borane complex appears to have partially dissociated in the reaction conditions and the free imidazole and borane-complex were separable by chromatography. However, in this case, in order to maximise yield, the free imidazole and borane-imidazole complex containing fractions were combined to afford the final product as an approximately 60(free imidazole):40(borane complex) mixture of the two species. The borane complex was also apparent in the LCMS, with a second peak evident; Rt 3.27 mins, (M+BH2+acetonitrile)+395/397.

Example 38

3-[1-[(4-chlorophenyl)methyl]-2-(1-methylethyl)-4,5,6,7-tetrahydro-1H-benzimidazol-7-yl]propanoic acid

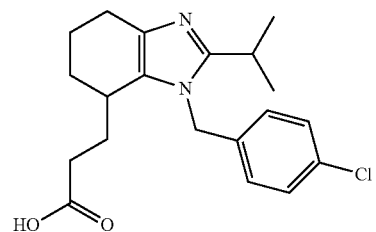 [SMILES: CC(C)c1nc2c(n1Cc1ccc(Cl)cc1)C(CCC(=O)O)CCC2]

A solution of Intermediate 78 (128 mg, two batches) in Methanol (3.5 mL) and potassium hydroxide (10M aqueous soln) (0.749 mL) was heated to reflux overnight. LCMS after 18 h indicated approximately 20% conversion to the acid. Further potassium hydroxide (10M aqueous soln) (0.749 mL was added to the reaction mixture and it was left to heat for a further 36 h. LCMS after this time demonstrated full conversion to the acid product. Aqueous HCl (4.85 mL) was added to the reaction mixture to neutralise to the KOH. The product was extracted from the reaction mixture using EtOAc. The organic layer was washed with water, brine and then dried over MgSO$_4$ and filtered, before being concentrated in vacuo to give the product, 88 mg. LC/MS MH+ 361, Rt 2.02 mins (5 min run, TFA modifier).

Intermediate 79 Phenylmethyl 3-[1-[(4-chlorophenyl)methyl]-2-(1-methylethyl)-4,5,6,7-tetrahydro-1H-benzimidazol-7-yl]propanoate

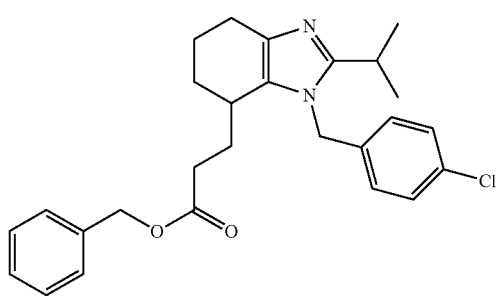 [SMILES: CC(C)c1nc2c(n1Cc1ccc(Cl)cc1)C(CCC(=O)OCc1ccccc1)CCC2]

To a stirred suspension of Example 38 (78 mg) in Dichloromethane (DCM) (3 mL) at 0° C. was added benzyl alcohol (0.045 mL), 4-dimethylamino pyridine (4.75 mg) and N'-(3-dimethylaminopropyl)-N-ethylcarbodiimide hydrochloride (47.5 mg) sequentially. The reaction was stirred at 0° C. under an atmosphere of nitrogen for 1.5 h. The reaction was allowed to achieve ambient temperature and stirred for 5 days. LCMS analysis after this time demonstrated approximately 60% conversion of starting material to product. Therefore, further Dichloromethane (DCM) (3 mL) was added, along with further portions of benzyl alcohol (0.045 mL) and N'-(3-dimethylaminopropyl)-N-ethylcarbodiimide hydrochloride (47.5 mg). The reaction mixture was left to stir at RT. LCMS analysis after stirring for a further 5 h demonstrated complete consumption of the starting material. The reaction mixture was partitioned between dichloromethane (10 mL) and water (10 mL). The aqueous phase was back extracted with dichloromethane (10 mL). The combined organics were dried (hydrophobic frit) and concentrated in vacuo to afford the crude product. The crude product was purified by flash column chromatography (silica, 0-100% cyclohexane/ethyl acetate). The appropriate fractions were combined and concentrated in vacuo to afford (48.6 mg). LC/MS MH+ 451/453, Rt 2.66 mins (5 min system, TFA buffer). The product was resolved by preparative chiral HPLC on a Chiralpak AD column eluting with ethanol/heptane. The second isomer to elute was progressed to provide Example 39.

Example 39

3-[1-[(4-chlorophenyl)methyl]-2-(1-methylethyl)-4,5,6,7-tetrahydro-1H-benzimidazol-7-yl]propanoic acid ammonia salt (Isomer 2)

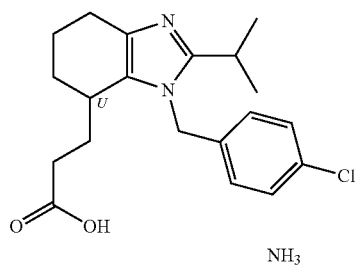

Phenylmethyl 3-[1-[(4-chlorophenyl)methyl]-2-(1-methylethyl)-4,5,6,7-tetrahydro-1H-benzimidazol-7-yl]propanoate (second isomer from chiral HPLC, 18 mg) was dissolved in Methanol (1.5 mL). 3.3 M aqueous sodium hydroxide solution (0.5 mL) was added and the reaction mixture was left to stir at RT. After stirring for 18 h, LCMS of the reaction mixture demonstrated full consumption of the starting material and the formation of the desired acid product. The reaction mixture was concentrated in vacuo and taken up in acetonitrile/water. The resulting solution was acidified to pH 5-6 and loaded onto a 20 g SCX column. The column was washed with two column volumes of acetonitrile/water and then eluted with 10% ammonia in ethanol. The basic washings were concentrated in vacuo to afford the desired product as the ammonium salt (10.1 mg). LC/MS MH+ 361/363, Rt 1.87 mins (5 min system, TFA modifier).

Intermediate 80 3-[(3,4-dichlorophenyl)methyl]-2-(1-methylethyl)-3,5,6,7-tetrahydro-4H-benzimidazol-4-one

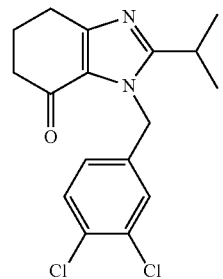 [SMILES: CC(C)c1nc2c(n1Cc1ccc(Cl)c(Cl)c1)C(=O)CCC2]

To Intermediate 56 (1$^{st}$ Alternative preparation) (88.83 g, product of multiple previous experiments) was added toluene (2000 mL) followed by 4-(bromomethyl)-1,2-dichlorobenzene (132 g) and tetrabutylammonium bromide (80 g) then sodium hydroxide (1096 mL). The mixture was then stirred at room temperature, stirring vigorously to mix the phases. The temp rose by 5° C. over 5 mins. After 1.5 hr the mixture was partitioned between ethyl acetate and water and the aqueous layer extracted well with ethyl acetate—aq phase got up to 50° C. The combined organics were washed with water, brine, dried (MgSO$_4$), filtered and evaporated. The crude product was purified by column chromatography, loaded in DCM, eluting with 0-100% ethyl acetate in cyclohexane. The appropriate fractions were evaporated and this gave the title compound, a cream solid, two batches 114.8 gm and 16.22 gm. LC/MS MH$^+$337, 339, Rt 0.96 min (2 min run).

Intermediate 81 1-[(3,4-dichlorophenyl)methyl]-2-(1-methylethyl)-4,5,6,7-tetrahydro-1H-benzimidazol-7-ol

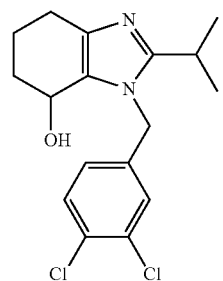 [SMILES: CC(C)c1nc2c(n1Cc1ccc(Cl)c(Cl)c1)C(O)CCC2]

To Intermediate 80 (131.02 g, combination of two batches) under nitrogen in methanol (1000 mL) and dichloromethane (DCM) (1000 mL) was added sodium borohydride (29.4 g) slowly in portions over 10 min and the mixture stirred at room temperature under nitrogen. Temp rose from 19° C. to 23° C. Gas evolution still visible for 20-30 mins and temp rose over 40 mins to 26° C. Temp still going up after 1 hr20 min—now 26.2° C. After 2.5 hr water was added carefully and the mixture was partitioned between ethyl acetate and water (should have given the mixture more time to quench before extracting—gas evolution during extraction seen) and the aqueous layer extracted well with ethyl acetate. The combined organics were washed with water, brine, dried (MgSO₄), filtered and evaporated. This gave the title compound, a white solid, 133.3 gm. LC/MS MH⁺ 339, 341, Rt 0.76 min (2 min run).

Intermediate 82 Triethyl [1-[(3,4-dichlorophenyl)methyl]-2-(1-methylethyl)-4,5,6,7-tetrahydro-1H-benzimidazol-7-yl]methanetricarboxylate

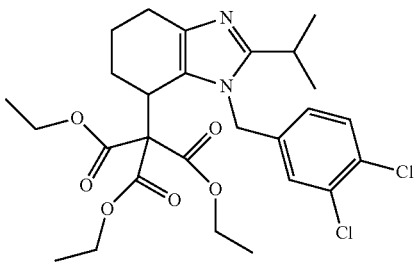 [SMILES: CCOC(=O)C(C(=O)OCC)(C(=O)OCC)C1CCCc2nc(C(C)C)n(Cc3ccc(Cl)c(Cl)c3)c21]

To a stirred solution of Intermediate 81 (65.4 g) in toluene (1000 mL) and anhydrous Tetrahydrofuran (THF) (1000 mL) under a nitrogen atmosphere was added triethylmethanetricarboxylate (83 mL) followed by trimethylphosphine (39.7 mL, 386 mmol). The reaction was then cooled to −78° C. (bath temp, internal −64° C.) and diisopropyl azodicarboxylate (77 mL) added dropwise via dropping funnel over 20 min. Internal temp got as high as −60° C. at the end of the addition. Became yellow (DIAD was orange). The reaction was then stirred at −78° C. (internal down to −71° C.) under an atmosphere of nitrogen. Because the reaction seems very slow when cold the cooling bath was removed after 20 mins and the yellow solution allowed to warm to room temperature. After 50 mins internal temp=−30° C. After 2.25 hr the solvent was evaporated before partitioning just to remove much of the THF and the residue was partitioned between dichloromethane and water and the aqueous layer extracted well with dichloromethane. The combined organics were washed with water, brine, dried (MgSO₄), filtered and evaporated. 2.5 gm of this was stirred in 5 ml of 1:1 cyclohexane:ether and gave 0.5 gm of a white solid. 0.8 gm of this was stirred in 5 ml of cyclohexane and gave 0.32 gm of a white solid so this was checked by NMR: (CDCl3) showed ~4:1 DIAD imp: product. All of the crude product and the solid sample above were stirred well with ~600 ml of cyclohexane and filtered. This gave a white solid, 130 gm, NMR showed 4.8:1 DIAD imp: product by integration so calculations give Imp 83 gm, product 47 gm. The filtrate was evaporated to give 97.6 gm of a yellow oil. This was combined with a residue from a previous experiment, loaded in DCM and purified by column chromatography (silica cartridge), eluting with 0-100% ethyl acetate in cyclohexane. Fractions were checked by tlc—the DIAD imp runs faster and is visible under iodine. The appropriate fractions were combined and the solvent removed. This gave the title compound, a white solid, 46.3 gm, (from two reactions). LC/MS Rt 1.07 min (2 min run). The crude filtered solid above was combined with mixed fractions from a previous experiment and this experiment and evaporated down to give a white solid, 186 gm. This was dissolved in DCM and purified by column chromatography (silica cartridge), eluting with 0-100% ethyl acetate in cyclohexane, pausing the gradient at ~30% to allow more time for the DIAD imp to elute. Fractions were checked by tlc and the appropriate fractions combined. This gave the title compound, a white solid, 70.92 gm (from two reactions). LC/MS MH⁺ 553, 555, Rt 1.09 min (2 min run).

Intermediate 83. Triethyl [(7R)-1-[(3,4-dichlorophenyl)methyl]-2-(1-methylethyl)-4,5,6,7-tetrahydro-1H-benzimidazol-7-yl]methanetricarboxylate

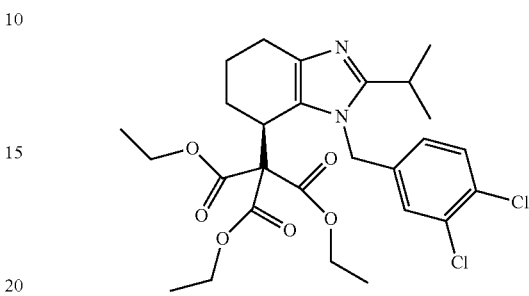

Chiral chromatography was used to purify several combined batches of Intermediate 82 on a Chiracel AD column, eluting with ethanol in heptane. This gave 90.42 gm of the desired isomer. LC/MS MH⁺ 553, 555, Rt 1.1 min (2 min run).

Example 40

[(7R)-1-[(3,4-dichlorophenyl)methyl]-2-(1-methylethyl)-4,5,6,7-tetrahydro-1H-benzimidazol-7-yl]acetic acid

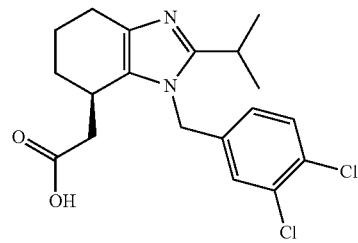 [SMILES: CC(C)c1nc2c(n1Cc1ccc(Cl)c(Cl)c1)[C@@H](CC(=O)O)CCC2]

To a solution of triethyl Intermediate 83 (88.5 g) in ethanol (1200 mL) was added 2M aqueous sodium hydroxide 2M (320 mL). Took 5 mins for all the SM to dissolve and the resulting solution was heated at 80° C. for 2 hours under an atmosphere of nitrogen and the mixture became cloudy as the reaction progressed as solid precipitated out. Reaction continued, It is important to get this first stage to go as cleanly as possible to ensure clean product. After 3.5 hrs the reaction mixture was allowed to cool slightly and then concentrated in vacuo. The residue was treated with acetic acid, glacial (366 mL) and then heated at 120° C. After 1.75 hr the reaction mixture was concentrated in vacuo and put under high vacuum overnight. Tried to dissolve this solid in hot water— initially 330 ml used at 65° C. (max recommended=960 ml) and in this case virtually all of it dissolved as it was rotated on an evaporator. The solution then started to become more cloudy so it was allowed to cool to room temperature, still rotating, then in an ice-bath for 2 hours (for convenience). The solid was collected by vacuum filtration and washed with ice-cold water, sucked dry then dried under high vacuum at 40° C. overnight. This gave a white crystalline solid (23.15 gm). The extra water used for washing caused more solid to precipitate out in the filtrate. The filtrate was re-filtered but all the material went through as an emulsion. So more water was added (up to ~950 ml originally intended) and the mixture stirred to allow solid to form. The solid was collected by vacuum filtration, washed with water, sucked dry and put under high vacuum at 40° C. overnight. This gave a white crispy solid that ground down to a powder, 29.06 gm. Both batches have the same main impurity, though they look different, so they were combined and stirred slowly to mix and help grind down lumps for ~1.75 hour in a 4:1 mixture of ether:ethyl acetate, (400 ml ether, 100 ml EtOAc). The solid was collected by vacuum filtration and was found to contain the ethyl ester. The solid (51 gm) was suspended in methanol (400 ml) and to this was added 1M NaOH (670 ml) and the resulting solution stirred at room temperature for 30 mins. The solution was then evaporated to remove the methanol and it became cloudy whilst doing so. The suspension was treated with 2M HCl to pH 5 and the material did not dissolve this time but the appearance of the solid changed. The solid was allowed to stir for 1 hr in an ice-bath to ensure there was no emulsion and that the pH had stabilised then collected by vacuum filtration, washed with ice-cold water, sucked dry then put under high vacuum overnight at 40° C. This gave the title compound, a white solid, 49.72 gm. $[\alpha]_D = -12.8°$ (22° C., 1:1 ethanol:DCM). Chiral analysis: ratio of enantiomers=99.65:0.34 i.e. 99.3% ee $^1$H NMR (DMSO d6) δ 1.02 (d, 3H), 1.11 (d, 3H), 1.60-1.78 (m, 4H), 2.20-2.48 (m, 4H), 2.82 (pent., 1H), 2.93 (m, 1H), 5.09 (d, 1H), 5.19 (d, 1H), 6.66 (dd, 1H), 7.23 (d, 1H), 7.62 (d, 1H), (12.1 br.s, 1H).

A X-ray powder diffraction pattern for this compound is shown in FIG. 1.

A DSC thermogram for this compound is shown in FIG. 3.

Example 40

(1$^{st}$ Alternative Preparation) [(7R)-1-[(3,4-dichlorophenyl)methyl]-2-(1-methylethyl)-4,5,6,7-tetrahydro-1H-benzimidazol-7-yl]acetic acid

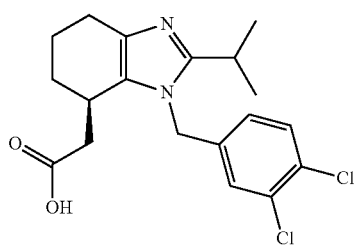 [SMILES: CC(C)c1nc2c(n1Cc1ccc(Cl)c(Cl)c1)[C@@H](CC(=O)O)CCC2]

Intermediate 86 (800 g, 1.0 eq, 1.0 wt) was dissolved in anhydrous tetrahydrofuran (2.32 L, 2.9 vol) at 40° C. The solution was cooled to 20° C. Heptane (1.6 L, 2 vol) was charged to a second vessel, followed by triethyl methanetricarboxylate (712 g, 0.89 wt, 1.3 eq). After a line rinse with toluene (0.08 L, 0.1 vol) the mixture was stirred at 20° C. and 1M trimethylphosphine in toluene solution (3 L, 3.75 vol, 1.27 eq) was added over 15 minutes. After a line rinse with toluene (0.08 L, 0.1 vol) the mixture was cooled to −10° C. and diisopropylazodicarboxylate (528 g, 0.66 wt, 1.1 eq, 0.64 vol) was added over 15 minutes at <0° C. After a line rinse with toluene (0.04 L, 0.05 vol) the mixture was cooled to −15° C. and the solution of (7R)-1-[(3,4-dichlorophenyl)methyl]-2-(1-methylethyl)-4,5,6,7-tetrahydro-1H-benzimidazol-7-ol in tetrahydrofuran was added over 1 hour at −15° C. After a line rinse with tetrahydrofuran (0.2 L, 0.25 vol), the reaction mixture was stirred at −15° C. for 1 hour 30 minutes, and sampled for completion by HPLC. Reaction was complete. The mixture was warmed to 0° C. with vigorous stirring. A 5% w/w aqueous sodium hypochlorite solution (3.2 L, 4 vol) was added over 15 minutes at <25° C. and the mixture stirred for a further 30 minutes. The aqueous phase was separated and the organic phase was washed with water (2.4 L, 3 vol). The organic phase was concentrated by atmospheric distillation to 3.2 L/4 vol. Heptane (8 L, 10 vol) was added and the solvent composition was checked by NMR. The ratio of heptane to toluene was lower than expected so further heptane (1.6 L, 2 vol) was added. The mixture was cooled to 60° C. and seeded with a mixture of triethyl [1-[(3,4-dichlorophenyl)methyl]-2-(1-methylethyl)-4,5,6,7-tetrahydro-1H-benzimidazol-7-yl]methanetricarboxylate (racemate of the trimester intermediate) and bis(1-methylethyl)1,2-hydrazinedicarboxylate(diisopropylazodicarboxylate reduced impurity). The slurry was aged at 60° C. for 1 hour, cooled to 20° C. over 2 hours and stirred at this temperature for 14 hours. The solids (Mixture of triethyl [1-[(3,4-dichlorophenyl)methyl]-2-(1-methylethyl)-4,5,6,7-tetrahydro-1H-benzimidazol-7-yl]methanetricarboxylate and 1,2-hydrazinedicarboxylate) were collected by vacuum filtration, washed with heptane (2×1.6 L, 2×2 vol) and discarded. The filtrate and the heptane washes containing triethyl [(7R)-1-[(3,4-dichlorophenyl)methyl]-2-(1-methylethyl)-4,5,6,7-tetrahydro-1H-benzimidazol-7-yl]methanetricarboxylate (Intermediate 83) were combined and returned to a clean vessel and concentrated by atmospheric distillation to 8 L/10 vol. Methanol (1.6 L, 2 vol) was added and the mixture stirred vigorously at 25° C. for 5 minutes. A biphasic mixture did not result so further heptane (1.6 L, 2 vol) was added. The lower methanol phase was separated and the heptane phase was washed with further methanol (1.6 L, 2 vol) by stirring vigorously at 25° C. The phases were separated and the combined methanol phases were returned to the vessel. 10M aqueous sodium hydroxide (1.2 L, 1.5 vol) was added. The mixture was warmed to 60° C. and stirred at this temperature for at 1 hour 15 minutes and sampled for completion by HPLC. Reaction was complete. Water (5.6 L, 7 vol) was added and the mixture was concentrated by atmospheric distillation to 8 L/10 vol. The mixture was cooled to 20° C. and tert-butylmethylether (4.8 L, 6 vol) was added and the organic phase separated and discarded. The aqueous phase was returned to a clean vessel and warmed to 60° C. Water (8 L, 10 vol) was charged. Glacial acetic acid (6 L, 7.5 vol) was charged over 2 hours at 60° C. The mixture was warmed to 95° C. for 16 hours and sampled for completion by HPLC. Reaction was complete. The mixture was cooled to 80° C. 10M aqueous sodium hydroxide (4 L, 5 vol) was added to the mixture at 80° C. over 30 minutes to adjust the pH from 3 to 4.4. Crystallisation occurred during this addition. The slurry was aged at 75° C. for 1 hour, cooled to 20° C. over 2 hours and stirred at this temperature for 1 hour. Solids were collected by vacuum filtration, washed with water (2×3.2 L, 2×4 vol), followed by tert-butylmethylether (2×3.2 L, 2×4 vol), and dried in vacuo at 50° C. for 24 hours. Yield of [(7R)-1-[(3,4-dichlorophenyl)methyl]-2-(1-methylethyl)-4,5,6,7-tetrahydro-1H-benzimidazol-7-yl]acetic acid obtained was 346 g/38% theory yield/43% w/w yield.

A X-ray powder diffraction pattern for this compound is shown in FIG. 2.

A DSC thermogram for this compound is shown in FIG. 4.

Intermediate 84 2-(1-methylethyl)-1,5,6,7-tetrahydro-4H-benzimidazol-4-one, hydrochloride

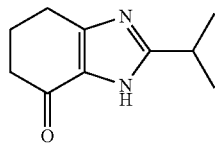

3-(ethyloxy)-2-cyclohexen-1-one (1000 g, 1.0 eq, 1.0 wt) was dissolved in acetonitrile (5 L, 5 vol) at 0° C. and N-bromosuccinimide (1295 g, 1.02 eq, 1.295 wt) was added in four equal portions over 1 hour at <5° C. The mixture was stirred for 15 minutes at 0° C., warmed to 20° C. and stirred for a further 15 minutes at this temperature and sampled for completion by HPLC. Reaction was complete. 2-methylpropanimidamide (981 g, 1.1 eq, 0.981 wt) was added and the mixture stirred for 5 minutes at 20° C. Anhydrous sodium carbonate (1134 g, 1.5 eq, 1.134 wt) was charged to the vessel and the contents warmed to 65° C., stirred for a further 2 hours and sampled for completion by HPLC. Reaction was complete. Water (7 L, 7 vol) was added at 60° C. and the contents stirred for a further 15 minutes. 2-methyltetrahydrofuran (7 L, 7 vol) was added at 50° C. The suspension was cooled to 25° C., filtered and the inorganic solids washed with 2-methyltetrahydrofuran (2 L, 2 vol). The biphase was stirred for 5 minutes, settled and separated. The aqueous phase was back-extracted with 2-methyltetrahydrofuran (5 L, 5 vol). The combined organic phases were concentrated by atmospheric distillation to 5 L/5 vol. Toluene (10 L, 10 vol) was added, the mixture was concentrated by atmospheric distillation to 5 L/5 vol and cooled to 60° C. 5-6M hydrochloric acid in propan-2-ol (2 L, 1.3 eq, 2 vol) was added over 35 minutes at 60° C. Crystallisation was observed towards the end of the addition. The slurry was aged at 60° C. for 1 hour, cooled to 0° C. over 4 hours and stirred at this temperature for 10 hours 45 minutes. Solids were collected by vacuum filtration, washed with chilled (5° C.) toluene/propan-2-ol (2×2.5 L, 2:1 v/v, 2×2.5 vol), followed by tert-butylmethylether (2×2.5 L, 2×2.5 vol) and dried in vacuo at 50° C. for 5 hours. Yield of title compound obtained was 887 g, however this contained 13.2% w/w succinic acid and 4.2% w/w inorganics. Corrected yield was therefore 736 g/48% theory yield/74% w/w yield.

Intermediate 85 3-[(3,4-dichlorophenyl)methyl]-2-(1-methylethyl)-3,5,6,7-tetrahydro-4H-benzimidazol-4-one hydrochloride

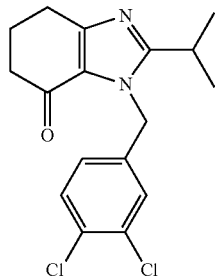 [SMILES: CC(C)c1nc2c(n1Cc1ccc(Cl)c(Cl)c1)C(=O)CCC2]

To a mixture of Intermediate 84 (1000 g, 1.0 eq, 1.0 wt) and tetrabutylammonium bromide (300 g, 0.2 eq, 0.3 wt) in toluene (9.5 L, 9.5 vol) was added 3,4-dichlorobenzyl bromide (0.71 L, 1.05 eq, 0.71 vol), followed by a line rinse with toluene (0.5 L, 0.5 vol). 5M sodium hydroxide (5 L, 5.36 eq, 5 vol) was added and the biphasic mixture was stirred vigorously for 4 hours 30 minutes at 20° C. and sampled for completion by HPLC. Reaction was complete at 3 hours 30 minutes. The mixture was settled and separated. The aqueous phase was back-extracted with toluene (5 L, 5 vol). The combined organic phases were washed with water (2×2 L, 2×2 vol) and concentrated by atmospheric distillation to 3.4 L/3.4 vol. The mixture was cooled to 20° C. over 30 minutes and diluted with propan-2-ol (10 L, 10 vol). 5-6M hydrochloric acid in propan-2-ol (1.4 L, 1.5 eq, 1.40 vol) was added over 10 minutes at 55° C. The solution was stirred at 60° C. for 20 minutes and seeded with a sample of the title compound (0.4 g, 0.0004 wt). The slurry was aged at 60° C. for 30 minutes, cooled to 3° C. over 3 hours 15 minutes and stirred at this temperature for 1 hour 30 minutes. Solids were collected by vacuum filtration, washed with chilled (5° C.) propan-2-ol/toluene (6 L, 5:1 v/v, 6 vol), followed by tert-butylmethylether (2×5 L, 2×5 vol) and dried in vacuo at 40° C. for 16 hours 30 minutes. Yield of the title compound obtained was 1497 g/86% theory yield/150% w/w yield.

Intermediate 86 (7R)-1-[(3,4-dichlorophenyl)methyl]-2-(1-methylethyl)-4,5,6,7-tetrahydro-1H-benzimidazol-7-ol

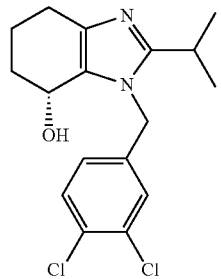

Intermediate 85 (900 g, 1.0 eq, 1.0 wt) was charged to a solution of (S)-(−)-2-methyl-CBS-oxazaborolidine (198 g, 0.3 eq, 0.22 wt) in tetrahydrofuran (3.6 L, 4 vol) at 20° C., followed by a line rinse with tetrahydrofuran (0.9 L, 1 vol). The suspension was cooled to 0° C. and chilled (0° C.) 1M borane in tetrahydrofuran solution (4.82 L, 2 eq 5.35 vol) was added over 1 hour 35 minutes at <3° C. The mixture was stirred at 0° C. for 1 hour 20 minutes when complete dissolution was observed and sampled for completion by HPLC. Reaction was complete. The mixture was added into chilled (0° C.) methanol (3.6 L, 4 vol) at <5° C. over 40 minutes, followed by a line rinse with methanol (0.9 L, 1 vol). The mixture was warmed to 20° C. and stirred at this temperature for 1 hour 15 minutes when effervescence had ceased. Water (2.7 L, 3 vol) was added, followed by the addition of 5M aqueous hydrochloric acid (0.9 L, 1 vol) at <10° C. over 10 minutes. The mixture was warmed to 20° C. and stirred at this temperature for 1 hour when effervescence had ceased. To the mixture was added 48% w/w aqueous sodium hydroxide (0.99 L, 1.1 vol) at <30° C. over 15 minutes and the mixture stirred vigorously for 10 minutes at 20° C. The basic aqueous layer was separated. The organic phase was diluted with isopropylacetate (3.6 L, 4 vol) and washed with water (2.7 L, 3 vol). The aqueous phase was separated and the organic phase was concentrated by vacuum (100-200 mbar) distillation to 3.6 L/4 vol at 25° C. To the mixture was added isopropylacetate (5.4 L, 6 vol), followed by water (6 L, 6.7 vol) and the mixture stirred vigorously for 10 minutes at 20° C. The aqueous phase was separated and the organic phase was concentrated by vacuum distillation on a rotary evaporator. The solids were slurried in heptane (9 L, 10 vol) on the rotary evaporator at 40 C for 1 hour and stirred at this temperature for 16 hours. The solids were collected by vacuum filtration, washed with heptane (2×0.9 L, 2×1 vol) and dried in vacuo at 40° C. for 23 hours 30 minutes. Yield of the title compound obtained was 739 g/90% theory yield/82% w/w yield.

Intermediate 87 3-[(4-iodophenyl)methyl]-2-(1-methylethyl)-3,5,6,7-tetrahydro-4H-benzimidazol-4-one

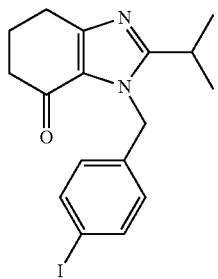 [SMILES: CC(C)c1nc2c(n1Cc1ccc(I)cc1)C(=O)CCC2]

To Intermediate 56 ($2^{nd}$ alternative preparation) (5.4 g) in Toluene (120 mL) was added 1-(bromomethyl)-4-iodobenzene (9.00 g) and tetrabutylammonium bromide (4.88 g) then sodium hydroxide, 5M aq (66.7 mL). The mixture was then stirred at room temperature, stirring vigorously to mix the phases for 1.5 h. The mixture was partitioned between ethyl acetate and water. The brown solid was filtered. The 2 phases were separated and the aqueous layer extracted well with ethyl acetate. The combined organics were dried (hydrophobic frit) and evaporated. The sample was loaded in dichloromethane and purified by column chromatography (silica) using 0-100% ethyl acetate-cyclohexane. The appropriate fractions were combined and evaporated in vacuo to give the required product 6.65 g as a brown oil. LC/MS MH$^+$ 395, Rt 2.88 min (5 min run).

Intermediate 88 1-[(4-iodophenyl)methyl]-2-(1-methylethyl)-4,5,6,7-tetrahydro-1H-benzimidazol-7-ol

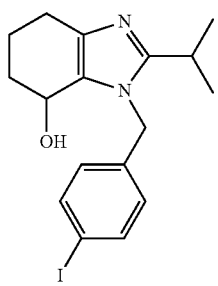 [SMILES: CC(C)c1nc2c(n1Cc1ccc(I)cc1)C(O)CCC2]

To Intermediate 87 (6.65 g) in a 250 mL round-bottom flask under nitrogen in Methanol (20 mL) and Dichloromethane (DCM) (20 mL) was added sodium borohydride (1.276 g) in three portions (effervescence) and the mixture stirred at room temperature under nitrogen for 16 h. The solvent was removed under vacuum and the residue was partitioned between ethyl acetate and water. The aqueous layer extracted well with ethyl acetate. The combined organics were dried (hydrophobic frit), filtered and evaporated to give the title compound 6.6 g as a white solid. LC/MS MH$^+$ 397, Rt 2.61 min (5 min run).

Intermediate 89 Methyl [1-[(4-iodophenyl)methyl]-2-(1-methylethyl)-4,5,6,7-tetrahydro-1H-benzimidazol-7-yl]methanetricarboxylate

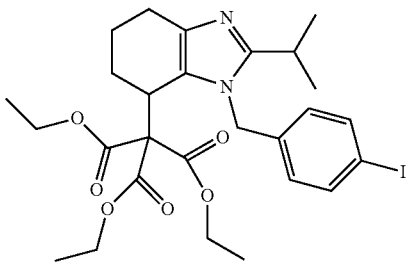 [SMILES: CCOC(=O)C(C(=O)OCC)(C(=O)OCC)C1CCCc2nc(C(C)C)n(Cc3ccc(I)cc3)c21]

To a suspension of Intermediate 88 (6.6 g) and triethylmethanetricarboxylate (7.06 ml) in Toluene (50 ml) and Methyltetrahydrofuran (50 ml), stirred at RT under an inert atmosphere of nitrogen, was added trimethylphosphine (3.45 ml). The resulting solution was cooled to −78 deg. C. and diisopropyl azodicarboxylate (6.56 ml) was added dropwise via syringe and the reaction was stirred at −78 deg. C. for 45 mins. the reaction mixture was removed from the cold bath and allowed to warm to RT and stirred under N2 atmosphere for 2 h. The solvent was removed under vacuum. The reaction mixture was partitioned between Dichloromethane (100 mL) and water (100 mL). The 2 phases were separated, the organic extract was dried (hydrophobic frit) and concentrated under vacuum. The sample was loaded in dichloromethane and purified by column chromatography (silica) using 0-100% ethyl acetate-cyclohexane. The appropriate fractions were combined and evaporated in vacuo to give the required product 11.1 g as a white solid. LC/MS MH$^+$ 611, Rt 3.57 min (5 min run).

Example 41

[1-[(4-iodophenyl)methyl]-2-(1-methylethyl)-4,5,6,7-tetrahydro-1H-benzimidazol-7-yl]acetic acid acetate

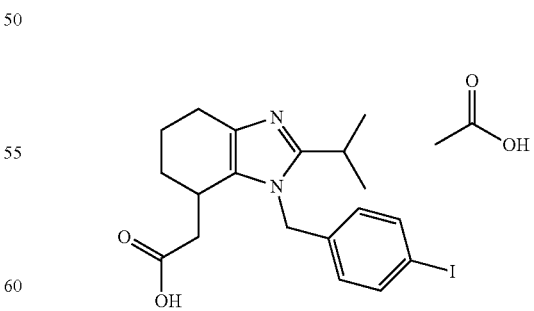

To a stirred solution of Intermediate 89 (11.1 g) in Ethanol (150 mL) was added 2M Aqueous Sodium Hydroxide (36.4 mL). The reaction mixture was then stirred at 80° C. and under nitrogen for 3 h. The reaction mixture was concentrated in vacuo, glacial acetic acid (41.6 mL, 727 mmol) added and allowed to stir at 120° C. and under nitrogen for 2 h. The reaction mixture was concentrated under vacuum. The white solid was suspended and stirred in ether (500 mL) for 5 mins. The white solid was filtered off under vacuum. The solid was suspended in EtOAc (500 mL) and the suspension was refluxed for 45 mins. The white solid was hot filtered under vacuum and washed with EtOAc (100 mL). The filtrate was concentrated under vacuum to give the title compound as a white solid (6.8 g). LC/MS MH+ 439, Rt 1.90 min (5 min run).

Intermediate 90 3-[(3-iodophenyl)methyl]-2-(1-methylethyl)-3,5,6,7-tetrahydro-4H-benzimidazol-4-one

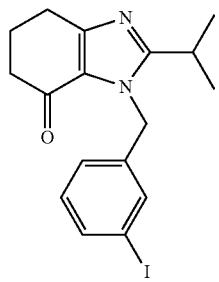 [SMILES: CC(C)c1nc2c(n1Cc1cccc(I)c1)C(=O)CCC2]

1-(bromomethyl)-3-iodobenzene (9.76 g) was added to a stirred solution of tetrabutylammonium bromide (4.41 g), Intermediate 56 (2$^{nd}$ alternative preparation) (4.88 g) and 1-(bromomethyl)-3-iodobenzene (9.76 g) in Toluene (100 mL) and NaOH (5M, Aq) (46.5 mL). The reaction mixture was allowed to stir vigorously, so as to ensure mixture of the 2 phases, at room temperature for 2.75 hr. The reaction mixture was partitioned between DCM (80 mL) and water (80 mL) and aqueous layer was washed with further DCM (2×80 mL). The organic layers were combined, filtered through a hydrophobic frit and concentrated in vacuo to give 16.84 g of crude product as a brown oil. The sample was loaded in dichloromethane and purified by column chromatography (silica) using 0-100% ethyl acetate-cyclohexane. The appropriate fractions were combined and evaporated in vacuo to give the required products 5.8 g as a yellow oil which solidified. LC/MS MH+ 394, Rt 2.85 min (5 min run).

Intermediate 91 1-[(3-iodophenyl)methyl]-2-(1-methylethyl)-4,5,6,7-tetrahydro-1H-benzimidazol-7-ol

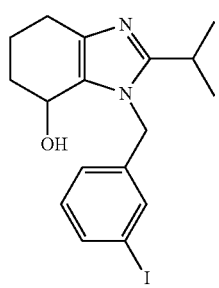 [SMILES: CC(C)c1nc2c(n1Cc1cccc(I)c1)C(O)CCC2]

NaBH4 (1.670 g) was added to a stirred solution of Intermediate 90 (5.8 g) in Dichloromethane (DCM) (30 mL) and Methanol (30 mL). The reaction mixture was stirred at room temperature for 3.5 hours. The reaction mixture was concentrated in vacuo before being partitioned between EtOAc (60 ml) and water (60 ml). The two phases were separated and the aqueous phase was extracted with further EtOAc (2×60 ml). The organic phases were combined, filtered through a hydrophobic frit and concentrated in vacuo to give the desired product (5.7 g) as an off white solid. LC/MS MH+ 397, Rt 2.54 min (5 min run).

Intermediate 92 triethyl [1-[(3-iodophenyl)methyl]-2-(1-methylethyl)-4,5,6,7-tetrahydro-1H-benzimidazol-7-yl]methanetricarboxylate

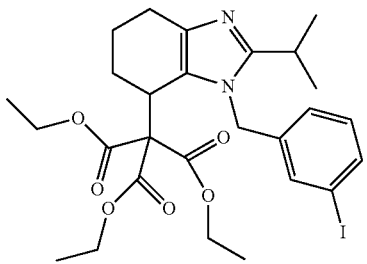 [SMILES: CCOC(=O)C(C(=O)OCC)(C(=O)OCC)C1CCCc2nc(C(C)C)n(Cc3cccc(I)c3)c21]

To a stirred solution of Intermediate 91 (5.7 g) in Toluene (50 mL) and 2-Methyltetrahydrofuran (2-MeTHF) (50 mL) under nitrogen was added triethyl methanetricarboxylate (6.14 mL) followed by trimethylphosphine (2.54 mL). The reaction mixture was then cooled to −78° C. and DIAD (5.68 mL) was added dropwise over 12 min. The reaction mixture was allowed to continue stirring at −78° C. and under nitrogen for a further 40 min. The reaction mixture was then allowed to warm to room temperature and allowed to stir for a further 2 hours while still under nitrogen. The reaction mixture was then concentrated in vacuo before being partitioned between DCM (50 mL) and water (50 mL). The phases were separated and the aqueous layer was washed with further DCM (2×50 mL). The organic phases were combined, filtered through a hydrophobic frit and concentrated in vacuo to give 19.8 g of crude product as an orange oil. The sample was loaded in dichloromethane and purified on by column chromatography (silica) using a 0-100% ethyl acetate-cyclohexane gradient. The appropriate fractions were combined and evaporated in vacuo to give the required product 7.67 g as an off-white solid. LC/MS MH+ 611, Rt 3.54 min (5 min run).

Example 42

[1-[(3-iodophenyl)methyl]-2-(1-methylethyl)-4,5,6,7-tetrahydro-1H-benzimidazol-7-yl]acetic acid acetate

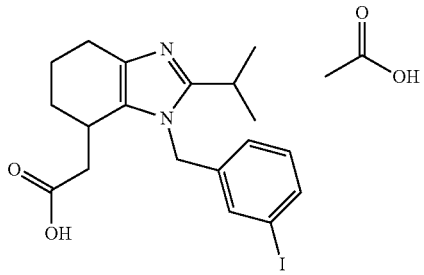

To a stirred solution of Intermediate 92 (7.67 g) in Methanol (150 mL) was added 2M Aqueous Sodium Hydroxide (25.1 mL). The reaction mixture was then stirred at 80° C. and under nitrogen for 17 hours. The reaction mixture was concentrated in vacuo, taken up in glacial acetic acid (28.8 mL) and allowed to stir at 80° C. and under nitrogen for 24 hours. The reaction mixture was concentrated in vacuo to give an orange oily solid. This was suspended in ether, stirred well for 15 mins and then filtered under vacuum. The white solid from this filtration was suspended in ethyl acetate and stirred well at 80° C. for 1.5 hours then filtered under vacuum to give 350 mg of the desired product as an off-white solid. LCMS of the filtrate from the first filtration showed the presence of the desired product as an ethyl ester and so 2M aqueous sodium hydroxide (5 mL) in methanol (5 mL) was added and the mixture left for 2 days. This sample was then loaded in 1:1 methanol:DMSO and purified by column chromatography, reverse phase (C18), using a 5-50% acetonitrile(+0.1% TFA)-water(+0.1% TFA) gradient and a further 80% acetonitrile(+0.1% TFA)-water(+0.1% TFA) gradient. The appropriate fractions were combined, evaporated in vacuo and added to the previously obtained product to give the required product 2.98 g as an off-white solid. LC/MS MH$^+$439, Rt 1.90 min (5 min run).

Biological Experimental
Experimental Preparation(s)
The following abbreviations are used in this document
Asym max—Asymptote maximum from curve fit
CHO—Chinese Hamster Ovary cells
DMEM—Dulbecco's Modified Eagle Medium—Cell medium
DMSO—dimethyl sulfoxide
EC80—Effective concentration to elicit 80% at the maximum response
FAC—final assay concentration
FCS—fetal bovine serum
HEPES—N-(2-hydroxyethyl)piperazine-N'-2-ethane-sulfonic acid
IBMX—3-Isobutyl-1-methylxanthine
KOH—Potassium hydroxide
Prep LNB Ref—Preparation lab notebook reference
PGD2—Prostaglandin D2
pXC$_{50}$—negative log of the mid point of a concentration/effect curve
TR-FRET-LANCET™—time resolved fluorescence. LANCE™ is the Perkin Elmer trade name for FRET reagents
Viewlux™—is an imaging reader (Wallac/Perkin Elmer)
Cell Production
CHO K1 cells, stably expressing the Prostanoid DP$_1$ receptor, were maintained in culture in DMEM/F12, supplemented with 5% FBS, 2 mM L-glutamine, 400 µg/mL hygromycin B in 95%: 5% air: CO$_2$ at 37° C. Following harvest from culture, cells were centrifuged at 250 g at 4° C. for 10 minutes and re-suspended in ice cold dialysed FCS. Once the cells were in mono-suspension they were slowly mixed with an equal volume of ice cold 80% dialysed FCS: 20% DMSO (pre-mixed and chilled several hours earlier). The cells were then aliquoted into 1 mL tubes within a 96 well block (pre-cooled to 4° C.). Once sealed, the tubes were frozen in a controlled rate freezer. The frozen cells were then transferred to a −140° C. freezer for long term storage.

Experimental Protocol(s)
Measurement of cAMP Using TR-FRET LANCE™ Assays: Prostanoid DP$_1$
The potency of the compounds were determined using a LANCE™ cAMP assay kit as per the kit instructions. Briefly, CHO cells expressing DP1 receptor were thawed at 37° C., diluted in PBS and centrifuged at 1000 RPM for 5 minutes. Cells were then re-suspended (2 million cells/mL) in stimulation buffer (HBSS containing 0.01% BSA, 500 µM FAC IBMX, 5 mmol/L HEPES adjusted to pH 7.4 with KOH.

Briefly, cells were added (10,000 cells/well at 5 µL addition) to low volume white Greiner polypropylene 384-well plate assay plates containing 0.1 µl test compound. Following a 15 minute incubation at room temperature, 5 µl of antibody solution (stimulation buffer containing Alexia fluor 647) containing PGD2 at twice the determined EC80 concentration was added. Plates were incubated for a further 30 minutes at room temperature then detection mixture was added (kit components; detection buffer, europiumW8044-labelled streptavidin and biotin cAMP at 10 µl/well). Plates were covered and incubated the room temperature for 1 hour before reading on a Viewlux Microplate Imager using TR-FRET label settings.

Drugs and Materials
All compounds were dissolved in DMSO at a concentration of 10 mM and were prepared in 100% DMSO using a 1 in 4 dilution step to provide 11-point concentration—response curves. The dilutions were transferred to the assay plates ensuring that the DMSO concentration was constant across the plate at 1% for all assays.

Data Analysis
All data were normalised to the mean of 16 high and 16 low control wells on each plate. A four parameter curve fit of the following form was then applied.

$$y = \frac{a-d}{1+(x/c)^b} + d$$

Where a is the minimum, b is the Hill slope, c is the XC$_{50}$, and d is the maximum. Data are presented as the mean pXC$_{50}$ (negative log 10 of the molar XC$_{50}$) with the standard deviation (SD) of number of tests in the experiments.

Results
All of the exemplified compounds were tested using the TR-FRET LANCE™ Assay: Prostanoid DP$_1$ receptor, and were found to have a pKi value greater than 6.0.

The compounds of Examples 1 to 7, 9 to 11, 14, 15, 17 to 20, 22 to 24, 26 to 29, 31 to 37, and 40 had a pKi value greater than or equal to 7.0.

The compounds of Examples 1, 3, 4, 6, 9, 10, 15, 17, 19, 20, 26, 29, 32, 34, 37, and 40 had a pKi value greater than or equal to 8.0.

The compound of Example 40 had a pKi value of approximately 8.6. A salt form of the compound of Example 40 (Example 20) had a pKi value of approximately 8.7.

What is claimed is:
1. A compound of formula (I)

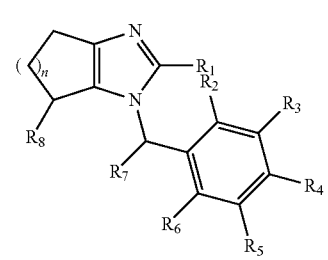

or a pharmaceutically acceptable salt or solvate thereof, wherein:
R₁ represents $C_{3-6}$ alkyl or $C_{3-6}$ cycloalkyl;
R₂, R₃, R₄, R₅ and R₆ each independently represent hydrogen or halogen;
R₇ represents hydrogen, $C_{1-4}$ alkyl or $C_{1-4}$ alkoxy;
R₈ represents —O(CH₂)ₓCOOH, —(CH₂)ₓCOOH wherein,
x is 1 or 2;
n represents 1, 2 or 3.

2. A compound according to claim 1, or a pharmaceutically acceptable salt or solvate thereof, wherein R₁ is propyl, butyl, cyclopropyl or cyclopentyl.

3. A compound according to claim 1, or a pharmaceutically acceptable salt or solvate thereof, wherein R₁ is iso-propyl.

4. A compound according to claim 1, or a pharmaceutically acceptable salt or solvate thereof, wherein:
R₇ is hydrogen;
R₈ is —(CH₂)COOH; and
R₄ is halogen.

5. A compound according to claim 4, or a pharmaceutically acceptable salt or solvate thereof, wherein R₄ is chloro.

6. A compound according to claim 1, or a pharmaceutically acceptable salt or solvate thereof, wherein:
R₁ is iso-propyl;
R₂, R₅, R₆ and R₇ are hydrogen;
R₃ is chloro or hydrogen;
R₄ is chloro;
R₈ is —(CH₂)COOH; and
n represents 1, 2 or 3.

7. A compound of formula (I) of claim 1 selected from the group consisting of:
[3-[(4-chlorophenyl)methyl]-2-(1-methylethyl)-3,4,5,6-tetrahydrocyclopenta[d]imidazol-4-yl]acetic acid,
[1-[(4-chlorophenyl)methyl]-2-(1-methylethyl)-4,5,6,7-tetrahydro-1H-benzimidazol-7-yl]acetic acid,
[3-[(4-chlorophenyl)methyl]-2-(1-methylethyl)-3,4,5,6,7,8-hexahydrocyclohepta[d]imidazol-4-yl]acetic acid,
[3-[(3,4-dichlorophenyl)methyl]-2-(1-methylethyl)-3,4,5,6-tetrahydrocyclopenta[d]imidazol-4-yl]acetic acid,
[1-[(3,4-dichlorophenyl)methyl]-2-(1-methylethyl)-4,5,6,7-tetrahydro-1H-benzimidazol-7-yl]acetic acid, and
[3-[(3,4-dichlorophenyl)methyl]-2-(1-methylethyl)-3,4,5,6,7,8-hexahydrocyclohepta[d]imidazol-4-yl]acetic acid;
or a pharmaceutically acceptable salt or solvate thereof.

8. A compound of formula (I) of claim 1 selected from the group consisting of:
(+)-[3-[(3,4-dichlorophenyl)methyl]-2-(1-methylethyl)-3,4,5,6,7,8-hexahydrocyclohepta[d]imidazol-4-yl]acetic acid,
(+)-[3-[(3,4-dichlorophenyl)methyl]-2-(1-methylethyl)-3,4,5,6-tetrahydrocyclopenta[d]imidazol-4-yl]acetic acid,
(−)-[1-[(4-chlorophenyl)methyl]-2-(1-methylethyl)-4,5,6,7-tetrahydro-1H-benzimidazol-7-yl]acetic acid, and
(−)-[1-[(3,4-dichlorophenyl)methyl]-2-(1-methylethyl)-4,5,6,7-tetrahydro-1H-benzimidazol-7-yl]acetic acid,
or a pharmaceutically acceptable salt or solvate thereof.

9. A compound according to claim 1, or a pharmaceutically acceptable salt or solvate thereof, wherein:
R₁ is iso-propyl;
R₂, R₅, R₆, R₇ are hydrogen;
R₃ and R₄ are chloro;
R₈ is —(CH₂)COOH; and
n represents 3.

10. (+)-[3-[(3,4-dichlorophenyl)methyl]-2-(1-methylethyl)-3,4,5,6,7,8-hexahydrocyclohepta[d]imidazol-4-yl]acetic acid, of formula

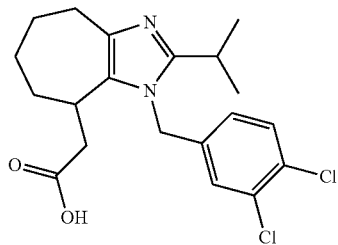 [SMILES: CC(C)c1nc2c(n1Cc1ccc(Cl)c(Cl)c1)C(CC(=O)O)CCCC2]

or a pharmaceutically acceptable salt or solvate thereof.

11. (−)-[1-[(3,4-dichlorophenyl)methyl]-2-(1-methylethyl)-4,5,6,7-tetrahydro-1H-benzimidazol-7-yl]acetic acid, of formula

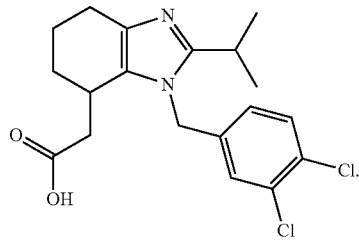 [SMILES: CC(C)c1nc2c(n1Cc1ccc(Cl)c(Cl)c1)C(CC(=O)O)CCC2]

12. (−)-[1-[(3,4-dichlorophenyl)methyl]-2-(1-methylethyl)-4,5,6,7-tetrahydro-1H-benzimidazol-7-yl]acetic acid, of formula

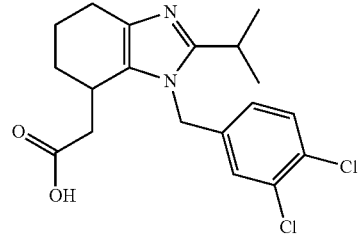 [SMILES: CC(C)c1nc2c(n1Cc1ccc(Cl)c(Cl)c1)C(CC(=O)O)CCC2]

or a pharmaceutically acceptable salt or solvate thereof.

13. [(7R)-1-[(3,4-dichlorophenyl)methyl]-2-(1-methylethyl)-4,5,6,7-tetrahydro-1H-benzimidazol-7-yl]acetic acid, of formula

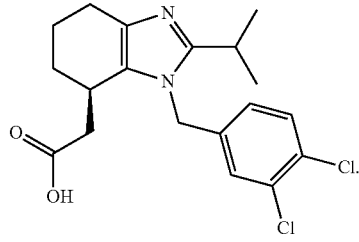 [SMILES: CC(C)c1nc2c(n1Cc1ccc(Cl)c(Cl)c1)[C@@H](CC(=O)O)CCC2]

14. A pharmaceutical composition comprising a) a compound according to claim 1, or a pharmaceutically acceptable salt or solvate thereof, and b) one or more pharmaceutically acceptable carriers or excipients.

15. A pharmaceutical composition comprising a) [3-[(3,4-dichlorophenyl)methyl]-2-(1-methylethyl)-3,4,5,6,7,8-hexahydrocyclohepta[d]imidazol-4-yl]acetic acid, or a pharmaceutically acceptable salt or solvate thereof, and b) one or more pharmaceutically acceptable carriers or excipients.

16. A pharmaceutical composition comprising a) (−)-[1-[(3,4-dichlorophenyl)methyl]-2-(1-methylethyl)-4,5,6,7-tetrahydro-1H-benzimidazol-7-yl]acetic acid, or a pharmaceutically acceptable salt or solvate thereof, and b) one or more pharmaceutically acceptable carriers or excipients.

17. A pharmaceutical composition according to claim 14, wherein the composition further comprises one or more therapeutic agents.

18. A method for treating allergic rhinitis, the method comprising administering to a patient in need of treatment a therapeutically effective amount of a compound according to claim 1.

* * * * *